United States Patent
Graham et al.

(10) Patent No.: US 11,219,732 B2
(45) Date of Patent: Jan. 11, 2022

(54) FRAME AND HEADGEAR FOR RESPIRATORY MASK SYSTEM

(71) Applicant: Fisher & Paykel Healthcare Limited, Auckland (NZ)

(72) Inventors: Ryan Anthony Graham, Auckland (NZ); Callum Ross Gordon, Auckland (NZ); Amit Galgali, Auckland (NZ); Mark Andrew Thompson, Auckland (NZ); Bruno Sintive, Auckland (NZ); Vicky Dan Gao, Auckland (NZ); Cameron Robert Willis, Auckland (NZ); Jake Baker Hocking, Auckland (NZ); Priyanka Ferdinand Pereira, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 313 days.

(21) Appl. No.: 16/085,923

(22) PCT Filed: Mar. 9, 2017

(86) PCT No.: PCT/IB2017/051371
§ 371 (c)(1),
(2) Date: Dec. 21, 2018

(87) PCT Pub. No.: WO2017/158474
PCT Pub. Date: Sep. 21, 2017

(65) Prior Publication Data
US 2019/0030272 A1 Jan. 31, 2019

Related U.S. Application Data
(60) Provisional application No. 62/310,537, filed on Mar. 18, 2016, provisional application No. 62/381,509, filed on Aug. 30, 2016.

(51) Int. Cl.
*A61M 16/06* (2006.01)
*A61M 16/00* (2006.01)
*F16B 21/06* (2006.01)

(52) U.S. Cl.
CPC ........ *A61M 16/0622* (2014.02); *A61M 16/00* (2013.01); *A61M 16/06* (2013.01);
(Continued)

(58) Field of Classification Search
CPC ...... A61M 16/0622; A61M 2210/0618; A61M 16/00–0655; A61M 16/0683–0694;
(Continued)

(56) References Cited

U.S. PATENT DOCUMENTS 139,663 A * 6/1873 Drake ................ A44B 13/0017
24/690
3,850,168 A * 11/1974 Ferguson ............. A62B 18/084
128/206.27
(Continued)

FOREIGN PATENT DOCUMENTS

WO WO 2012/028988 3/2012
WO WO 2017/042717 3/2014
(Continued)

OTHER PUBLICATIONS

Sep. 18, 2017, International Search Report for International Application No. PCT/IB2017/051371 filed on Mar. 9, 2017.

*Primary Examiner* — Justine R Ryu
*Assistant Examiner* — Alexander Morales
(74) *Attorney, Agent, or Firm* — Knobbe, Martens, Olson & Bear, LLP

(57) ABSTRACT

A respiratory mask system is provided. The respiratory mask system has a patient interface that is secured to a user's head by a headgear. The patient interface includes a seal, a frame and a gas delivery conduit. The frame is configured to secure
(Continued)

the seal and gas delivery conduit together. The frame includes a recessed channel and/or headgear retaining features configured to connect the headgear to the patient interface. The frame can include an inlet collar that connects to a gas delivery conduit. The inlet collar can include bias flow holes. The headgear includes a top strap, a pair of side arms, a yoke and a rear strap. The yoke is configured to connect to the recessed channel of the frame. The top strap, side arms and yoke form an integrally formed closed loop. The top strap can include two portions adjustably connected to each other.

21 Claims, 84 Drawing Sheets

(52) U.S. Cl.
CPC . *A61M 16/0683* (2013.01); *A61M 2210/0618* (2013.01); *F16B 21/06* (2013.01); *F16B 2200/20* (2018.08); *Y10T 24/4599* (2015.01); *Y10T 24/45796* (2015.01); *Y10T 403/60* (2015.01)

(58) Field of Classification Search
CPC .... A62B 7/00; A62B 7/02; A62B 7/08; A62B 7/10; A62B 7/12; A62B 7/14; A62B 9/04; A62B 18/00; A62B 18/02; A62B 18/025; A62B 18/04; A62B 18/08; A62B 18/084; F16B 21/06; F16B 2200/20; Y10T 403/60; Y10T 24/45796; Y10T 24/4599
See application file for complete search history.

(56) References Cited

U.S. PATENT DOCUMENTS

| | | | | |
|---|---|---|---|---|
| 4,774,946 | A * | 10/1988 | Ackerman | ........ A61M 16/0666 104/179 |
| 8,297,285 | B2 | 10/2012 | Henry et al. | |
| 8,387,616 | B2 | 3/2013 | Ging et al. | |
| 2003/0196655 | A1* | 10/2003 | Ging | ................. A61M 16/0066 128/201.22 |
| 2003/0196656 | A1 | 10/2003 | Moore et al. | |
| 2004/0226566 | A1* | 11/2004 | Gunaratnam | ..... A61M 16/0825 128/207.18 |
| 2007/0125385 | A1* | 6/2007 | Ho | ................... A61M 16/0666 128/206.26 |
| 2009/0032026 | A1* | 2/2009 | Price | ................. A61M 16/0622 128/207.11 |
| 2010/0006101 | A1 | 1/2010 | McAuley et al. | |
| 2010/0192957 | A1* | 8/2010 | Hobson | ............. A61M 16/0069 128/207.18 |
| 2011/0067704 | A1 | 3/2011 | Kooij et al. | |
| 2012/0067349 | A1* | 3/2012 | Barlow | ............. A61M 16/0633 128/205.25 |
| 2012/0222680 | A1* | 9/2012 | Eves | ................. A61M 16/0875 128/206.24 |
| 2012/0318270 | A1* | 12/2012 | McAuley | ............... A61M 16/16 128/205.25 |
| 2013/0152937 | A1* | 6/2013 | Jablonski | .......... A61M 16/0605 128/205.25 |
| 2014/0137870 | A1* | 5/2014 | Barlow | ............... A61M 16/024 128/205.25 |
| 2014/0150798 | A1 | 6/2014 | Fong et al. | |
| 2015/0059762 | A1 | 3/2015 | Schulz et al. | |
| 2015/0128954 | A1 | 5/2015 | Smith et al. | |
| 2015/0246198 | A1 | 9/2015 | Bearne et al. | |
| 2015/0246200 | A1* | 9/2015 | Neff, Jr. | ............ A61M 16/0816 128/202.27 |
| 2015/0283347 | A1 | 10/2015 | Barlow | |
| 2015/0352306 | A1* | 12/2015 | Scheiner | ........... A61M 16/0875 128/205.25 |
| 2016/0008564 | A1* | 1/2016 | Grashow | ........... A61M 16/0816 128/206.21 |
| 2016/0074614 | A1 | 3/2016 | Huddart et al. | |
| 2016/0143766 | A1* | 5/2016 | Krishnasamy | ........ A61F 5/3707 128/97.1 |
| 2016/0144146 | A1 | 5/2016 | Huddart et al. | |
| 2016/0296720 | A1* | 10/2016 | Henry | ............... A61M 16/0622 |

FOREIGN PATENT DOCUMENTS

| | | |
|---|---|---|
| WO | WO 2014/110626 | 7/2014 |
| WO | WO 2015/013761 | 2/2015 |
| WO | WO 2016/082001 | 6/2016 |

* cited by examiner

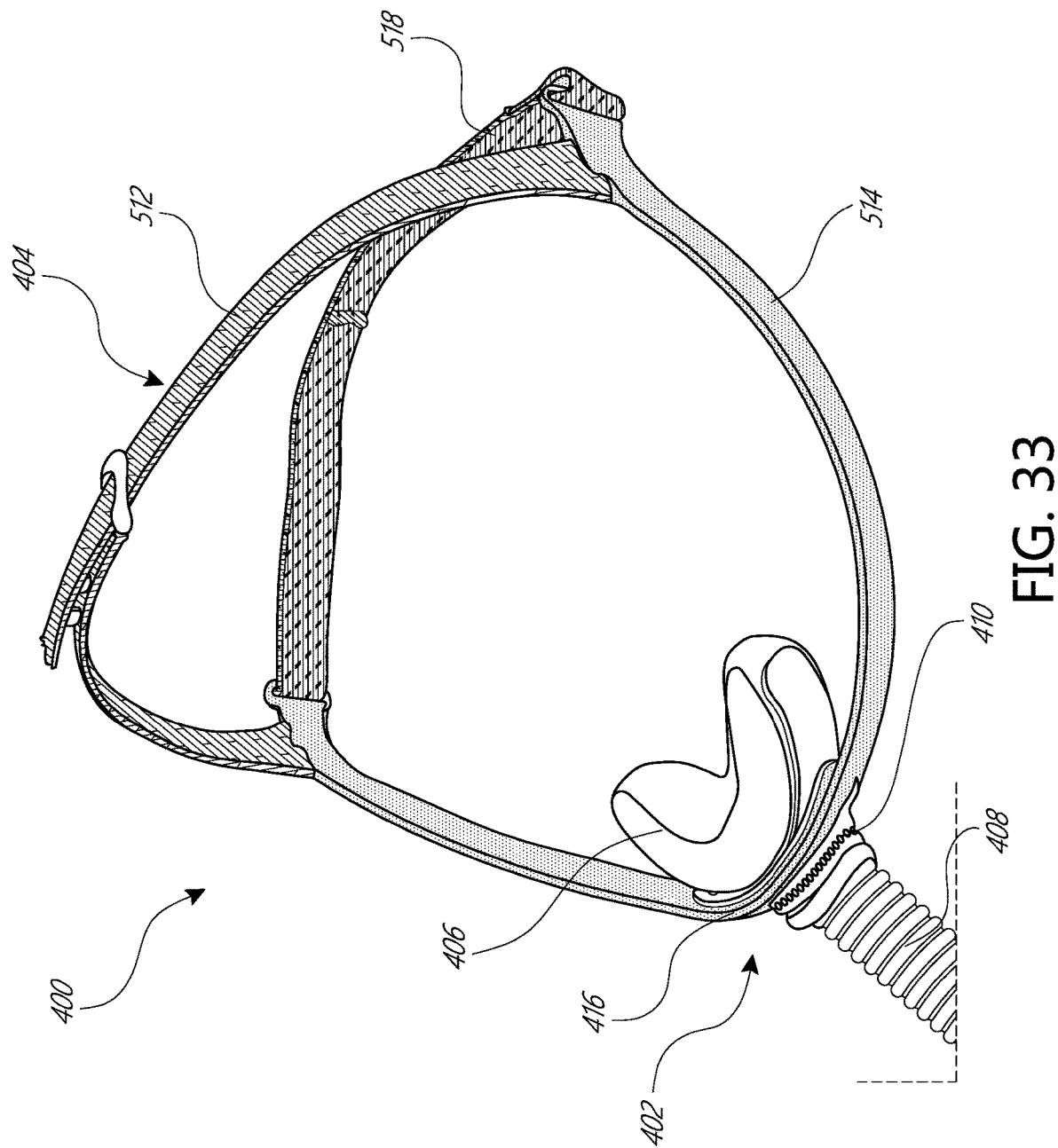

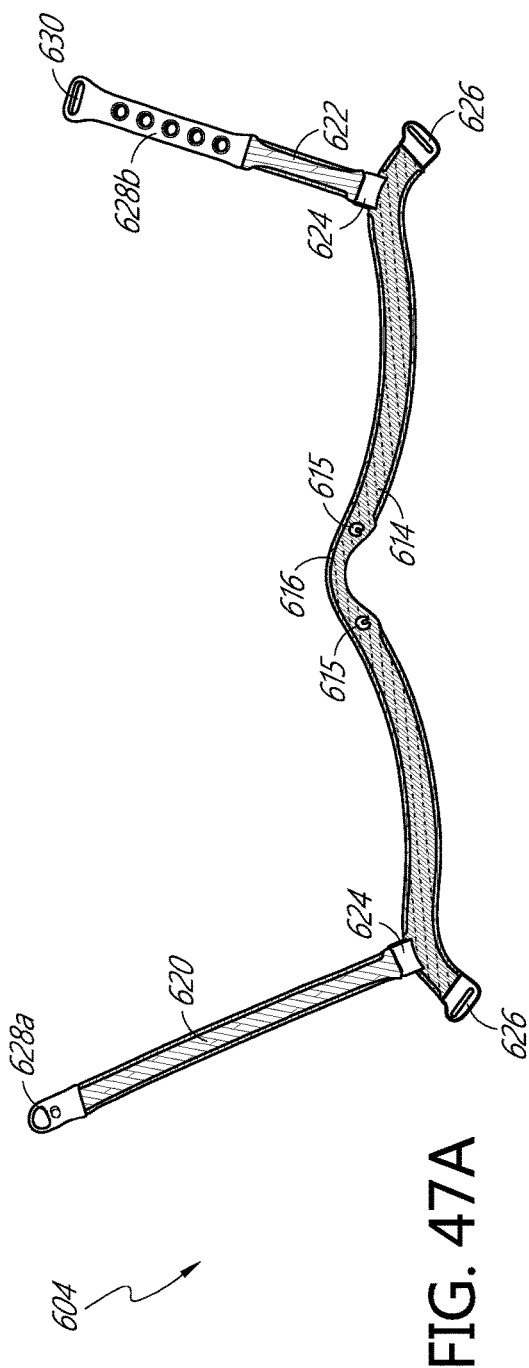
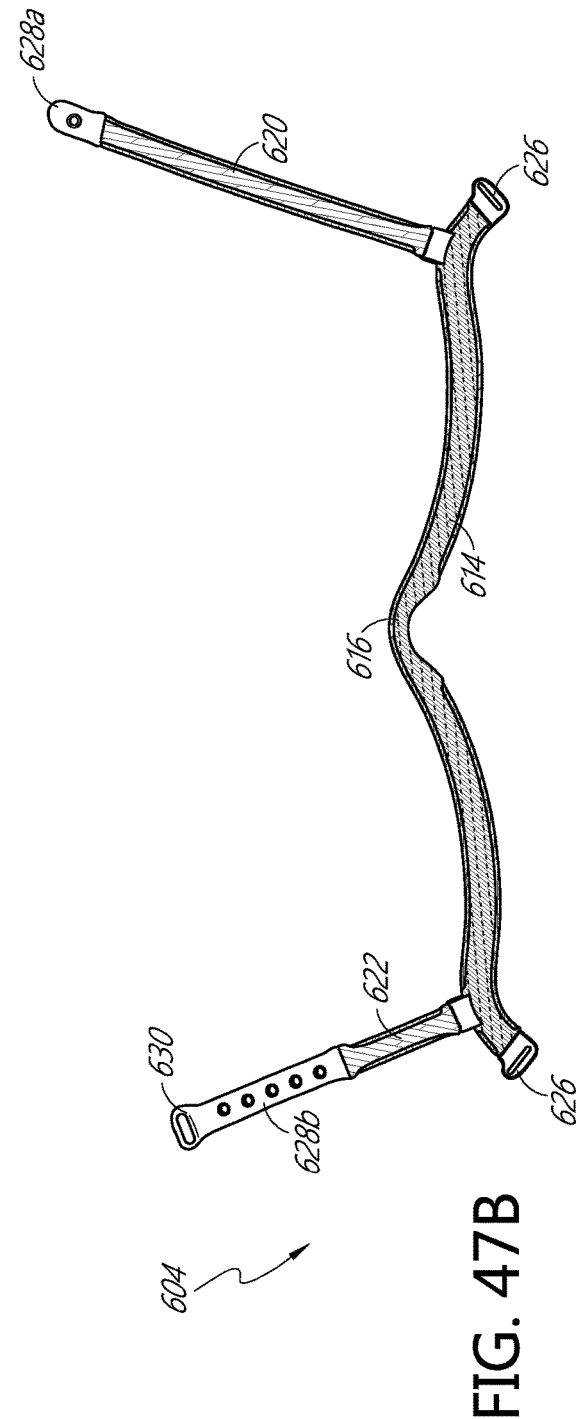
FIG. 47A
FIG. 47B

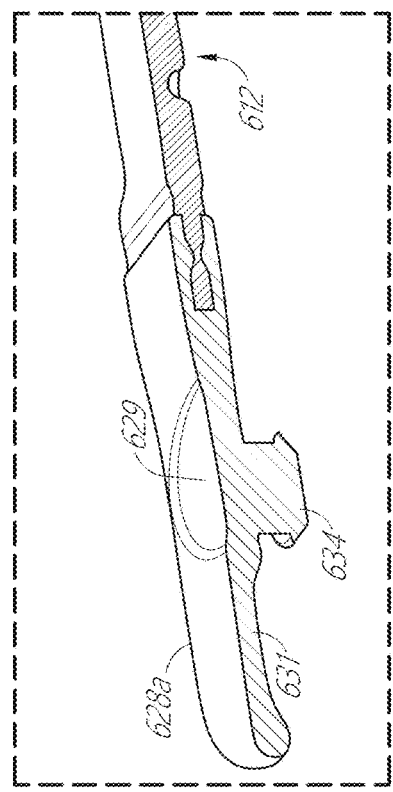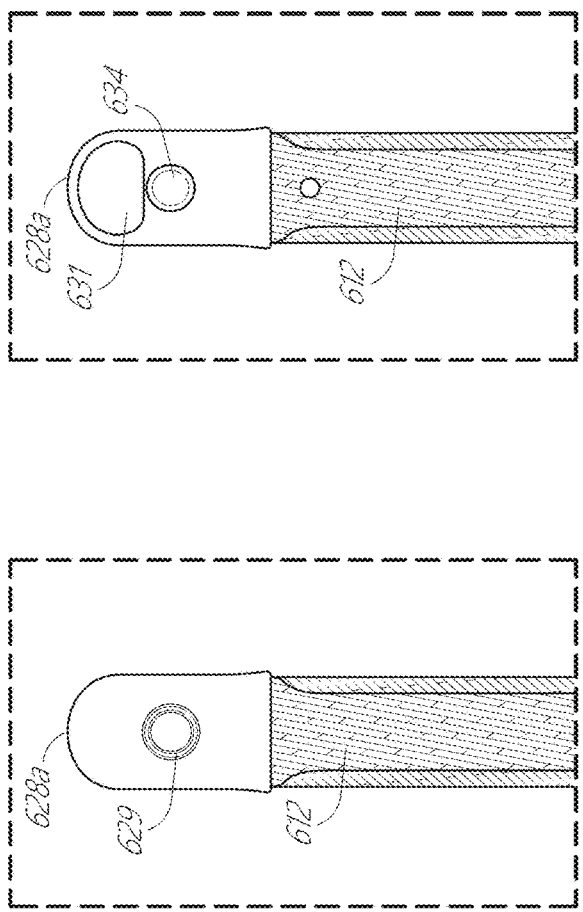

FRAME AND HEADGEAR FOR RESPIRATORY MASK SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), which is a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which secures the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that forms a substantially airtight seal in or around the patient's nose and/or mouth. Respiratory masks are available in a range of styles including full-face, nasal, direct nasal and oral masks, which create a substantially airtight seal with the nose and/or mouth. The seal or cushion is held in place on the patient's face by the headgear. In order to maintain a substantially airtight seal the headgear should provide support to the patient interface such that it is held in a stable position relative to the patient's face during use. Such respiratory masks may also be used to deliver NIV and other therapies.

BRIEF SUMMARY

In a first aspect, an embodiment of the invention may broadly be said to comprise a headgear for a respiratory mask comprising an integrally formed closed loop. The closed loop comprises a yoke, a pair of side arms, and a top strap. The yoke is configured to connect to a patient interface. The pair of side arms are each configured to extend from a lateral rearward portion of the yoke, and in use, across a cheek and above an ear of a user. The top strap is configured to extend between the pair of side arms, and in use, across the top of the user's head.

Preferably the top strap comprises separate left and right portions, each having a free end and a fixed end. The fixed end of the left portion is integrally formed with one of the side arms and the fixed end of the right portion is integrally formed with the other side arm. The free ends of the left and right portions are adjustably connected to each other.

Preferably the closed loop is made of a semi-rigid material.

Preferably comprises a plastic material.

Preferably the side arms comprise an integrally formed buckle at a free end.

Preferably the headgear further comprising a rear strap configured to extend between the buckles of the side arms and, in use, around the rear of the user's head.

Preferably the rear strap comprises a pair of lateral ends that are each adjustably connected to the buckles of the side arms.

Preferably the rear strap is removably connected to the buckles.

Preferably the rear strap and top strap are configured, in use, to encircle a rear portion of a user's head.

In a second aspect, an embodiment of the invention may broadly be said to comprise a respiratory mask comprising a patient interface and a headgear as described above.

In a third aspect, an embodiment of the invention may broadly be said to comprise headgear for a respiratory mask comprising an integrally formed closed loop and a rear strap. The closed loop comprises a yoke, a pair of side arms and a top strap. The yoke is configured to connect to a patient interface. The side arms are each configured to extend from a lateral rearward portion of the yoke, and in use, across a cheek and above an ear of a user. In use, the top strap is configured to extend across the top of the user's head joining the pair of side arms. The rear strap is configured to extend between the pair of side arms around the rear of the user's head.

In a fourth aspect, an embodiment of the invention may broadly be said to comprise a headgear for a respiratory mask comprising a yoke, a pair of opposing side arms and a top strap. The yoke is configured to connect to a frame of the respiratory mask. The pair of opposing side arms is configured in use to extend from a pair of lateral rearward portions of the yoke, and in use, across the user's cheeks and above the top of the user's ears. The top strap is configured, in use, to extend between the side arms above the user's ears, over the top of the user's head. The yoke, side arms and top strap are integrally formed to provide a closed loop, which remains intact when the yoke is separated from the frame.

In some embodiments, a frame for a respiratory mask includes a body having an exterior surface and an interior surface. The exterior surface includes a yoke receiving structure configured to receive a yoke and an inlet collar defining and inlet. The yoke receiving structure can span the longitudinal distance of the body. The interior surface includes an outlet collar defining an outlet. A gas pathway is formed between the inlet and the outlet. The perimeter of the gas pathway at the inlet is less than the perimeter of the gas pathway at the outlet.

The inlet collar can include a portion of increasing perimeter. The inlet can have an oval shape. The outlet can have an oval shape. The outlet collar can include a truncated portion. A portion of the outlet collar can be longer than another portion of the outlet collar. The outlet collar can include a recessed portion extending partially around the outlet collar.

In some embodiments, a frame for a respiratory mask includes a body having an exterior surface and an interior surface. The exterior surface includes a yoke receiving structure configured to receive a yoke and an inlet collar defining an inlet. The yoke receiving structure can span the longitudinal distance of the body. The inlet collar includes a transition portion of increasing perimeter. The interior surface includes an outlet collar defining an outlet. A gas pathway is formed between the inlet and the outlet. The inlet collar includes a vent that allows the passage of gas from the gas pathway to an exterior of the frame.

The inlet collar can include a first portion of a first perimeter, and a second portion of a second perimeter coaxially offset from said first portion. The first portion and second portion can be separated by the transition portion of increasing perimeter, and the transition portion can link the first and second portions. The second perimeter can be greater than the first perimeter. The second portion can be located adjacent to the exterior surface of the frame. The transition portion can include the vent. The vent can include a plurality of holes.

In some embodiments, a frame for a respiratory mask includes a body having an exterior surface and an interior surface. The exterior surface includes a yoke receiving structure configured to receive a yoke and an inlet collar defining an inlet. The yoke receiving structure can be defined between a first retaining ridge and a second retaining ridge vertically displaced from the first retaining ridge forming a recessed channel configured to receive a yoke. The interior surface can include an outlet collar defining an outlet. A gas pathway can be formed between the inlet and the outlet.

In some embodiments, a frame for a respiratory mask includes a body, an inlet collar, and an outlet collar. The body has an exterior surface and an interior surface and extends from a first lateral edge to a second lateral edge. The inlet collar extends from the exterior surface, defines an aperture, and is configured to be coupled to a gas conduit in use. The outlet collar extends from the interior surface. The body comprises a first headgear retaining feature positioned laterally at least partially between the inlet collar and the first lateral edge and a second headgear retaining feature positioned laterally at least partially between the inlet collar and the second lateral edge.

The frame and headgear retaining features can be configured such that the first headgear retaining feature can be engaged with a corresponding first frame retaining feature on a headgear and then the frame and headgear can be rotated relative to each other about the headgear retaining feature to align the second headgear retaining feature with a corresponding second frame retaining feature on the headgear. The centers of the first and second headgear retaining features can be vertically displaced relative to a central axis extending through the aperture of the inlet collar. The first and second headgear retaining features can be circular holes.

In some embodiments, a frame for a respiratory mask includes a body having an exterior surface and an interior surface and extending from a first lateral edge to a second lateral edge; an aperture configured to receive gases from a gas delivery conduit in use; and a plurality of bias flow holes disposed about a portion of the frame surrounding the aperture and forming an arc extending approximately 240°.

The bias flow holes can extend from approximately 4:00 to approximately 8:00 (as on a clock). The frame can further include an inlet collar extending from the exterior surface, the inlet collar comprising a wall defining the aperture and configured to be coupled to a gas conduit in use, the inlet collar comprising the plurality of bias flow holes extending through the wall. The inlet collar can have an oval cross-section. The wall of the inlet collar can angle inwardly at an inlet collar surface angle relative to an axis extending through the aperture as the wall extends away from the frame body. The inlet collar surface angle can vary about a periphery of the inlet collar.

In some embodiments, a frame for a respiratory mask includes a body having an exterior distal-facing surface and an interior proximal-facing surface; and an inlet collar extending distally from the exterior surface to a distal rim, the inlet collar comprising a wall defining an aperture and configured to be coupled to a gas conduit in use, wherein a top and bottom of the distal rim project distally relative to lateral sides of the distal rim. The inlet collar can have an oval cross-sectional shape.

In some embodiments, a headgear for a respiratory mask includes a yoke configured to connect to a patient interface, first and second side arms, a top strap, and at least one connector configured to connect to a frame in use. Each of the first and second side arms extends from a lateral rearward portion of the yoke and is configured to extend across a cheek and above an ear of a user in use. The top strap is coupled to and extends between the first and second side arms and is configured to extend across the top of the user's head in use. At least one of the yoke, first and second side arms, and top strap comprises a plastic core and a textile outer casing at least partially surrounding the plastic core, wherein the at least one of the yoke, first and second side arms, and top strap is formed by intra-molding, and wherein the at least one connector is formed by a burst-through process such that the at least one connector is integrally formed with the plastic core and extends outside of the outer casing.

The connector can include a channel separating two retaining portions. The connector can be generally circular. The headgear can include two connectors, each configured to engage a corresponding headgear retaining feature on a frame, wherein the headgear and connectors are configured such that a first of the two connectors can be engaged with a corresponding first headgear retaining feature on the frame and then the frame and headgear can be rotated relative to each other about the connector to align a second of the two connectors with a corresponding second headgear retaining feature on the frame.

In some embodiments, a headgear for a respiratory mask includes a yoke configured to connect to a patient interface, first and second side arms, and a top strap. Each of the first and second side arms extends from a lateral rearward portion of the yoke and is configured to extend across a cheek and above an ear of a user in use. The top strap is coupled to and extends between the first and second side arms and is configured to extend across the top of the user's head in use. The top strap includes a first portion coupled to the first side arm, a second portion coupled to the second side arm, and an adjustment mechanism configured to couple and allow for adjustment between the first and second portions. The adjustment mechanism includes a guide loop at a free end of the second portion; a plurality of holes along a length of the second portion proximate the free end; a projection extending from an inner surface of the first portion, the inner surface configured to face and at least partially overlie the second portion when the first and second portions are coupled in use, wherein the projection is configured to engage any one of the plurality of holes to secure the first and second portions together; and a plurality of location guides extending along a length of the first portion proximate the projection, the location guides comprising a series of protruding edges having a width greater than a diameter of an aperture defined by the guide loop. In use, the first portion is configured to be advanced and/or withdrawn through the guide loop, and contact between the protruding edges and guide loop provides a resistive force to movement of the first portion through the guide loop.

The top strap can include a plastic core and a textile outer casing at least partially surrounding the plastic core, wherein the second portion comprises a surrounding channel extending around at least one of the plurality of holes and wherein the outer casing does not surround the surrounding channel. The projection can include a post extending from and adjacent the inner surface of the first portion and an enlarged head at an end of the post, the enlarged head having a larger diameter than a diameter of the post.

In some embodiments, a headgear for a respiratory mask includes a strap including a yoke portion and first and second side arms, and a top strap. The yoke portion is configured to connect to a patient interface. Each of the first and second side arms extends from a lateral rearward portion of the yoke portion and is configured to extend across a cheek and above an ear of a user in use. The yoke portion and the first and second side arms can be integrally formed. The top strap is coupled to and extends between the first and second side arms and is configured to extend across the top of the user's head in use. A first edge of the strap comprises a soft edge and a second, opposite edge of the strap comprises a soft edge portion and a rigid edge portion.

A thickness of the soft edge of the first edge can vary between a maximum thickness at a lateral end of the side arms and a minimum thickness proximate a central point of the yoke portion. A thickness of the soft edge portion of the second edge can vary between a maximum thickness at a lateral end of the side arms and a minimum thickness at a point laterally spaced from a center of the yoke portion.

In some embodiments, a headgear for a respiratory mask includes a front strap and a top strap. The front strap includes a yoke configured to connect to a patient interface and first and second side arm portions, each of the first and second side arm portions extending from a lateral end of the yoke and configured to extend across a cheek and above an ear of a user in use. The top strap is coupled to and extends between the first and second side arm portions and is configured to extend across the top of the user's head in use. The top strap includes a first portion coupled to the first side arm portion, a second portion coupled to the second side arm portion, and an adjustment mechanism configured to couple and allow for adjustment between the first and second portions. At least one of the yoke, first and second side arm portions, and top strap comprising a plastic core and a textile outer casing at least partially surrounding the plastic core. In some embodiments the at least one of the yoke, first and second side arm portions, and top strap may be formed by intra-molding.

The adjustment mechanism can include a first inter-engaging portion, such as a female connector at a free end of the second portion and a second inter-engaging portion, such as a male connector at a free end of the first portion, wherein in use, the first and second inter-engaging portions are configured to be selectively engaged in one of a plurality of discrete configurations to set a length of the top strap. The first inter-engaging portion may comprise a female connector comprising a plurality of holes along a length of the female connector. The second portion may further comprise a guide loop and in use, the first portion is configured to be advanced and/or withdrawn through the guide loop. The second inter-engaging portion may comprise a male connector comprising a projection extending from an inner surface of the male connector. At least a portion of the second inter-engaging portion may be configured to overlie at least a portion of the first inter-engaging portion when coupled and the projection may be configured to engage any one of the plurality of holes to secure the first and second portions together. The male connector may comprise a grip on or in an outer surface of the male connector. The male connector may comprise a grip on or in the inner surface of the male connector. The first portion of the top strap may be coupled to the first side arm portion via an over-molded joint and the second portion of the top strap may be coupled to the second side arm portion via an over-molded joint. The headgear may further comprise a buckle at a lateral end of each of the first and second side arm portions, the buckles configured to receive a rear strap. The buckles may be over-molded onto the lateral ends of the first and second side arm portions. The yoke may comprise two frame retaining features, each configured to engage a corresponding headgear retaining feature on a frame. The frame retaining features may be horse-shoe shaped. The front strap may comprise a pad surrounding and extending laterally outward from each of the frame retaining features, the pads having a greater thickness than a remainder of the front strap. In some embodiments the female connector may comprise a guide loop and a plurality of holes along a length of the female connector, and the male connector may comprise a projection extending from an inner surface of the male connector, the inner surface configured to face and at least partially overlie the female connector when the first and second portions are coupled in use, wherein the projection is configured to engage any one of the plurality of holes to secure the first and second portions together. In use, the first portion is configured to be advanced and/or withdrawn through the guide loop.

The female connector can be over-molded onto the second portion. The male connector can be over-molded onto the first portion. The male connector can include a grip on or in an outer surface of the male connector. The male connector can include a grip on or in the inner surface of the male connector. The first portion of the top strap can be coupled to the first side arm portion via an over-molded joint. The second portion of the top strap can be coupled to the second side arm portion via an over-molded joint. The headgear can further include a buckle at a lateral end of each of the first and second side arm portions, each of the buckles configured to receive an end of a rear strap. The buckles can be over-molded onto lateral ends of the first and second side arm portions. The yoke can include two frame retaining features, each configured to engage a corresponding headgear retaining feature on a frame. The frame retaining features can be horse-shoe shaped. The front strap can include a pad surrounding and extending laterally outward from each of the frame retaining features, the pads having a greater thickness than a remainder of the front strap.

Further aspects of the invention, which should be considered in all its novel aspects, will become apparent from the following description.

BRIEF DESCRIPTION OF THE DRAWINGS

A number of embodiments will now be described by way of example with reference to the drawings in which:

FIG. 33 is a perspective view of a non-limiting exemplary embodiment of a respiratory mask according to the present disclosure.

FIG. 47A is a rear or internal view of a disconnected and expanded portion of the headgear of FIG. 46.

FIG. 47B is a front or external view of the portion of the headgear of FIG. 47A.

FIG. 50A is a front or external view of a male connector of the headgear of FIGS. 46 and 47A.

FIG. 50B is a rear or internal view of the male connector of FIG. 50A.

FIG. 50C is a perspective section view of a variation of the male connector of FIG. 50A.

DETAILED DESCRIPTION

Figure 1:
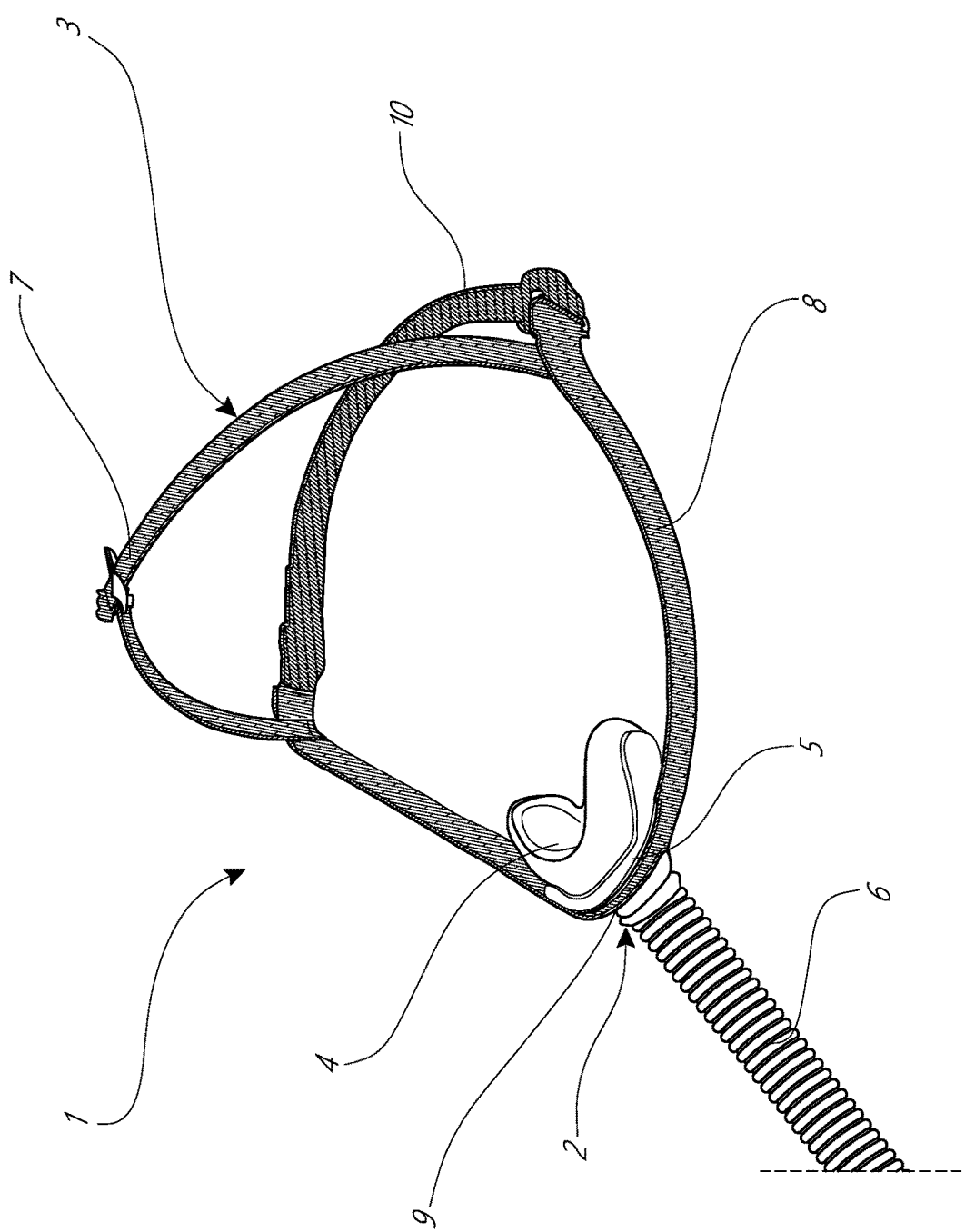
FIG. 1 is a perspective view of a first non-limiting exemplary embodiment of a respiratory mask according to the present disclosure.

The present disclosure relates to a frame and headgear for a respiratory mask system configured to deliver a respiratory therapy to a patient/user. FIG. 1 shows a non-limiting exemplary embodiment of a respiratory mask system 1 of the present disclosure. The respiratory mask system 1 comprises a patient interface 2 and headgear 3. The patient interface 2 comprises a seal 4, frame 5 and gas delivery conduit 6.

The patient interface 2 is configured to provide an air path through which a supply of pressurized air can be provided to the airway of a user. In the embodiments shown and detailed below the patient interface 2 is a nasal mask, in particular an under-nose or sub-nasal mask, having a seal 4 that is configured to seal on the lower surfaces of a patient's/user's nose. The seal 4 is configured to form an airtight seal under the nose of the patient/user, along a portion of the face extending lateral to the nose, as well as along the upper lip of the user.

In some embodiments the seal 4 may be adapted to extend around and seal over the wing or alar of the nose, which flares out to form a rounded eminence around the nostril. The illustrated mask 1 is adapted to seal around the surfaces that define the opening to the nostril, which may include a portion or entirety of the fleshy external end of the nasal septum, sometimes called the columella. In some configurations, the seal 4 is adapted to extend upwardly to seal along at least a portion of the left and right dorsal side walls of the nose of the user. In some configurations, the seal 4 is adapted to extend upwardly along at least a portion of the left and right dorsal side walls without extending upwardly to the region of the bridge of the nose of the user. In some configurations, a primary sealing surface of the seal 4 contacts the underside of the nose of the user, the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries.

In the illustrated configuration, the seal 4 does not extend over the bridge of the nose of the user. More particularly, the illustrated seal 4 does not contact the bridge of the nose of the user. This is advantageous as contact and thus pressure applied to the nasal bridge can result in pressure sores and discomfort for the user. If the seal causes pain or discomfort to the user they may not be compliant with the therapy.

An under-nose or sub-nasal mask with a seal 4, as described above, may be less stable on the user's face than more traditional masks that contact the nasal bridge as a result of having a reduced contact area with the users face. The reduced contact area provides fewer constraints as to how the seal 4 can move relative to a user's face, and therefore the seal 4 may be able to roll or rotate relative to the user's face. Any rolling or rotation of the seal 4 may result in a substantially airtight seal between the seal 4 and the user's face being broken and the delivery of the respiratory therapy compromised. In some embodiments instability of the seal 4 may be lessened by providing a headgear 3 capable of transferring forces away from the seal 4 to other parts of the users' head.

The frame 5 is configured to provide a manifold that connects the components of the patient interface 2 together and secures them to the headgear 3. The frame 5 can comprise features that are configured to fluidly connect the gas delivery conduit 6 to the seal 4, such that a continuous air path is provided.

The headgear 3 is configured, in use, to secure the patient interface 2 to a user's face. The headgear 3 comprises a top strap 7, pair of side arms 8 and a yoke 9, which are permanently joined to form a closed loop. In use, the top strap 7 is configured to pass over the top of a user's head, the side arms are configured to extend across the cheeks of the user and the yoke 9 is configured to connect to the frame 5. The headgear 3 further comprises a rear strap 10 that is adjustably connected to the side arms 8 and is configured, in use to pass around the rear of the user's head.

It is to be understood that while the headgear 3 and frame 5 of the present disclosure is described as being used in combination with a sub-nasal mask, it could be used in combination with any other type of mask, including but not limited to nasal prong or pillow masks, full-face masks that seal above and/or below the nasal bridge, or nasal masks.

Frame

Figure 2:
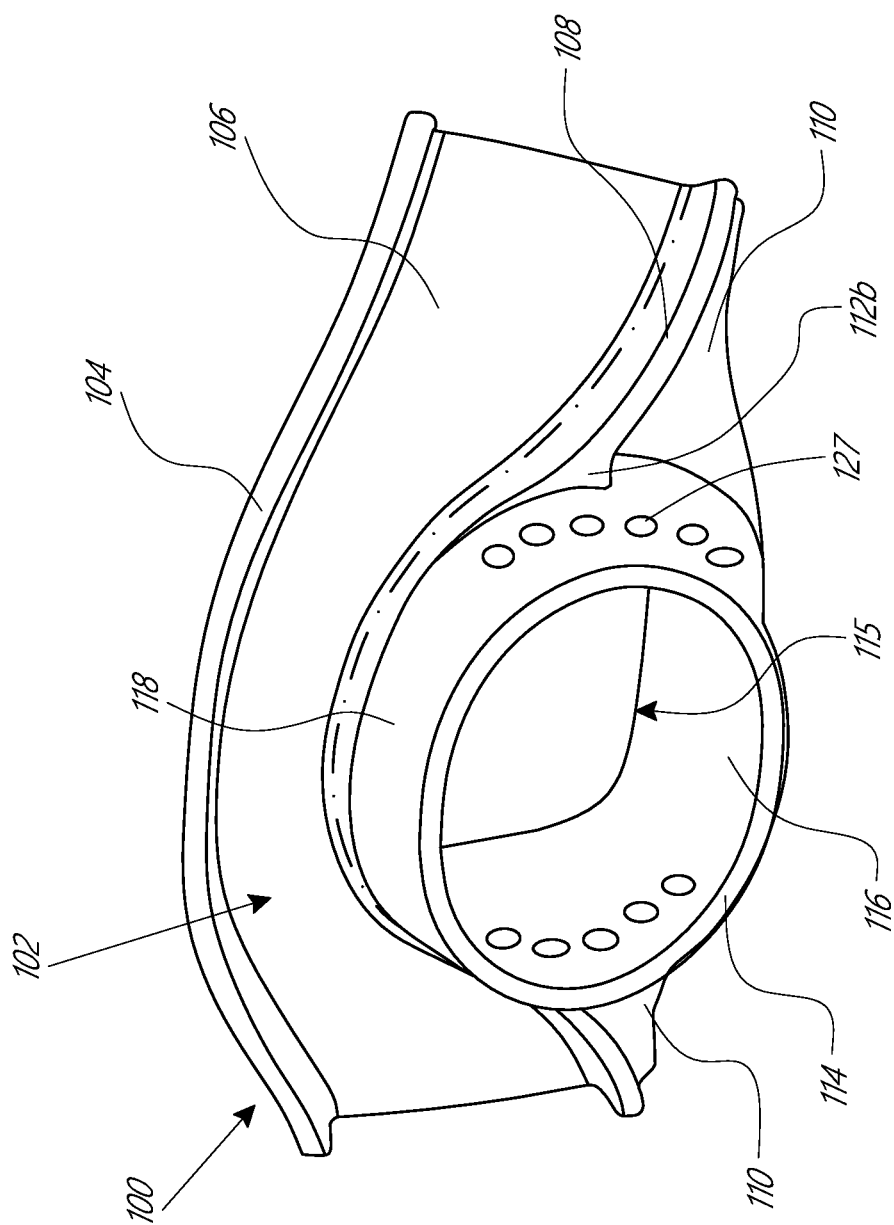
FIG. 2 is a front perspective view of a frame of the respiratory mask of FIG. 1.
Figure 3:
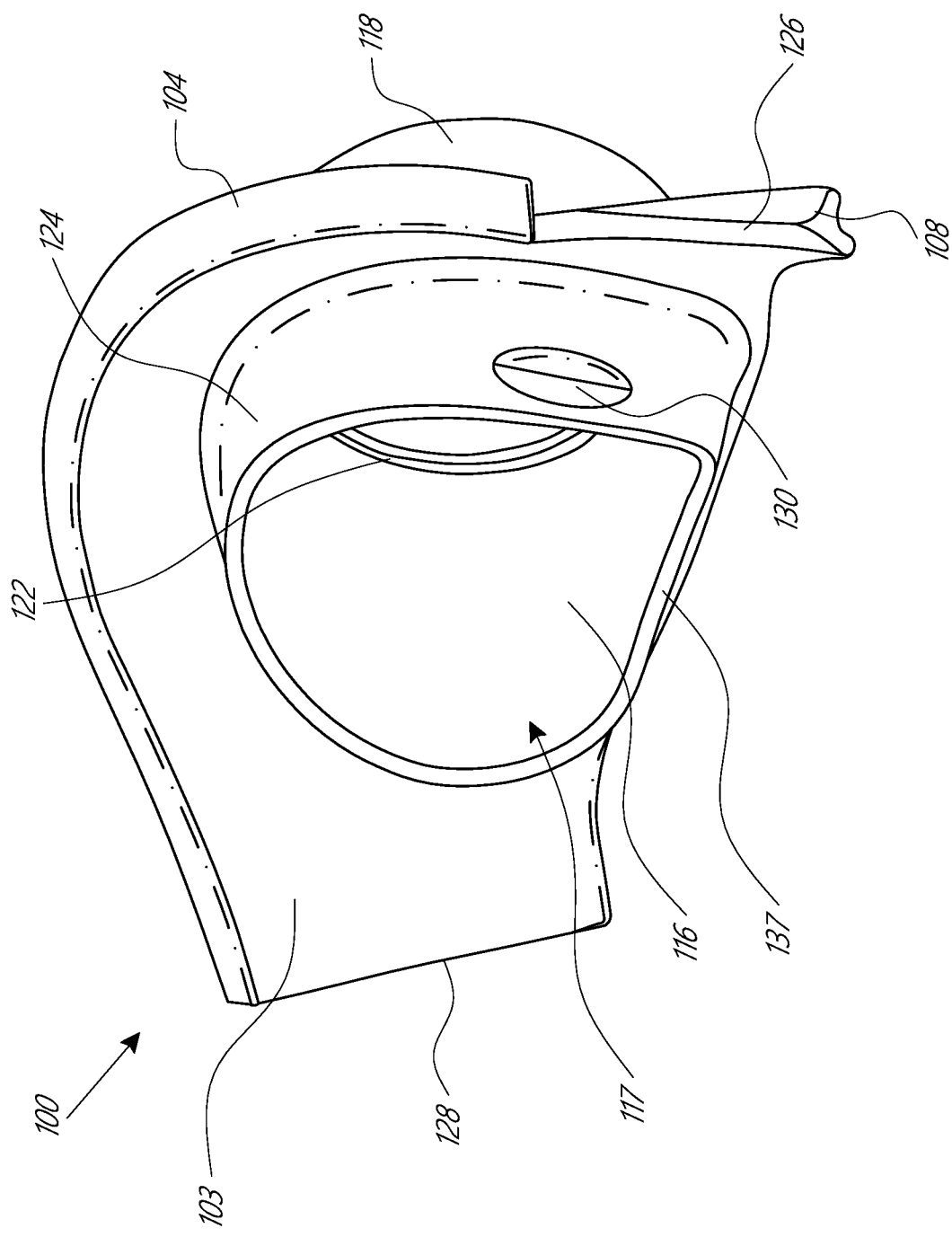
FIG. 3 is a rear perspective view of the frame of FIG. 2.

FIGS. 2 and 3 show perspective views of a first non-limiting exemplary embodiment of a frame 100 that is substantially similar to the frame 5 of FIG. 1, and forms part of a respiratory mask system. A vertical axis 105 and a lateral axis 107 (shown in FIG. 4) are defined with an origin at the central point of an inlet collar 114 of the frame 100. The frame 100 is symmetric about the vertical axis 105. The frame 100 has an exterior surface 102 and an interior surface 103. The exterior surface 102 acts as an interface between the frame 100, a headgear 3 and a gas delivery conduit 6. The exterior surface 102 includes a recessed channel 106. The recessed channel is defined by and lies between a first retaining ridge 104 and a second retaining ridge 108. The first retaining ridge 104 is vertically displaced from the second retaining ridge 108, the space between the first retaining ridge 104 and the second retaining ridge 108 defining the recessed channel 106. A recessed surface 110 is located adjacent to the second retaining ridge 108. A yoke 9 is inserted into the recessed channel 106, in use. The headgear 3 is connected to the frame 100 by inserting the yoke 9 into the recessed channel.

The exterior surface 102 additionally includes an inlet collar 114. The inlet collar 114 includes a centrally located inlet collar aperture 115. The inlet collar 114 also includes a collar interior surface 116 and an inlet collar surface 118. The inlet collar 114 can further include a conduit retaining projection 122, a number of seal retaining recesses 130, and/or a number of vent holes 127. The first retaining ridge 104 extends from a first lateral edge 126 to a second lateral edge 128 of the frame 100. The second retaining ridge 108 extends from the first lateral edge 126 to meet the inlet collar surface 118 of the inlet collar 114 at a laterally displaced junction 112a. The second retaining ridge 108 diverges from the inlet collar 114 at a second laterally displaced junction 112b and extends to the second lateral edge 128.

The interior surface 103 may contact the seal 206 or a clip connected to the seal 206 and spans from the first lateral edge 126 to the second lateral edge 128 of the frame 100. The interior surface 103 includes an outlet collar 137 that extends proximally from the frame 100 with respect to a user, establishing an outlet collar aperture 117. In the illustrated embodiment, a number of seal retaining recesses 130 are located on an outlet collar surface 124 to enable interaction between the frame 100 and a seal 206.

Figure 4:
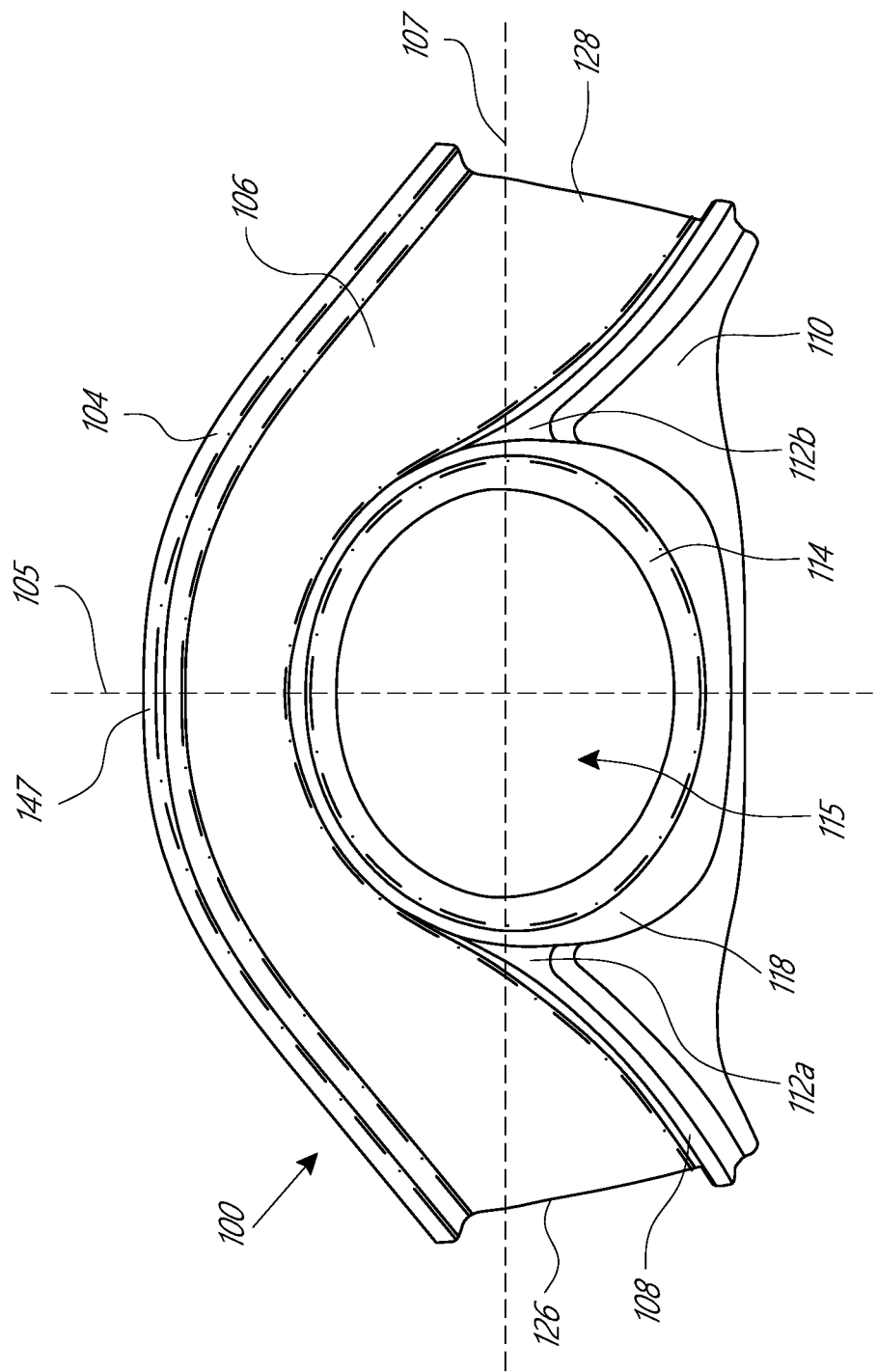
FIG. 4 is a front view of the frame of FIG. 2.
Figure 4A:
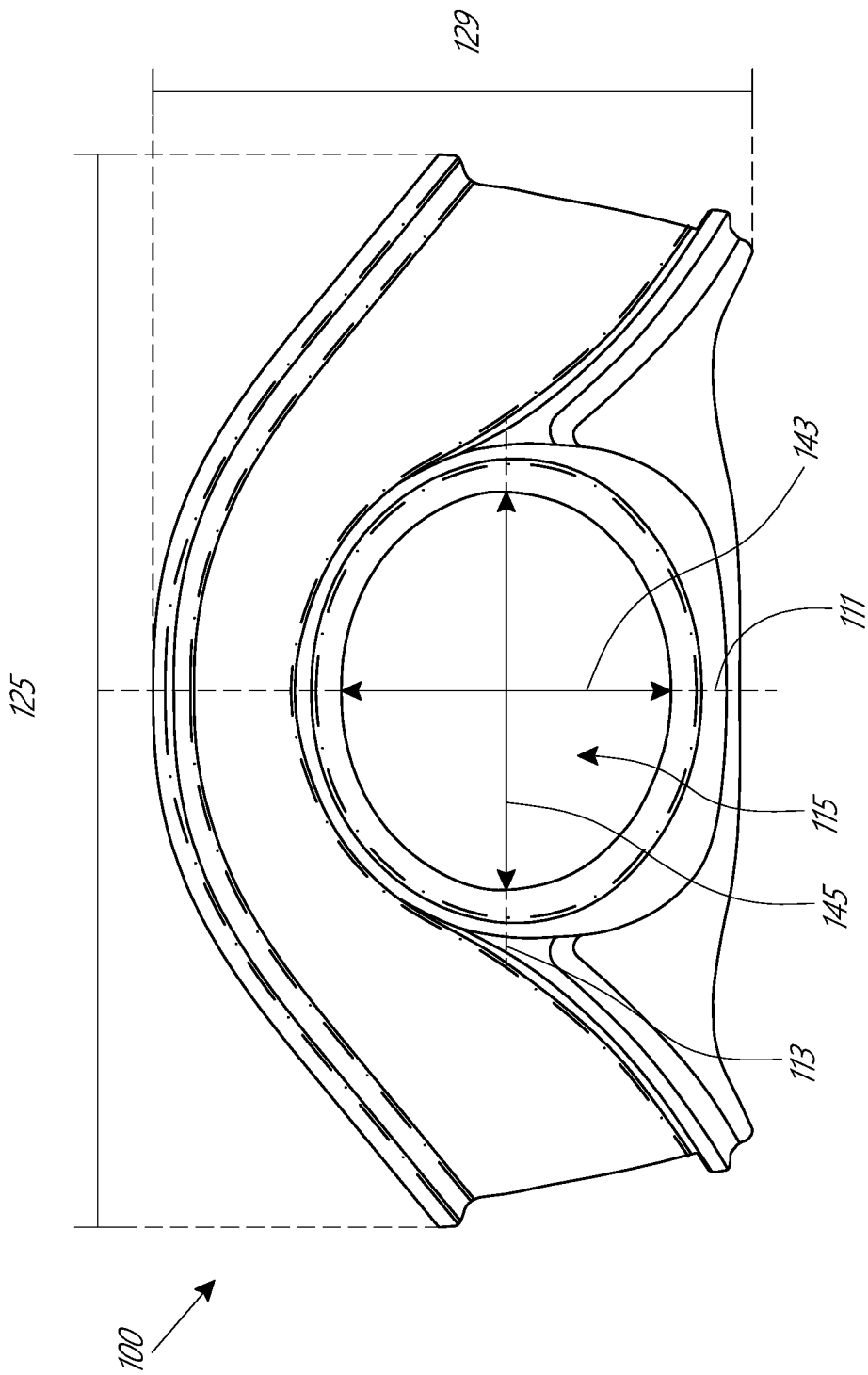
FIG. 4A is a front view of the frame of FIG. 2.

FIGS. 4 and 4A show a front view of the frame 100 aligned with the inlet collar aperture 115, i.e. a front view of the frame 100. The frame 100 acts as a manifold that connects multiple components of the respiratory mask system together. The inlet collar aperture 115 is an oval with a major axis 113 and a minor axis 111. In alternate embodiments, the inlet collar 114 may be circular, triangular or follow the profile of any other polygon desired.

The frame 100 is symmetric about the minor axis 111 of the inlet collar 114. In the illustrated configuration, the minor axis 111 is aligned with the vertical axis 105. In the illustrated configuration the inlet collar aperture 115 is positioned substantially in the center of the frame 100. The inlet collar aperture 115 has a major dimension 145 (e.g., length along its major axis 113) and a minor dimension 143 (e.g., length along its minor axis 111). Additionally, in the illustrated configuration, the major dimension 145 of the inlet collar aperture 115 is 20.7 mm and the minor dimension 143 of the inlet collar aperture 115 is 17.2 mm. Another way of expressing this is the ratio between the major dimension 145 and the minor dimension 143 of the inlet collar aperture 115 is approximately 1.2:1.

This ratio is, at least to an extent, dictated by the physical characteristics or shape of the gas delivery conduit used in the respiratory mask system. Furthermore, the desire to minimize the pressure drop that exists between a pressure generating device and the user also influences the possible range of ratios between the major dimension 145 and minor dimension 143. Pressure drop is a phenomenon known to occur in respiratory mask systems where a reduction in pressure occurs between the pressure generating device and the outlet of the respiratory mask system. The pressure drop is largely due to flow resistances and inefficiencies within the system. Minimizing the pressure drop observed in a respiratory mask system improves the efficacy of the therapy delivered to the user.

The pressure drop that one may measure across the respiratory mask system is increased with an increasing ratio between the major dimension 145 and the minor dimension 143 of the inlet collar aperture 115. Increasing the ratio of the major dimension 145 to the minor dimension 143 however, is beneficial as it enables the physical profile of the frame 100 to be reduced. This in turn enables a reduction in the overall profile of the respiratory mask system. Therefore, in other embodiments of frame 100, the ratio between the major dimension 145 and the minor dimension 143 of the inlet collar aperture 115 may vary from approximately 1:1 to approximately 2:1.

Referring again to FIG. 4, the recessed channel 106 spans from the first lateral edge 126 to the second lateral edge 128 of the frame 100. Like the recessed channel 106, the first retaining ridge 104 spans from the first lateral edge 126 to the second lateral edge 128 of the frame 100.

The lateral portions of the second retaining ridge 108 are substantially concave with respect to the lateral axis 107. The lateral portions of the second retaining ridge 108 are defined by an inflection region near junction 112 where the relative concavity deviates from concave to convex as the second retaining ridge 108 meets the inlet collar surface 118.

In the illustrated embodiment, the recessed channel 106 passes over the inlet collar 114. The recessed channel 116 is arcuate in shape and passing over the inlet collar 114. This is beneficial because the arcuate shape of the recessed channel 116 allows for effective force resolution of forces generated by the seal and headgear.

The first retaining ridge 104 and the second retaining ridge 108 project outwardly from the outer surface 102 of the frame in a direction toward the inlet collar 114. The inlet collar 114 includes a wall that extends from the outer surface 102. A vertical thickness or height or outward extension of the recessed channel 106 may be defined to be the displacement between a point on the first retaining ridge 104 that is adjacent to the recessed channel 106, and a corresponding point on the second retaining ridge 104 that is adjacent to the recessed channel 106, with each of the two points aligned on a common vertical axis. The points of maximum vertical thickness of the recessed channel 106 when defined in this way are at the first lateral edge 126 and second lateral edge 128 of the frame 100. The point of minimum vertical thickness of the recessed channel 106 is located on the vertical axis 105.

The vertical thickness or height of the recessed channel 106 decreases in magnitude when translating laterally from the first lateral edge 126 and the second lateral edge 128 inwards towards the vertical axis 105 of the frame 100. In the illustrated configuration, the minimum vertical thickness of the recessed channel 106 is approximately 5.8 mm and the maximum vertical thickness of the recessed channel 106 is approximately 12.7 mm. The ratio between the minimum vertical thickness and the maximum vertical thickness of the recessed channel 106 is therefore approximately 1:2.25. The vertical thickness of the recessed channel 106 corresponds with the thickness of the yoke 9 of the headgear 3 being used with the frame 100. In some configurations, the ratio between the minimum vertical thickness and the maximum vertical thickness of the recessed channel 106 may be between approximately 1:1 and 1:4.

Reducing the vertical thickness of the recessed channel 106, along a portion of the length or at least within a central location of the frame 100, enables the vertical profile of the frame 100 to be reduced or minimized. Reducing or minimizing the vertical profile of the frame 100 reduces both its real and perceived obtrusiveness and reduces or minimizes its mass, which is desirable for user comfort and may improve user compliance with the therapy. The reduced vertical thickness of the recessed channel 106 near the lateral center of the frame 100 may also provide an alignment feature between the yoke 9 and the recessed channel 106. The alignment feature may allow the yoke 9 to be connected to the frame 100 in only one orientation and thus prevent incorrect assembly of the headgear 3 to the frame 100.

The yoke 9 may be connected to the frame 100 via the recessed channel 106 through the use of any relevant means of connection. The yoke 9 may be bound to the recessed surface 106 through the use of an adhesive. In some configurations, the yoke 100 may be connected to the frame 100 using a snap fit mechanism, friction fit mechanism or a hook and loop fastening mechanism. In other configurations, the recessed surface may include one or more projections, designed to fit in a recess or hole in the yoke such that the combination of the projection and corresponding recess or hole mates the yoke to the frame. Alternately, the recessed surface 106 may include one or more recesses or holes such that one or more corresponding projections on the yoke mate the yoke to the frame.

Alternate configurations of the frame 100 may utilize a number of alternate recessed channel profiles. For instance, a recessed channel may extend either over the top of (as illustrated in FIGS. 4 and 4A), or underneath the inlet collar. In another alternative configuration the frame includes two or more recessed channels may extend laterally across the exterior surface of the frame. In some configurations, these recessed channels may include portions where the relevant retaining ridges are adjacent to each other, or where two recessed channels share a common retaining ridge. In some configurations, these recessed channels may not include adjacent portions. In some configurations, one or more recessed channels may both pass over the inlet collar. In some configurations, one or more recessed channels may both pass underneath the inlet collar.

In some configurations, two or more recessed channels may first diverge from a common recessed channel near one lateral edge, deviate around the inlet collar and then converge to a common recessed channel near the opposite lateral edge of the frame. In some configurations, multiple recessed channels may be entirely independent on the exterior surface of the frame. In other words, each of the independent recessed channels may have their own independent retaining ridges, or may share a common retaining ridge with another independent recessed channel, while maintaining completely separate channels themselves. In each of the aforementioned variations, one or more of the recessed channels may be used as an interface to connect the respiratory mask system's headgear 3 to the frame 100.

Referring again to FIG. 4, the recessed surface 110 spans from the first lateral edge 126, below the inlet collar 114, to the second lateral edge 128 of the frame 100. The recessed surface 110 is adjacent to the second retaining ridge 108 and the inlet collar 114 on the exterior surface 102 of the frame 100. In the illustrated configuration, the recessed surface 110 assists in providing support for the seal 206 and maintaining the structural integrity of the frame 100 both during the manufacturing process and during use. In alternative embodiments however, the frame 100 may be completely void of this recessed surface 110.

The lateral length 125 of the frame 100 according to the illustrated embodiment of FIG. 4A is approximately 56.00 mm. Accordingly, the ratio between the major dimension 145 of the inlet collar aperture 115 and the lateral length 125 of the frame 100 is approximately 1:2.70. The specified lateral length 125 of the frame 100 has been utilized to optimize the behavior of the frame 100 when combined with the seal 206 and headgear 3. The headgear 3 is desired to flex about the user's face to a relatively large extent. This behavior is desired to maximize the variance of facial profiles the respiratory mask system may accommodate. The frame 100 has a sufficient lateral length 125 that enables at least some headgear flex and reduces seal 206 displacement.

In alternative embodiments of the frame 100, the lateral length 125 may vary from approximately 45.00 mm to approximately 75.00 mm. The variation may be used to accommodate different seal 206 sizes, different profiles of headgear 3 or different headgear connection methods.

The vertical length 129 of the frame 100 has a vertical length that to provide adequate structure to enable the headgear 3 to connect effectively to the frame 100, and to provide the required structural and rotational integrity required by the seal 206.

In alternative embodiments of the frame, the vertical length of the frame may vary from approximately 25.00 mm to approximately 50.00 mm. The variation may be used to accommodate different seal sizes, different profiles of headgear 3 or different headgear connection methods.

Figure 5:
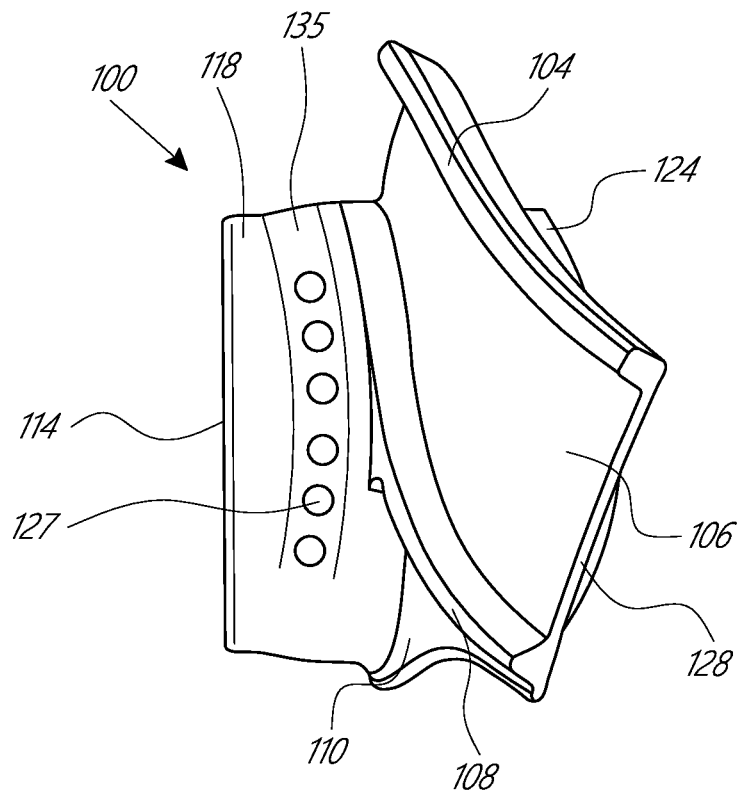
FIG. 5 is a left side view of the frame of FIG. 2.
Figure 5A:
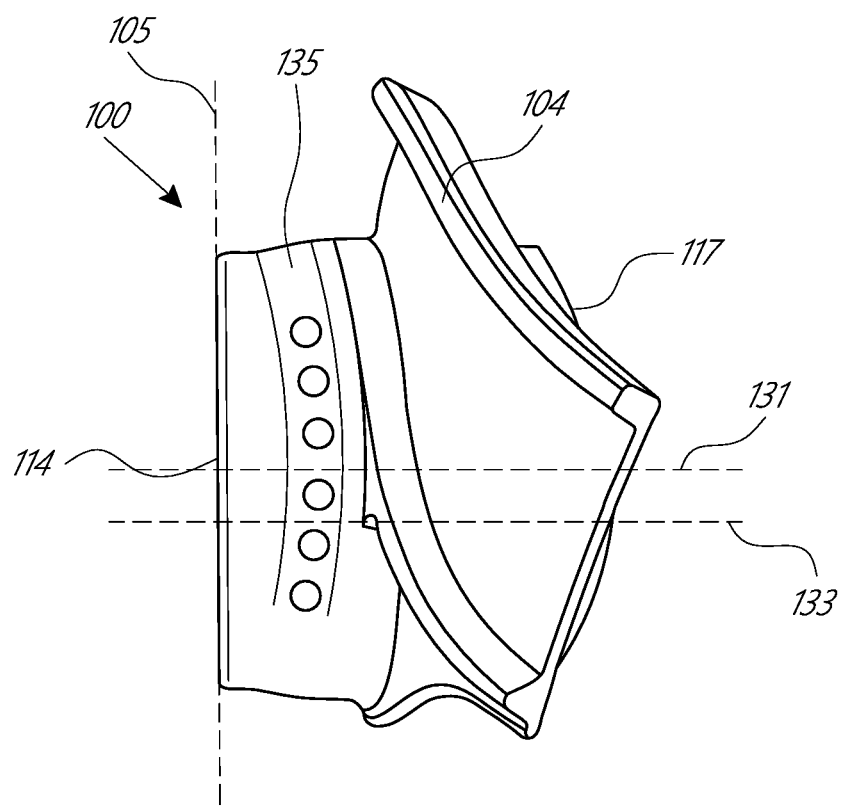
FIG. 5A is a left side view of the frame of FIG. 2.

FIGS. 5 and 5A show a left side view (with respect to the user) of the frame 100 illustrated in FIG. 1. The frame 100 is shown from one side of the frame. There is illustrated a vertical axis 105, an inlet proximal axis 131 and an outlet proximal axis 133. In the illustrated configuration, the inlet proximal axis 131 intersects the vertical axis 105 at a right angle, and is centrally located with respect to the inlet collar aperture 115. In other words, the inlet proximal axis 131, lateral axis 107 (see FIG. 4) and vertical axis 105 form a 3 dimensional space sharing a common origin. The inlet proximal axis 131 is approximately parallel to the flow of gas through the inlet collar aperture 115. The outlet proximal axis 133 intersects the vertical axis 105 at a right angle. In other words, the outlet proximal axis 133, secondary lateral axis 109 (shown in FIG. 6) and the vertical axis 105 share a common intersection point. The outlet proximal axis 133 is parallel to the flow of gas through the outlet collar aperture 117 of the frame 100. The inlet proximal axis 131 is vertically displaced with respect to the outlet proximal axis 133. In the illustrated configuration, the inlet proximal axis 131 is parallel to the outlet proximal axis 133. In alternate configurations, the outlet proximal axis 133 and the inlet proximal axis 131 may be aligned on the vertical axis 105.

The distal (with respect to the user) edge of the inlet collar 114 as viewed in FIG. 5A aligns with the vertical axis 105.

In alternate configurations, the edge of the inlet collar may be angled with respect to the vertical axis 105.

In the illustrated configuration, the inlet collar surface 118 includes a first portion that is of a first external perimeter, a second portion of a second external perimeter coaxially offset from the first portion, and a transition portion that is integral with, and links the first portion to the second portion. In the illustrated configuration, the external perimeter of the second portion is greater than that of the first portion and the second portion is proximally (when worn by a user) displaced with respect to the first. The difference in perimeter between the first portion and second portion of the inlet collar 114 produces the transition portion that forms an angled surface 135 that is angled with respect to the inlet proximal axis 131. This angled surface 135 facilitates the increase in perimeter. In some configurations, the inlet collar surface 118 will include only an angled surface. In other configurations, the inlet collar surface 118 may include a combination of angled surfaces and surfaces that aren't angled with respect to the inlet proximal axis 131.

As seen in the Figures the inlet collar 114 has a perimeter that is less than the perimeter of the outlet collar 137. The inlet collar 114 is of a different shape to the outlet collar 137.

The angled surface 135 spans the periphery of the inlet collar surface 118. A projection of the angled surface 135 on the inlet proximal axis 131 is of an approximately constant length at all points along the periphery of the inlet collar surface 118. The angled surface 135 is angled at approximately 10° with respect to the inlet proximal axis 131. The displacement between the angled surface 135 and the distal edge (with respect to the user) of the inlet collar surface 118 varies about the perimeter of the inlet collar surface 118. In the illustrated embodiment, the angled surface 135 includes a number of bias flow holes 127. In the configuration shown in FIGS. 4, 5A and 7, bias flow holes 127 are located on the angled surface 135, extending substantially around the angled surface 135. The bias flow holes expel bias flow substantially vertically with respect to the inlet proximal axis 131.

The inclusion of the angled surface 135 on the inlet collar surface 118 is intended to influence the orientation of the bias flow holes 127 in a beneficial manner. An issue encountered with perpendicularly oriented holes however (holes oriented at 90° to the inlet proximal axis 131) is the perception of an uncomfortable draft of air by the user when the respiratory mask system is in use. The bias flow holes 127 of the frame 100, when located on the angled surface 135, are therefore angled away from the user. As a result, when the frame 100 is in use, the flow of gas through the bias flow holes 127 is directed away from the user. This prevents the user from feeling an uncomfortable draft of air while the respiratory mask system is in use. Alternate embodiments of the frame 100 may include the angled surface 135 with a modified angle with respect to the inlet proximal axis 131. In some configurations, this angle may be between 0° and 20° or between 5° and 15°. In other configurations, this angle may be greater than 20°.

In other configurations, the bias flow holes may span around the entire angled surface. Alternately, a configuration of bias flow holes may be arranged on the inlet collar surface. This configuration may include one or more rows of bias flow holes, and rows may be aligned or offset with respect to each other. In other configurations, bias flow holes may be located anywhere else on the frame 100 in any desired configuration. Some configurations of the frame may include a single vent. Other configurations may include a single vent with a diffusor. The diffusor may be integral with the vent, or may connect to the frame 100 over the vent. The diffusor in such a configuration may act to diffuse the noise emanating from the vent when the respiratory mask system is operational.

Referring again to FIGS. 5 and 5A, the side profile of the recessed channel 106 is shown. The recessed channel 106 is seen to be concave in the lateral direction with respect to the user. The degree of concavity of the recessed channel 106 may vary along the lateral length of the frame 100. This is a result of the recessed channel 106 twisting along its length. The curvatures of the recessed channel 106 identified are such that the profile of the frame 100 may provide adequate structural support for the seal 206 of the respiratory mask system.

Figure 6:
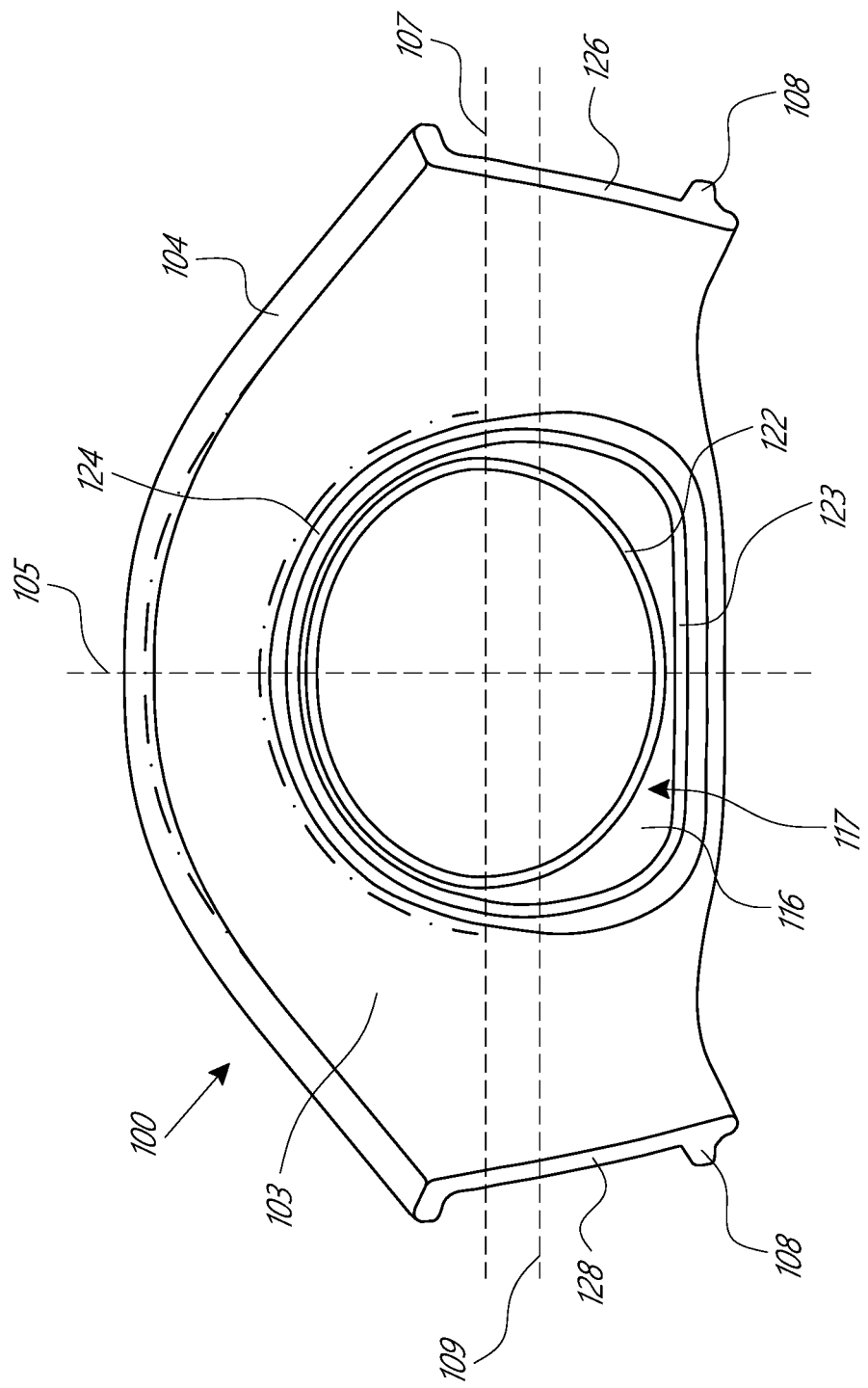
FIG. 6 is a rear view of the frame of FIG. 2.
Figure 6A:
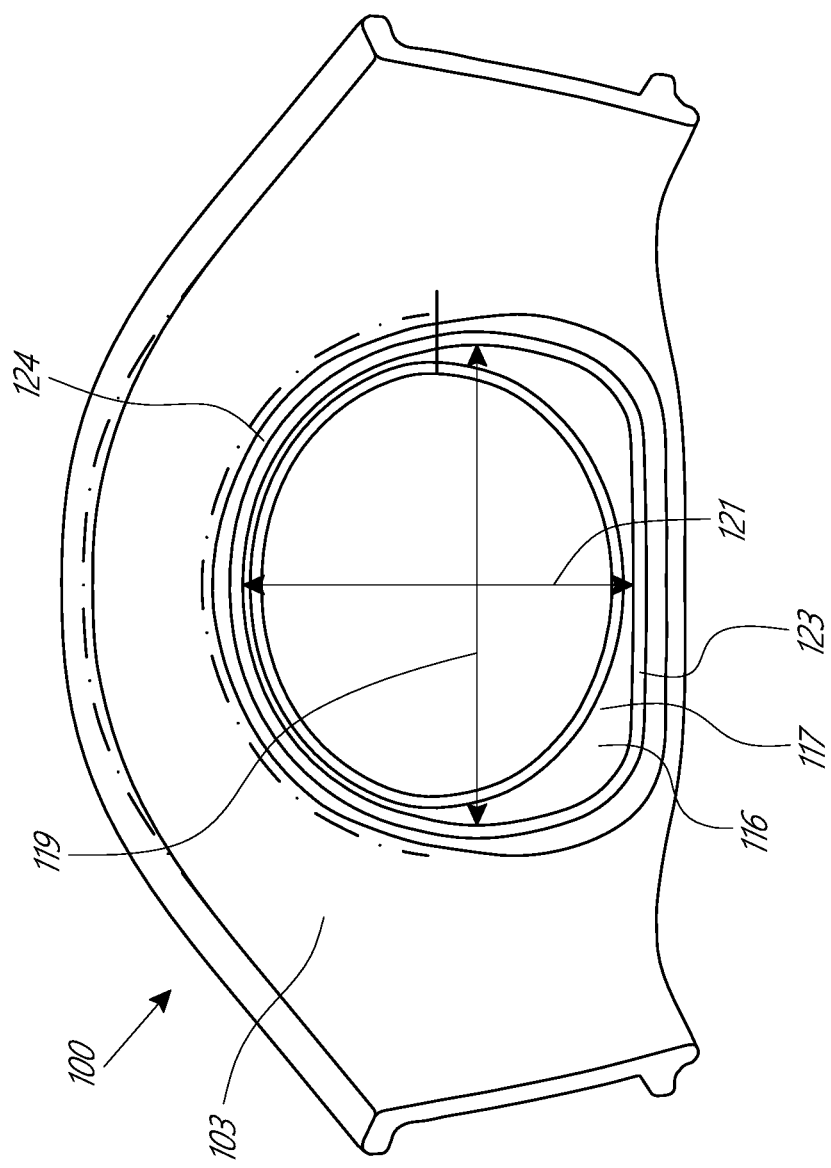
FIG. 6A is a rear view of the frame of FIG. 2.

Referring to FIGS. 6 and 6A, FIG. 6 shows a rear view of the frame 100 with respect to the vertical axis 105 and the lateral axis 107. The outlet collar aperture 117 is centrally located on the frame 100 with respect to the vertical axis 105. The origin of the outlet collar aperture 117 is aligned with the secondary lateral axis 109. The secondary lateral axis is vertically displaced from the lateral axis 107. In some configurations of the frame 100, the secondary lateral axis 109 may align with the lateral axis 107.

FIG. 6A shows a rear view of the frame 100 and shows that the outlet collar 137 is shaped like a truncated circle or partially D shaped and includes an outlet major axis 119, an outlet minor axis 121 and a truncated portion 123. The truncated portion 123 of the outlet collar 137 enables the profile of the frame 100 to be reduced relative to a frame without a truncated portion. Additionally, the truncated portion 123 provides an orientation feature to ensure correct orientation of the seal connection with the frame. The truncated portion 123 also reduces the chances of incorrect orientation when the seal 206 should be connected to the frame 100. The truncated portion also prevents rotation of the seal 206 relative to the frame 100.

In the illustrated configuration, the outlet collar aperture 117 includes both a larger lateral profile and vertical profile than the inlet collar aperture 115. The perimeter of the outlet collar aperture 117 is therefore greater than the perimeter of the inlet collar aperture 115. This larger profile is beneficial from both functional and manufacturability perspectives. From a functional perspective, when the frame 100 has an outlet collar 137 that is larger than the inlet collar 114, airflow to the user is less restricted. This results in reducing the pressure drop through the respiratory mask system in addition to at least in some way reducing the inspiration noise that is a result of the user breathing through the respiratory mask system. From a manufacturability perspective, having an outlet collar 137 that is larger than the inlet collar 114 allows a tool core to be more easily removed from the molded part.

Following the profile of the first retaining ridge 104, the interior surface 103 that is adjacent to the first retaining ridge 104 is also substantially concave with respect to the lateral axis 107. In alternate configurations, the interior surface 103 may be substantially convex with respect to the lateral axis 107. Furthermore, the interior surface 103 may be both substantially concave in regions and substantially convex in other regions with respect to the lateral axis 107.

Figure 7:
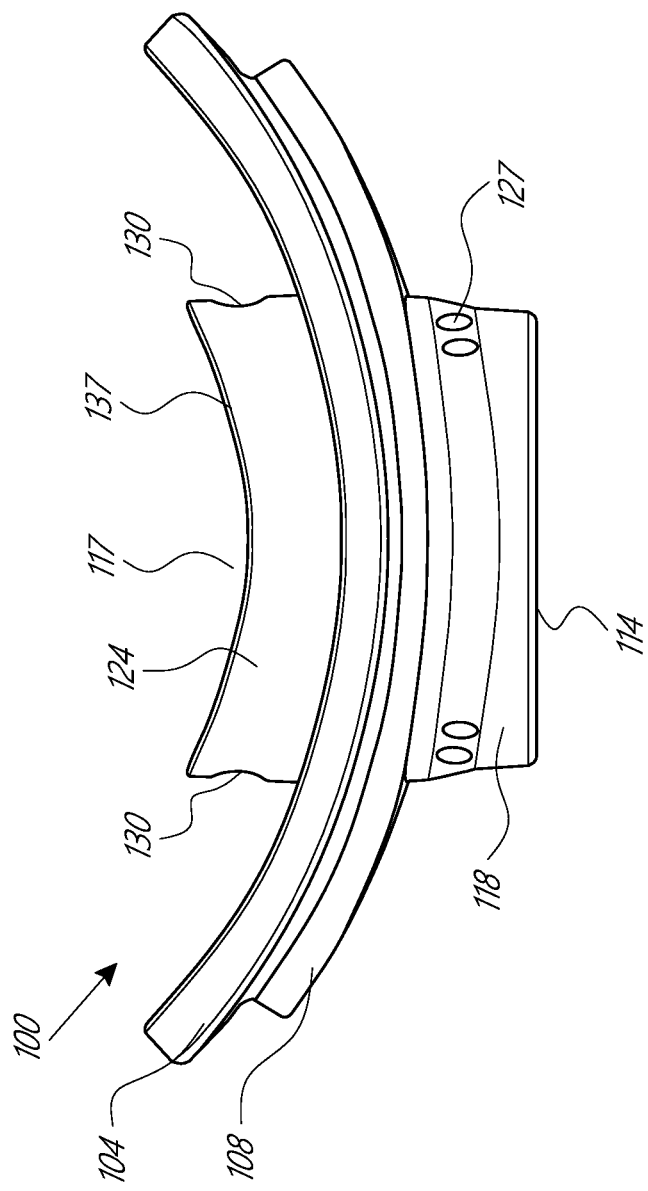
FIG. 7 is a top view of the frame of FIG. 2.

FIG. 7 shows a top view (with respect to the user) of the frame 100. Both the exterior surface 102 and the interior surface 103 are concave with respect to the user. This is exemplified by the first retaining ridge 104 being concave with respect to the user, as the first retaining ridge 104 of the exterior surface 102 is also adjacent to the interior surface 103. This configuration is beneficial as it permits a reduction in the proximal profile of the respiratory mask system. In alternate configurations, the outlet collar 137 may be convex or flat in at least one plane. Additionally, the outlet collar 137 may include both regions of concavity and convexity in at least one plane.

The outlet collar surface 124 includes a number of seal retaining recesses 130. In the illustrated configuration, the outlet collar surface 124 includes two seal retaining recesses 130. The seal retaining recesses 130 are located near each lateral extrema of the outlet collar 137. The seal retaining recesses 130 allow a seal 206 to be connected to the frame 100. In the illustrated configuration, the seal 206 connects to the frame 100 through the use of a clip that connects to the frame 100. The clip includes elevated surfaces that correspond with the seal retaining recesses 130 allowing a connection between the components to be made. Some configurations of the outlet collar 137 may include mechanisms of connecting to the seal 206 through the use of a snap fit mechanism; or friction fit mechanism. Alternate embodiments of the frame 100 may include one or more recesses on the outlet collar surface 124 to interface with the seal. Furthermore, as opposed the use of one or more recesses, one or more projections may be included on the outlet collar surface 124. These projections may interact with corresponding recesses or retaining portions on the seal 206 or seal clip to connect the components together.

Figure 5B:
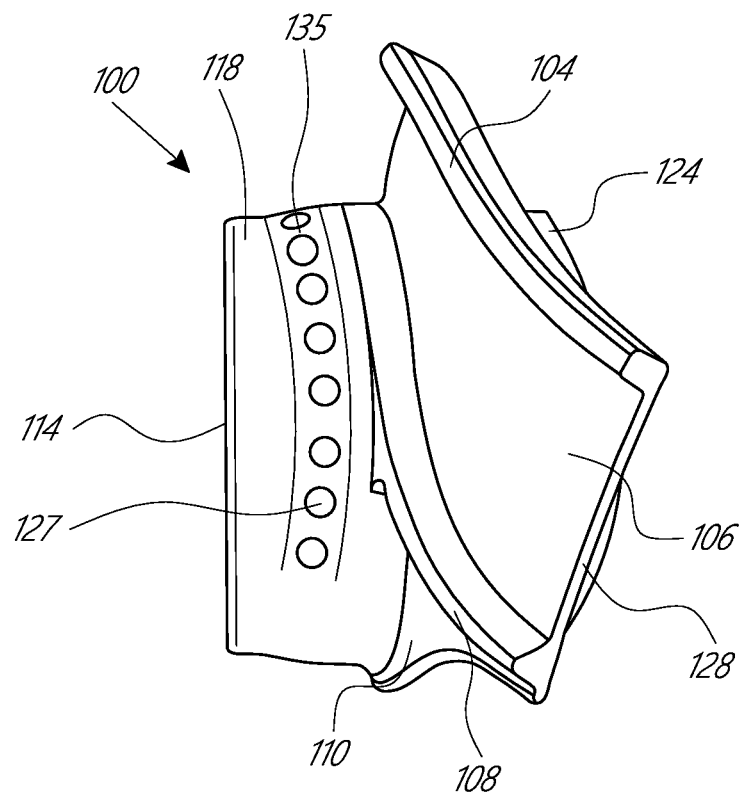
FIG. 5B is a left side view of an alternate embodiment of the frame of FIG. 2.
Figure 7A:
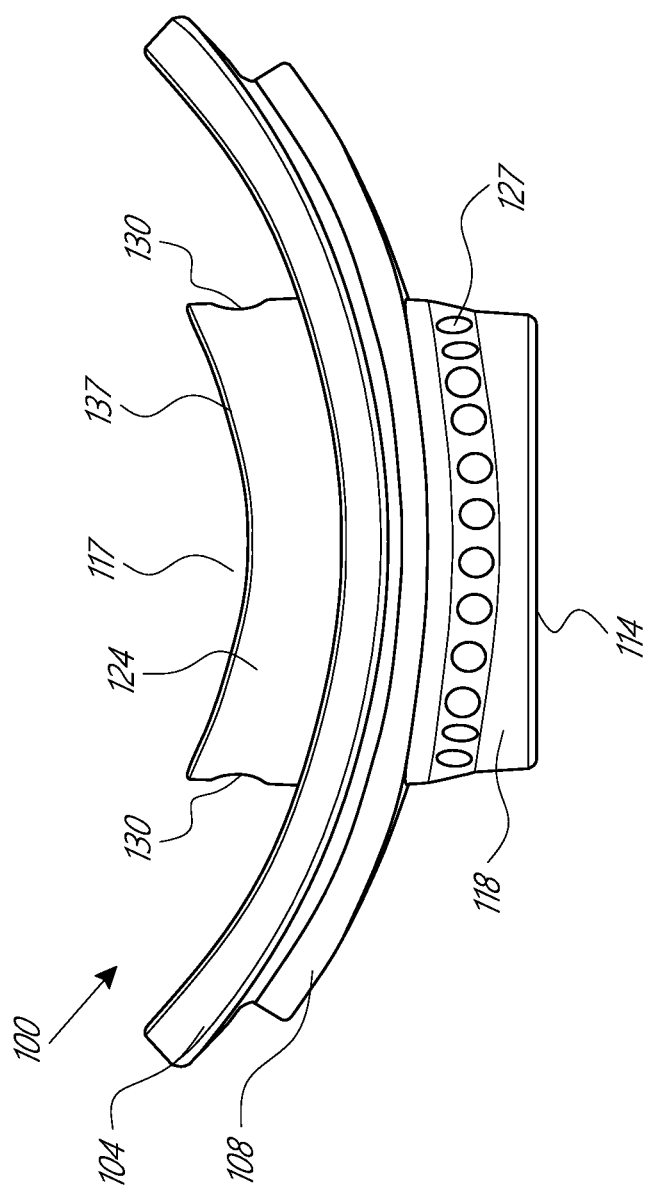
FIG. 7A is a top view of an alternate embodiment of the frame of FIG. 2.

FIG. 7A shows a top view (with respect to the user) of an alternate configuration of the frame 100. In this configuration, the bias flow holes 127 are disposed on the angled surface 135 over the inlet collar 114, for example, as also shown in FIG. 5B.

Figure 8:
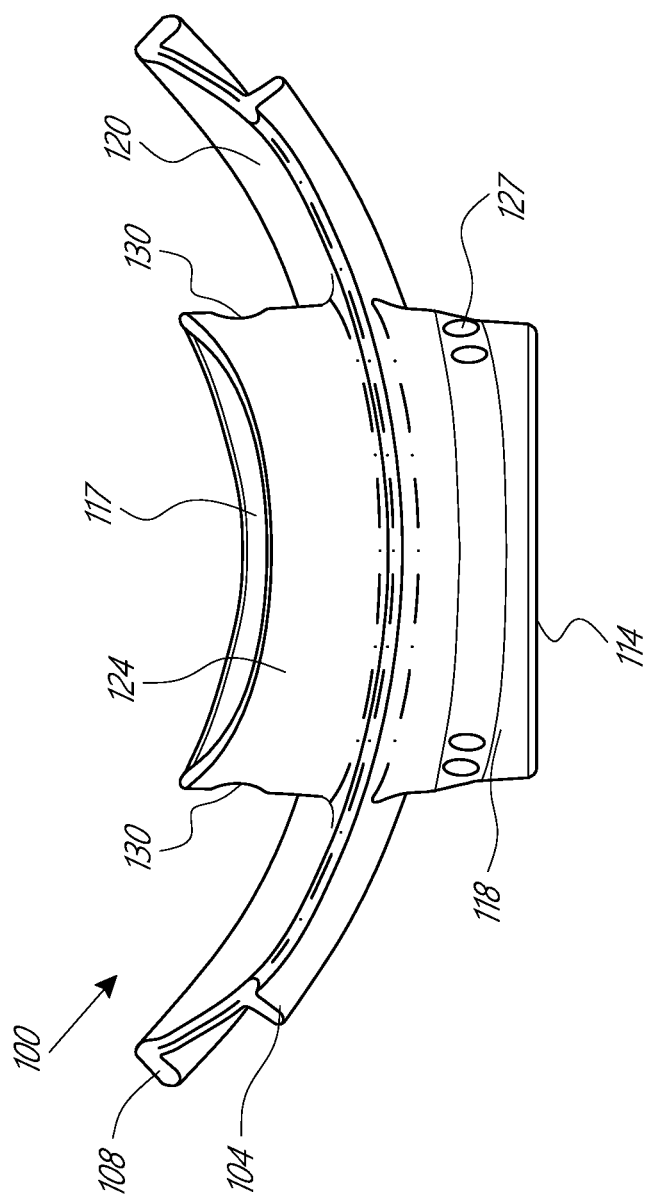
FIG. 8 is a bottom view of the frame of FIG. 2.

FIG. 8 shows a bottom view (with respect to the user) of the frame 100 illustrated in FIG. 1. The outlet collar 137 may be concave in at least one plane. At least one portion of the outlet collar 137 may be proximally displaced with respect to a second portion of the outlet collar 137.

In alternate configurations, the outlet collar 137 may be aligned on a common plane such that it is not concave in form. In some configurations, this plane is perpendicular to the outlet proximal axis 133. In other words, the vertical and lateral extrema would all share a common proximal displacement from the origin of the outlet proximal axis 133.

Figure 9:
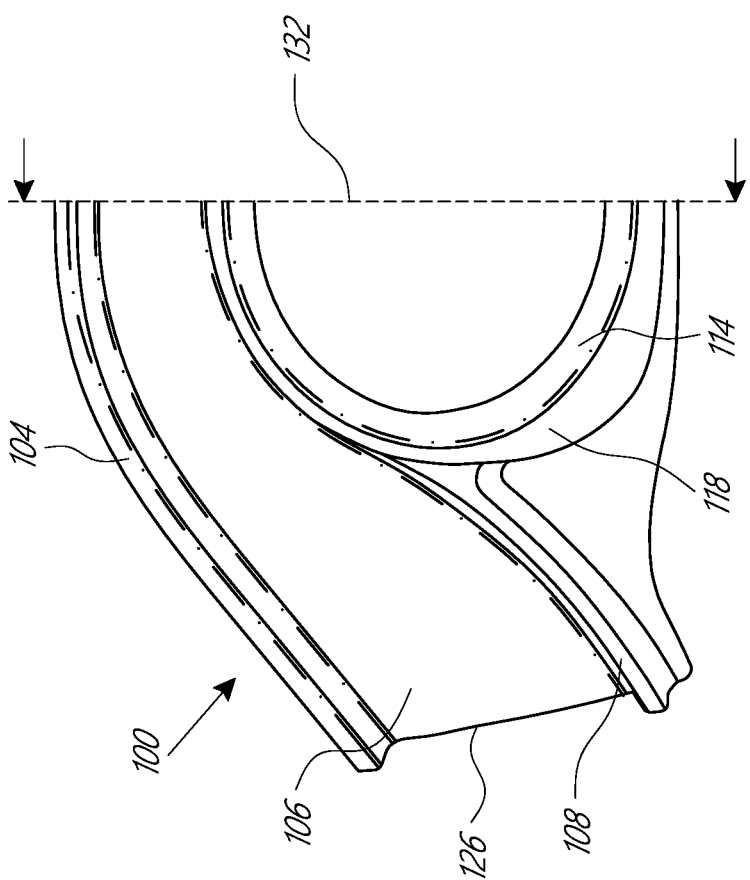
FIG. 9 is a front view of the frame of FIG. 2 with a central cross section taken.

FIG. 9 shows a front view of the frame 100 illustrated in FIG. 1, and identifies a cross section plane 132 that may be taken. This cross section plane is centrally located with respect to the frame 100 and aligns with the vertical axis 105.

Figure 10A:
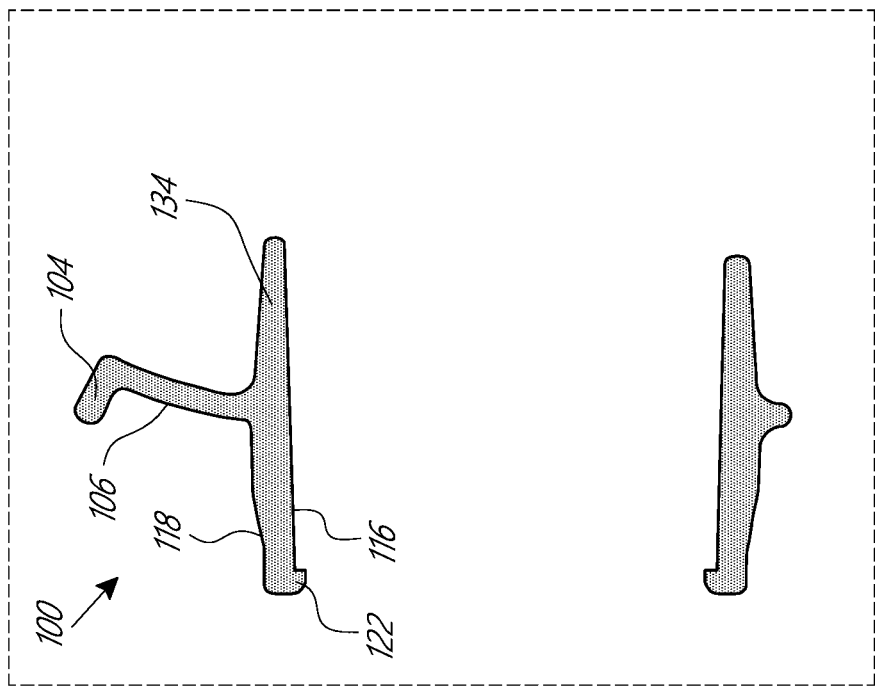
FIG. 10A is a 2D view of the central cross section of the frame of FIG. 2
Figure 10:
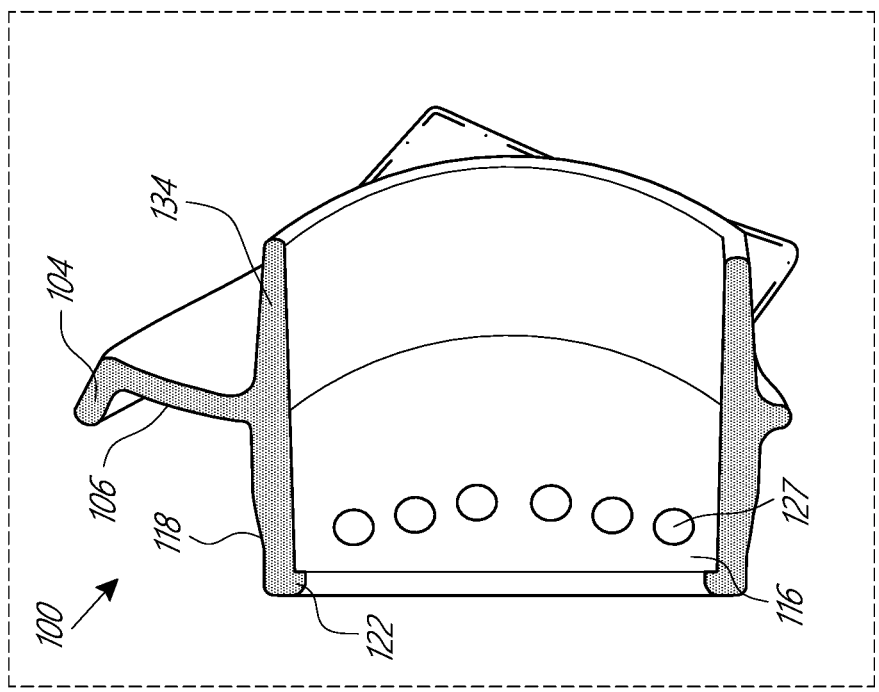
FIG. 10 is a central cross sectional view of the frame of FIG. 2.

FIG. 10 shows cross-section 10-10 formed when viewing the frame 100 perpendicularly to the cross section plane 132. A central cross section 134 shows the cross sectional profile of the frame 100 as viewed from the cross section plane 132.

FIG. 10A shows a central cross section 134 of the frame 100. The conduit retaining projection 122 projects inwardly from the periphery of the inlet collar 114. In other words, both the lateral and vertical dimensions of the inlet collar aperture 115 are less than those of the collar interior surface 116. This dimensional variation is a result of the conduit retaining projection 122. In other words, the conduit retaining projection 122 may form a lip around the interior of the distal end of the inlet collar 114. This lip may be continuous around the periphery of the inlet collar aperture 115, or may include sections of the periphery that project, and others that do not. A gas delivery conduit 6 may be connected to the frame 100 through the use of an adhesive, or the use of a clip that engages with the conduit retaining projection 122. The gas delivery conduit may be positioned adjacent to the conduit retaining projection 122 and then adhesively bonded to the frame 100. Alternately, the gas delivery conduit 6 may be removably fixed to the frame 100 through the clip. In some embodiments of the frame 100, the gas delivery conduit 6 may be permanently connected to the frame 100 through the use of a clip, or other permanent boding methods including but not limited to ultrasonic welding or over-moulding. Additionally, a conduit retaining projection 122 may not be included in some embodiments.

The conduit retaining projection 122 may alternately be on the inlet collar surface 118, projecting radially outwards from the center of the inlet collar 114. In other words, the conduit retaining projection 122 may form a lip around the exterior of the inlet collar 114. In this configuration, the gas delivery conduit 6 may connect adjacent to the inlet collar surface as opposed to the collar interior surface 116. The lip may be continuous or intermittent around the periphery of the inlet collar 114.

In the illustrated configuration, the frame 100 is constructed of a hard polymer. In some configurations, the frame 100 may be configured of any of a number of polymeric or non-polymeric materials, for example Nylon 12 or polycarbonate.

Figure 11:
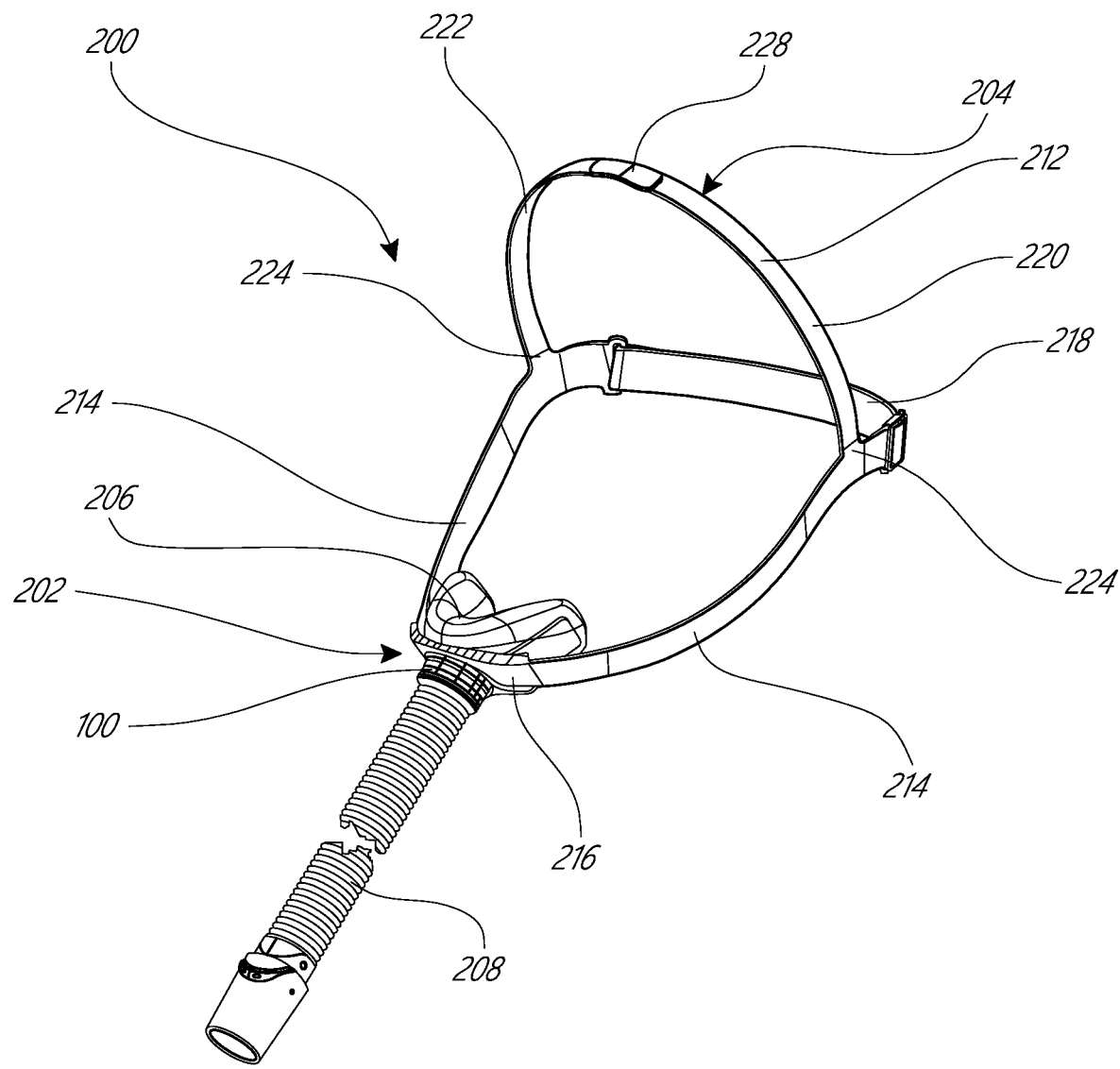
FIG. 11 is a perspective view of a second non-limiting exemplary embodiment of a respiratory mask according to the present disclosure.
Figure 12:
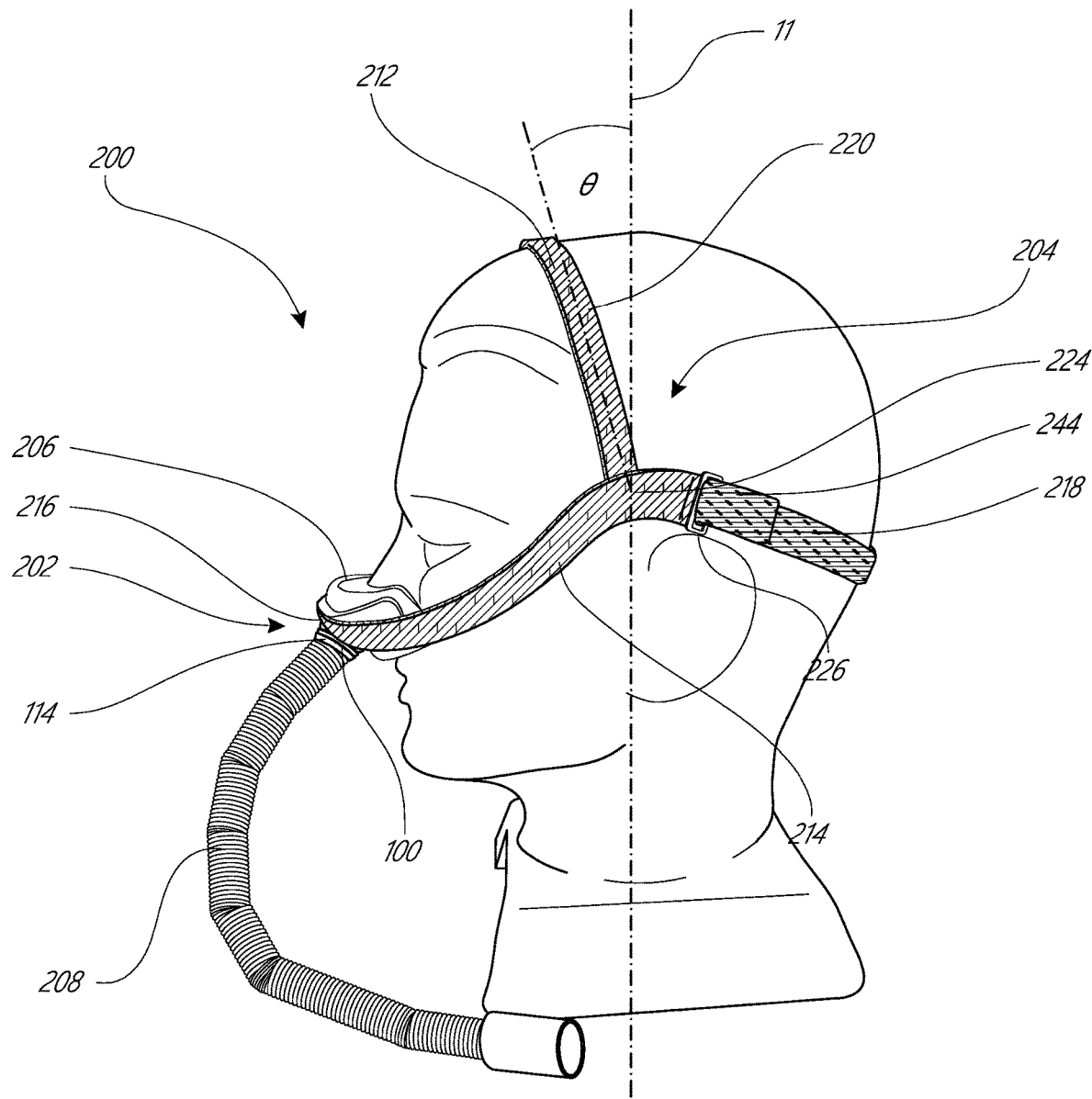
FIG. 12 is a side view of the respiratory mask of FIG. 11, in use.

FIGS. 11 and 12 show a non-limiting exemplary embodiment of a respiratory mask system 200, which is substantially similar to the respiratory mask system 1 of FIG. 1. The respiratory mask system 200 comprises a patient interface 202 and a headgear 204. The patient interface 202 comprises a seal 206 configured to connect to the frame 100, previously described, and a gas delivery conduit 208. The headgear 204 and frame 100 are configured to secure the seal 206 in a stable position below the nose of a user.

The seal 206, is substantially similar to the seal 6 described above, and has a reduced contact area with the user's face in comparison to more traditional nasal masks that seal around the user's nose, crossing the nose near or on the nasal bridge. The reduced contact area may result in reduced seal stability, which requires counteraction from the headgear 204, in order to prevent leaks and loss of therapy. The headgear 204 is configured to provide support that counteracts any forces that may act to break a seal between the seal 206 and the user's face. Forces that may interrupt the seal may include but are not limited to blow-off forces induced by the pressure of the CPAP therapy provided, hose drag forces and/or contact between the patient interface 202 and bedding caused by movement of the user.

The frame 100 provides a connection between the seal 206, and the headgear 204. FIGS. 11-12 show that the frame 100 comprises a gas delivery inlet or inlet collar 114 through which a supply of pressurized air can be provided to the seal 206, and patient's airways. The pressurized air is typically provided to the gas delivery inlet 114 via a conduit or hose, such as gas delivery conduit 208, that connects to a CPAP machine or ventilator (not shown).

Headgear

FIGS. 11 to 17 show a non-limiting exemplary embodiment of the headgear 204, of comprising a bifurcated headgear arrangement. The bifurcated headgear 204 comprises a plurality of connected straps including a top strap 212, a pair of opposing side arms 214, a yoke 216 and a rear strap 218. The top strap 212 and rear strap 218 form the bifurcated arrangement.

In use, the top strap 212 is configured to pass over the top of the user's head from one side to the other. In the illustrated configuration, the top strap 212 can comprise a forehead strap that lies over the frontal bone of the user. In this configuration the top strap 212 is angled forward of a coronal plane 11 that passes through the user's head, as shown in FIG. 12. An angle θ of between 5° and 45° is formed between the top strap 212 and the coronal plane 11. In the illustrated embodiment the top strap 212 forms an angle of 15° with the coronal plane 11. This angle directs the top strap 212 towards the forehead of the patient, which may improve the stability of the headgear 204. In other configurations, the top strap 212 is a crown strap that lies over the parietal bone or at or near a junction between the parietal bone and the frontal bone.

The rear strap 218 passes around the back of the user's head and, in some configurations, lies over the occipital bone of the user. However, in other configurations, the rear strap 218 could be positioned higher or lower on the head and/or neck of the user.

The top strap 212 and rear strap 218 are joined at the ends by one of the side arms 214 to form the bifurcated structure. In use, the top strap 212 and the rear strap 218 encircle a rear portion of the user's head. The rear portion of the user's head that is encircled may include at least part of the parietal and/or occipital regions.

In the illustrated arrangement, the top strap 212 joins the side arms 214 on each side of the headgear 204 at a junction 224. Each one of the pair of side arms 214 extends forwardly, in use, from the junction 224 towards the nose of the user and transitions into the yoke 216. In use, the headgear 204 is configured such that the junction 224 is positioned above the user's ear. It may sit forward of or rearward of the ear depending on the size of the user's head.

Integrally Formed Closed Loop

In the embodiment shown, at least some portions of the headgear 204 are rigid, semi-rigid, inelastic or substantially inextensible in response to normal or expected forces acting on the headgear 204. Other portions of the headgear 204 are elastic or extensible in response to normal or expected forces, or are at least substantially flexible in comparison to other portions.

Figure 13:
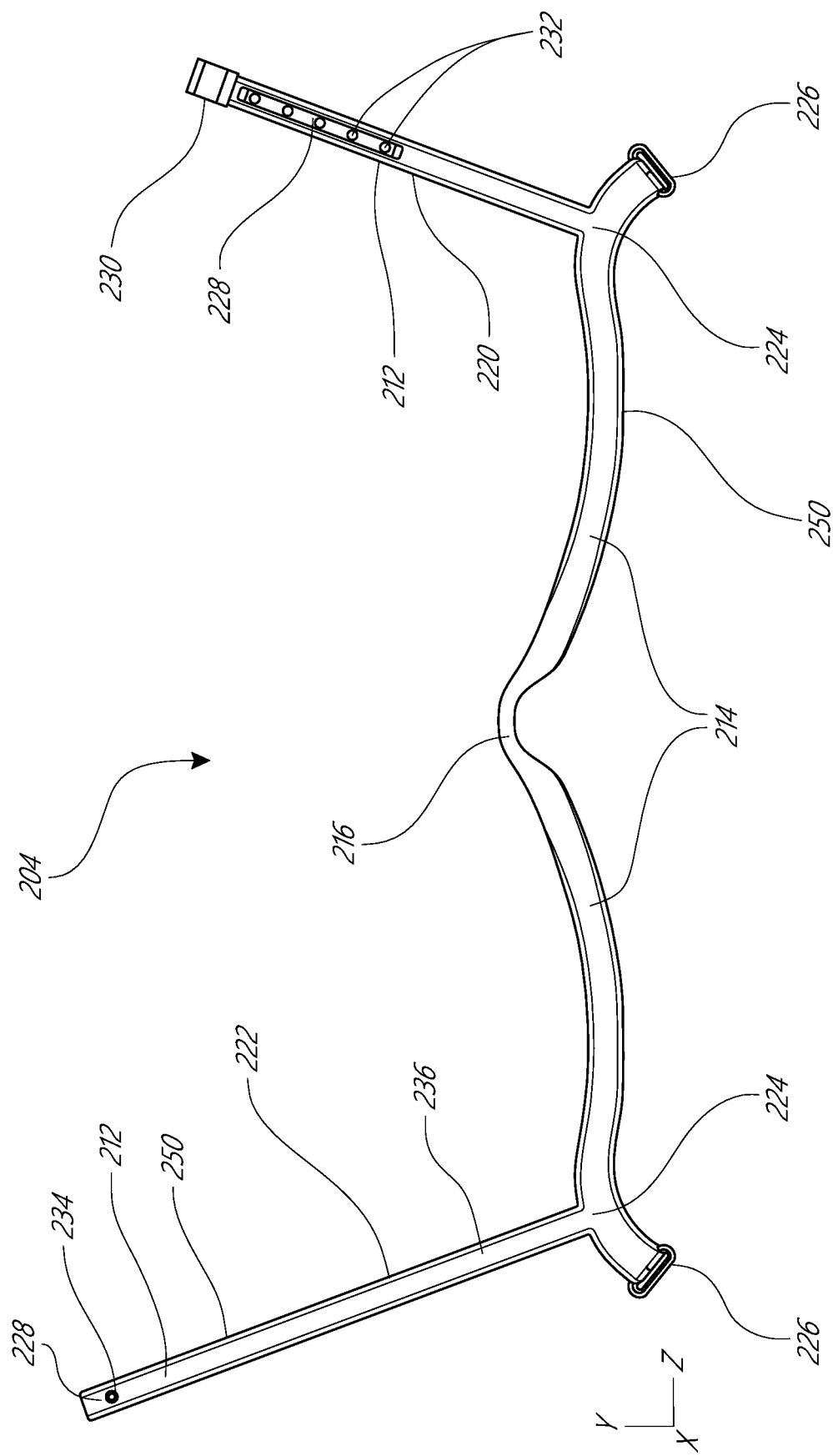
FIG. 13 is front view of part of a headgear of the respiratory mask of FIGS. 11 and 12, in a disengaged arrangement.

In the illustrated configuration, the top strap 212, junctions 224, side arms 214 and yoke 216 are rigid, semi-rigid, inelastic or substantially inextensible. The top strap 212, side arms 214 and yoke 216 are formed as a single integrally formed component, which is flat or substantially two-dimensional, as shown in FIG. 13. When the free ends of the left and right portions 220, 222 of the top strap 212 are connected to each other, by the adjustment mechanism 228, a three-dimensional closed loop is formed. In use the closed loop is configured to encircle at least a portion of the user's head. In the illustrated embodiment the closed loop encircles an upper front portion of the user's head, from the bottom of the nose up to the parietal bone, forward of the ears. In alternative embodiments the closed loop may encircle a larger or smaller portion of the user's head.

The use of a rigid, semi-rigid, inelastic or substantially inextensible material for the top strap 212, side arms 214 and yoke 216 allows the closed loop, which they form, to transfer forces effectively between the patient interface 202 and the user's head. For example, if, in use, the gas delivery conduit is pulled on by the user, bedding or a CPAP supply conduit a force may be applied to the patient interface 202 that pulls it away from the user's face. This force can be translated from the yoke 216 through the side arms 214 to the top strap 216 and then to the user's head, in order to resist the seal 206 being dislodged from the user's face by a rotation of the seal 206 in a vertical direction.

The closed loop allows the headgear 204 to be separated from the patient interface 202 without changing the tightness settings of the top strap 212. This is advantageous because the user does not need to undo and do up the headgear 204, and refit the strap with the correct tightness every time that the headgear 204 is removed from the patient interface 202. This saves time and makes fitting the headgear easier for the user. The closed loop arrangement also provides a single connection point between the headgear 204 and the patient interface 202.

In other words, the integrally formed component that forms the closed loop is rigid, semi-rigid, inelastic or substantially inextensible. In the illustrated embodiment the top strap 212, side arms 214 and yoke 216 are integrally formed from a plastic material that forms a plastic core and is covered in a textile casing, wherein the textile casing is permanently bonded to the plastic core. The plastic core provides the structure required in the headgear 204 and the textile casing provides a soft and comfortable finish to contact the user. In the illustrated embodiment the textile casing is a circular knitted tube. In alternative embodiments the textile casing may comprise several layers of textile that are cut to shape and joined along the edges, or any other tubular textile that may include, but is not limited to, woven or braided tubes. In some embodiments at least a portion of the integrally formed top strap 212, side arms 214 and yoke 216 are formed by an intra-molding process, examples of which are described in the Applicant's application PCT/NZ2015/050149, the entirety of which are incorporated herein. "Intra-molding" comprises forming a component as a plastic core and a textile casing as an integral structure by the application of molten plastic into the textile casing. A strap or any other component that has been "intra-molded" is a component formed by the application of molten plastic into the textile casing.

FIG. 13 shows that the headgear 204 of the illustrated embodiment has a top strap 212, and side arms 214 that comprise soft edges 250. The soft edges 250 are configured to extend along one or both of the longitudinal edges of the top strap 212 and the side arms 214. The soft edge is formed by a longitudinal edge portion of the textile casing that protrudes from the edges of the plastic core and is not filled by the plastic core. The soft edges provide a cushioned edge that may improve user comfort, by softening any contact between the edges of the rigid, semi-rigid, inelastic or substantially inextensible top strap 212 and side arms 214 and the user's head. This may be of particular benefit on a lower edge of the side arms 214 that sits above the user's ears in use.

In alternative embodiments the closed loop may be formed from any material that provides suitable rigidity, inelasticity or inextensibility. Materials may include but are not limited to thermoplastics and silicone. In some embodiments the material may or may not have a textile casing.

Top Strap

In the illustrated embodiment the top strap 212 comprises two strap portions, a left portion 220 and a right portion 222. The left and right portions 220, 222 are separate from one another and have a free end and a fixed end. The free ends are configured to be adjustably connected by an adjustment mechanism 228. The fixed ends are configured to extend at an angle from the side arms 214 at the junction 224.

The adjustment mechanism 228 is configured to provide a means to adjust and secure the top strap 212 in a desired adjusted length and thus adjust the size and/or tightness setting of the headgear 204. Adjustment of the length of the top strap 212 can define the positioning, in use, of the side arms 214 relative to the top of a user's ear. Shortening the length of the top strap 212 may position the side arms 214 higher above the user's ears thus avoiding contact between the side arms 214 and the user's ears. This may improve comfort for the user, as contact between the side arms 214 and the top of the user's ears may cause irritation or pressure points that over time can lead to pressure sores.

FIG. 13 shows the adjustment mechanism 228 in a disengaged position. The free end of the left portion 220 includes a guide loop 230 and plurality of holes 232 spaced along the length of the strap. The holes 232 extend through the thickness of the top strap 212. The free end of the right portion 222 includes a pip or post 234 that protrudes from an internal surface 236 of the strap.

The guide loop 230 comprises a loop structure that forms an aperture at the end of the left portion 220. The free end of the right portion 222 is configured to pass through the aperture formed by the guide loop 230. Thus, the left portion 220 and the right portion 222 can be slid relative to one another to vary an overlapping distance of the left and right portions 220, 222 and, thus, vary a length of the top strap 212. The guide loop 230 also maintains a link between the left and right portions 220, 222 when the adjustment mechanism 228 is not engaged. This may improve ease of use. The guide loop 230 is angled away from the internal surface 236 such that the aperture is at least partially offset from the thickness of the strap. This allows the right portion 222 to pass through the guide loop 230 and overlap with the left portion 220 without the left portion 222 having to bend or deform.

Figure 14:
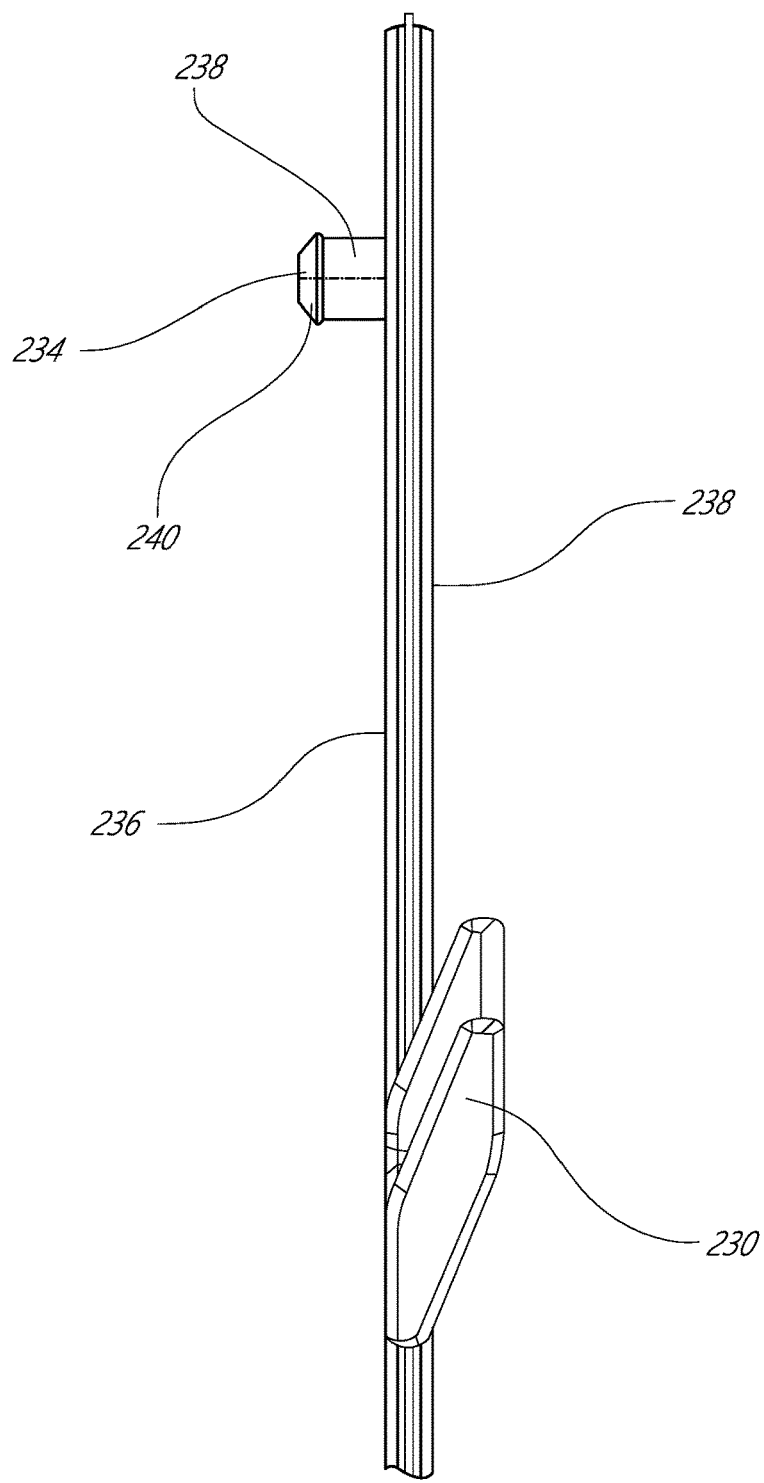
FIG. 14 is a close-up side view of a top strap of the headgear of FIG. 13, in a disengaged arrangement.
Figure 15:
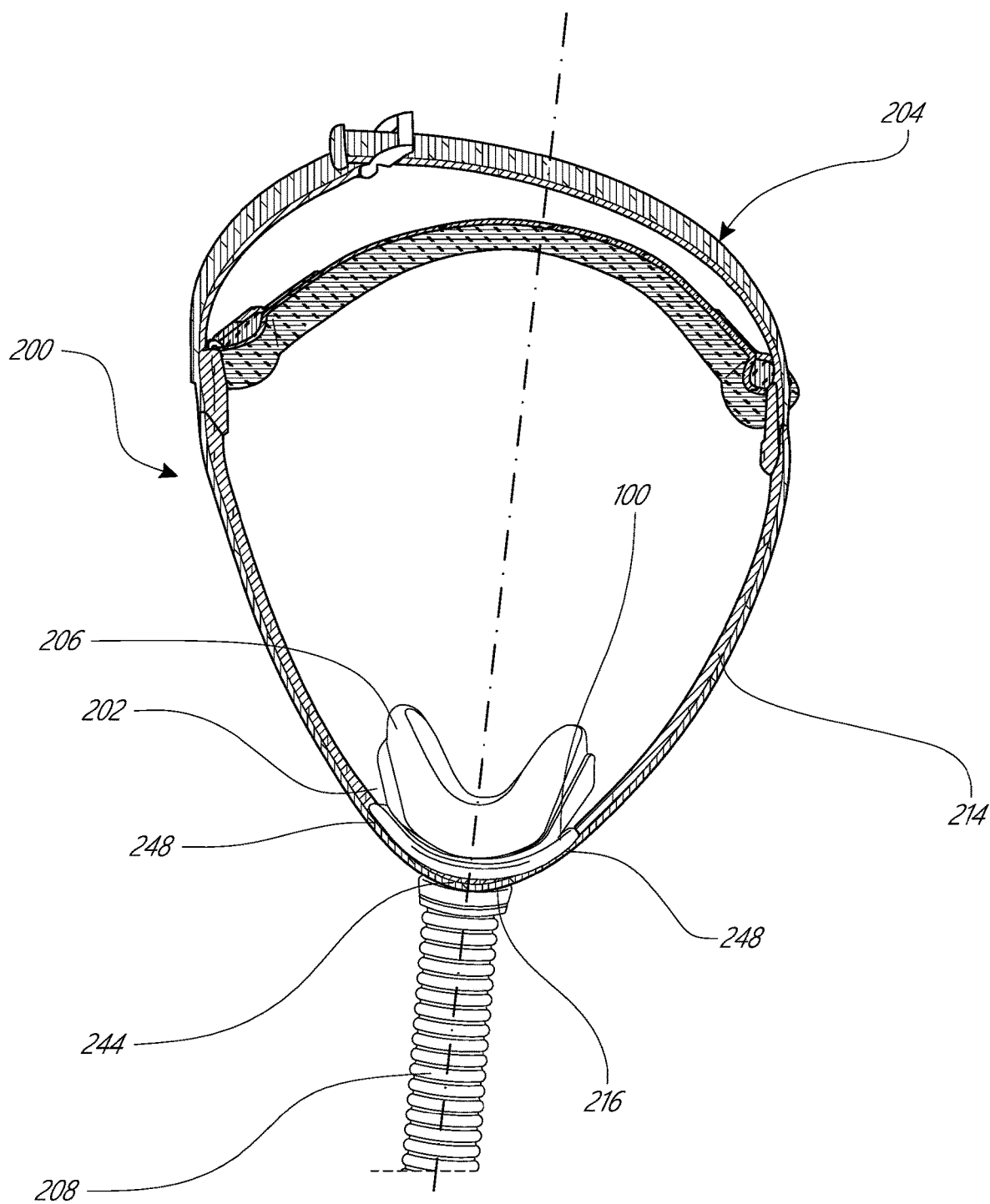
FIG. 15 is a perspective view of the top of the respiratory mask of FIG. 11.

The post 234 is configured to pass through any of the holes 232. As shown in FIG. 14, the post 234 comprises a stem 238 and a head or cap 240. The illustrated post 234 is generally T-shaped; however, other shapes can also be used, such as a cylindrical stem 238 and disc-shaped or spherical head 240, for example. The holes 232 are sized, shaped and/or otherwise configured to allow the head 240 of the post 234 to pass therethrough and to retain the post 234 once passed through the holes 232, at least in response to normal or expected forces. However, the post 234 can be deliberately removed from the holes 232 to permit separation of the left and right portions 220, 222 of the top strap 212, to allow for re-sizing of the headgear 204. Passing of the post 234 through the holes 232 can be accomplished by deformation of one or both the post 234 and holes 232. That is, the heads 240 of the posts 234 can flex or otherwise deform and the holes 232 can stretch or enlarge to facilitate passage of the head 240 of the post 234. In alternative embodiments there may be a plurality of posts.

In alternative embodiments the adjustment mechanism 228 may comprise any other suitable means of adjustably connecting the free ends of the top strap 212, such as but not limited to hook and loop fasteners, buckles.

In an alternative arrangement, an internal surface 236 of the left portion 220 can comprise a hook portion of a hook-and-loop fastener and an external surface 242 of the right portion 222 can comprise a loop portion of the hook-and-loop fastener. This arrangement can also be reversed. In some configurations, a material of the top strap 212 can define the loop portion of the hook-and-loop fastener. In other words, the loop portion may not be a discrete element of the top strap 212.

Side Arms

The pair of opposing side arms 214 are configured, in use, to link the yoke 216 to the top strap 212 on each side of a user's face. This arrangement allows rotational forces that are applied to the patient interface 202 to be translated from the yoke 216 and the user's head in order to resist rotation of the seal 206 relative to the user's face.

The side arms 214 comprise elongate straps that are shaped to curve across a user's cheeks towards the temple and over the ear, in use. The curvature is such that the side arms 214 avoid the eyes to provide an uninterrupted field of view and improved comfort for the user. The curvature can follow the line of a user's cheek bones so that contact between the side arm 214 and the user's cheeks transfers forces away from the patient interface 202 so that the seal with the user's face is not disturbed.

The side arms 214 further comprise a buckle 226 that is integrally formed at a free end of each of the side arms 214. In use, the free ends of the side arms 214 extend rearward beyond the junction 224 with the top strap 212, and the buckle 226 is positioned either above or behind the user's ear.

The buckle 226 comprises an extension of the free ends of the side arms 214 and an aperture that extends through the thickness of the side arms 214. The aperture is configured to receive the rear strap 218. In alternative embodiments the buckle 226 may comprise a hook or any other geometry suitable for adjustably tethering the rear strap 218 to.

The side arms 214 may be resiliently flexible towards and away from the face of the user in an approximately horizontal plane (when worn), to accommodate different face sizes, but are relatively inflexible in an approximately vertical plane. The illustrated side arms 214 are solid, but other versions of the side arms could include one or more apertures or cut-outs extending lengthwise of the side arms to increase the resilient flexibility of the side arms towards and away from the face of the user, but to retain relative inflexibility in an approximately vertical plane (when worn). The vertical inflexibility of the side arms 214 allows the side arms 214 to transfer forces that may be applied to the patient interface 202, such as but not limited to blow-off forces or hose drag/pull, to the top strap 212 and rear strap 214. This may help to reduce the likelihood of the seal 206 being dislodged from the user's face and interrupting the delivery of the therapy.

Yoke

Figure 16:
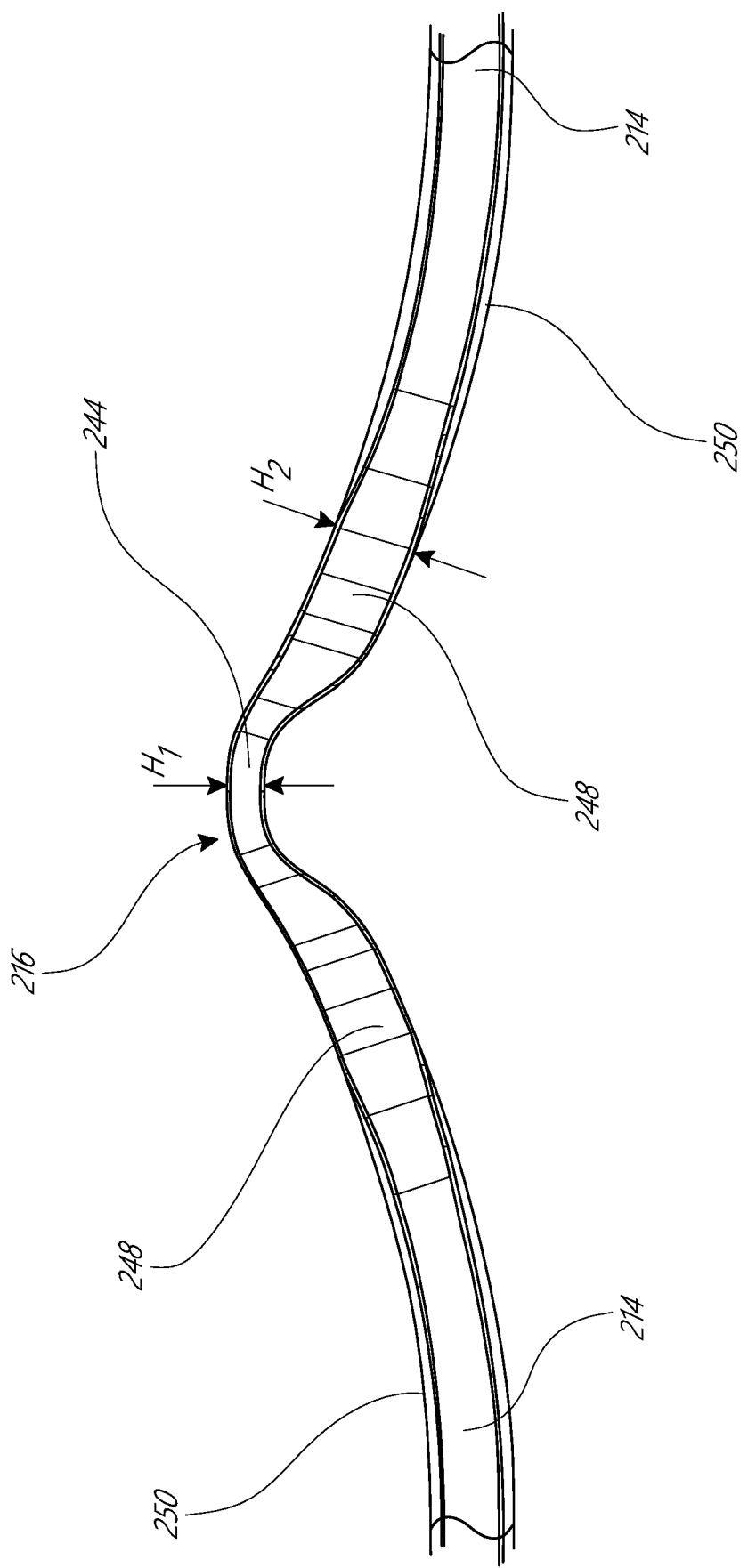
FIG. 16 is a close-up front view of a yoke of the headgear of FIG. 13 in a disengaged arrangement.

In use, the yoke 216 is symmetrical about a sagittal plane and comprises a substantially "U" shaped structure when viewed from above, as in FIG. 16. The yoke 216 follows the curvature of the frame 100 and is configured to connect the patient interface 202 to the headgear 204 via the frame 100. The yoke 216 comprises a central bridge 244 and a pair of lateral rearward portions 248 that extend laterally and rearwardly from each side of the central bridge 244. The yoke 216 provides a single connection between the headgear 204 and the frame 100 that is independent of any other features of the frame 100. This allows the headgear 204 to be disconnected from the frame without interfering with or disconnecting any other part of the patient interface 202.

The yoke 216 is configured to provide a connection between the frame 100 and the headgear 204 that supports the patient interface 202 in a vertical and horizontal direction relative to the user when the respiratory mask 200 is worn. By supporting the patient interface 202 in vertical and horizontal directions rotation of the seal 206 relative to the user's face is reduced and thus leaks may be reduced.

The central bridge 244 is shaped such that it fits within the recessed channel 106 of the frame 100 (described above). The central bridge 244 is configured to temporarily or permanently connect to the recessed channel 106 by means such as but not limited to a snap-fit connection, a friction-fit connection, a clip mechanism, adhesives or welding. The central bridge 244 curves over the inlet collar 114 of the frame 100 and transitions into the lateral rearward portions 248.

The lateral rearward portions 248 form an integrally formed transition between the central bridge 248 and the side arms 214. The lateral rearward portions 248 are positioned laterally of the central bridge 244 and curve around the frame 100 in a rearwards direction, when the respiratory mask 200 is worn by a user.

As shown in FIG. 16, the central bridge 244 has a height $H_1$ that is less than a height $H_2$ of the lateral rearward portions 248 of the yoke 216. Height $H_1$ is less than height $H_2$ in order to minimize the size of the frame 100. Height $H_2$ is greater than height $H_1$ in order to provide a desired level of structure in the vertical direction to prevent rotation of the patient interface 202 relative to the user's face. $H_1$ may be between 1 mm and 12 mm, or between 4 mm and 7 mm. In the illustrated embodiment $H_1$ is 5.5 mm. $H_2$ may be between 5 mm and 16 mm, or between 8 mm and 13 mm. In the illustrated embodiment $H_2$ is 12.5 mm.

The side arms 214 may continue from the lateral rearward portions 248 at the same or greater height than $H_2$. In some embodiments the height of the side arms 214 increases in a direction moving away from the yoke 216. The transition between $H_1$ and $H_2$ occurs between the central bridge 244 and the lateral rearward portions 248. The lateral rearward portions 248 are configured to contact the frame 100 until the height has transitioned fully to that of $H_2$. This configuration allows the frame 100 to provide structural support to the yoke 216 over the maximum height such that there are no parts of the yoke 216 or side arms 214 with a small height that are unsupported and may form a weak point. This enables forces to be translated from the frame 100 through the yoke 216 to the side arms 214 without passing through a weak point that may cause the side arms 214 or yoke 216 to twist or bend a vertical direction allowing rotation of the patient interface 202. In some embodiments the height of the side arms 214 is no greater than 16 mm; in order provide a minimal respiratory mask.

It can be seen in FIG. 16 that the soft edges 250 of the side arms 214 are transitioned out so that they do not exist in the yoke 216. This may provide an improved connection between the yoke 216 and the frame 100, by providing rigid, semi-rigid, inelastic or substantially inextensible edges that can be engaged by the recessed channel 106 of the frame 100. The soft edges 250 are not required on the edges of the yoke 216 as they are not likely to come into contact with the user and cause discomfort or irritation. The size of the yoke 216 may be minimized by transitioning out the soft edges 250; therefore the size of the frame 100 may be minimized to provide a less obtrusive respiratory mask system 200.

Figure 17:
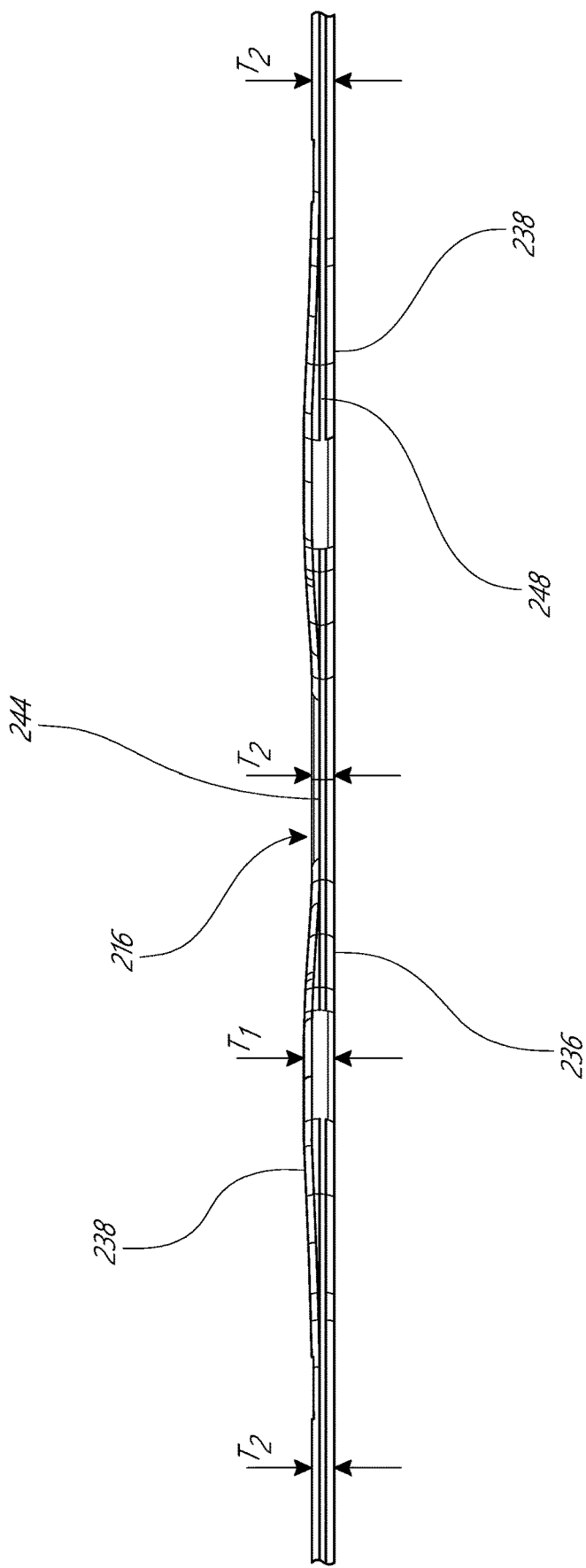
FIG. 17 is a close-up plan view of the yoke of the headgear of FIG. 13 in a disengaged arrangement.

FIG. 17 shows that in the illustrated embodiment, the lateral rearward portions 248 of the yoke 216 have a greater wall thickness $T_1$ in a direction perpendicular to the internal surface 236 than a wall thickness $T_2$ at a center of the yoke 216 and the side arms 214. The increased thickness provides increased structure at the lateral most part of the yoke 216 that contacts the frame 100. This allows for the effective translation of forces from the side arms 214 to the frame to minimize vertical rotation of the patient interface 202. The lateral rearward portions can have a thickness $T_1$ of between 1 mm and 4 mm. In the illustrated embodiment the thickness $T_1$ is 2.9 mm. The central bridge 244 and side arms 214 have a thickness $T_2$ of between 0.5 mm and 3 mm. In the illustrated embodiment $T_2$ is 2.1 mm.

The reduced thickness $T_2$ of the side arms 214 relative to the greater wall thickness $T_1$ of the lateral rearward portions 248 of the yoke 216 can facilitate horizontal flexibility in the side arms 130 relative to the yoke 216 (when worn). This enables the side arms 214 to flex in a horizontal direction to cater for differing facial geometries, whilst providing stability in the vertical direction, when the respiratory mask 200 is worn by a user.

Rear Strap

The rear strap 218 comprises an elongate strap that extends between and is connected about the buckles 226 of the side arms 214. The ends of the rear strap 218 are adjustably tethered through the apertures of the buckles 226 such that the length of the rear strap 218 can be adjusted. Adjustment of the length of the rear strap 218 can further adjust the overall size of the headgear 204 to fit each individual user.

In the illustrated configuration, the rear strap 218 is elastic or extensible. Such an arrangement allows the rear strap 218 to stretch to adjust a circumferential length of the headgear 204. The amount of stretch of the rear strap 218 can be limited and, thus, the rear strap 218 can also be adjustable in length, as previously described. In some configurations, it is preferable for circumferential length adjustment to occur at the back of the user's head, which is less susceptible to lengthening in response to blow-off forces. The rigid, semi-rigid, inelastic or substantially inextensible nature of the junctions 224 and side arms 214 positioned on the side and forward portions of the user's head assists in maintaining a desired circumferential length of the headgear 204 despite the elastic nature of the rear strap 218. In some cases, frictional forces between the portions of the headgear 204 and the side and forward portions of the user's head inhibit movement or lengthening of the headgear 204 in response to blow-off forces. However, in other arrangements, the rear strap 214 can be rigid, semi-rigid, inelastic or substantially inextensible and, in such cases, may be adjustable in length.

In the illustrated embodiment the rear strap 218 comprises a length of laminated textile and foam, such as but not limited to Breathoprene®. The rear strap is elastic such that it can be stretched to allow the headgear 204 to be pulled over a user's head without adjusting the length of the rear strap 218. This improves ease of use. In alternative embodiments the rear strap may comprise any suitable textile or fabric material.

The rear strap 218 has two lateral ends 244 that are configured to pass through the buckles 226 and fold back on themselves (shown in FIG. 12) where they can be fastened at a user defined position. The lateral ends 226 of the rear strap 218 can be fastened to an outer surface of the rear strap 218 by a fastening means such as but not limited to a hook and loop fastener. The overlap between the folded over lateral ends 244 and the rest of the rear strap 218 determines the length of the rear strap 218 and the sizing of the headgear 204. In the illustrated embodiment the lateral ends 244 of the rear strap 218 include a fastener tab in the form of a hook component of a hook and loop fastener (such as but not limited to Velcro® brand hook and loop fastener). The fastener tab is configured to be fastened to a loop component on the outer surface of the rear strap 218. In the illustrated embodiment the outer surface of the rear strap 218 comprises a material that provides the loop component of the hook and loop fastener. In alternative embodiment this arrangement of hook and loop fastener can be reversed such that the hook component is on the outer surface of the rear strap 218.

Alternative Headgear Embodiment

Figure 18:
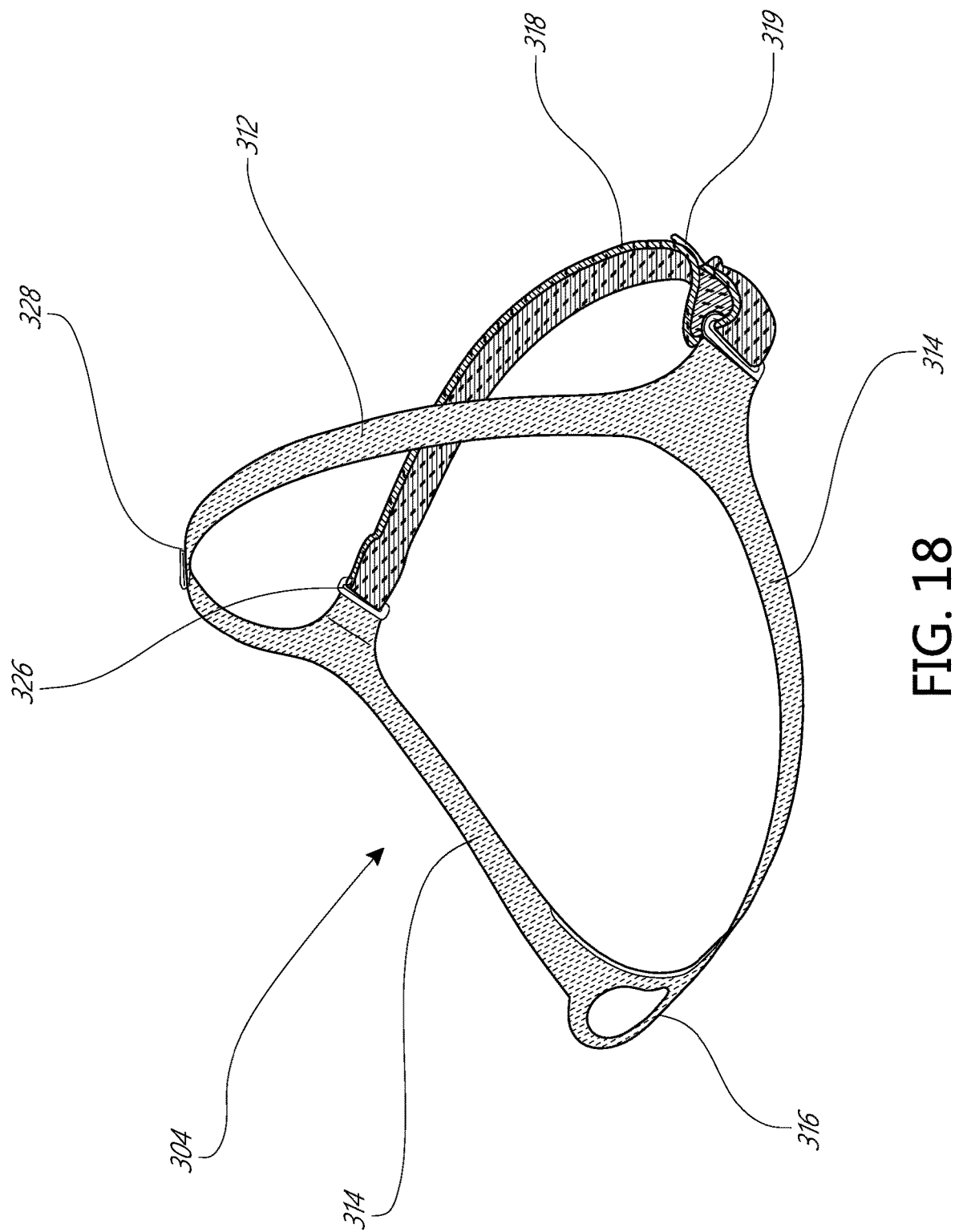
FIG. 18 is a perspective view of a second non-limiting exemplary embodiment of a headgear for use in combination with the respiratory mask of FIG. 1.
Figure 19:
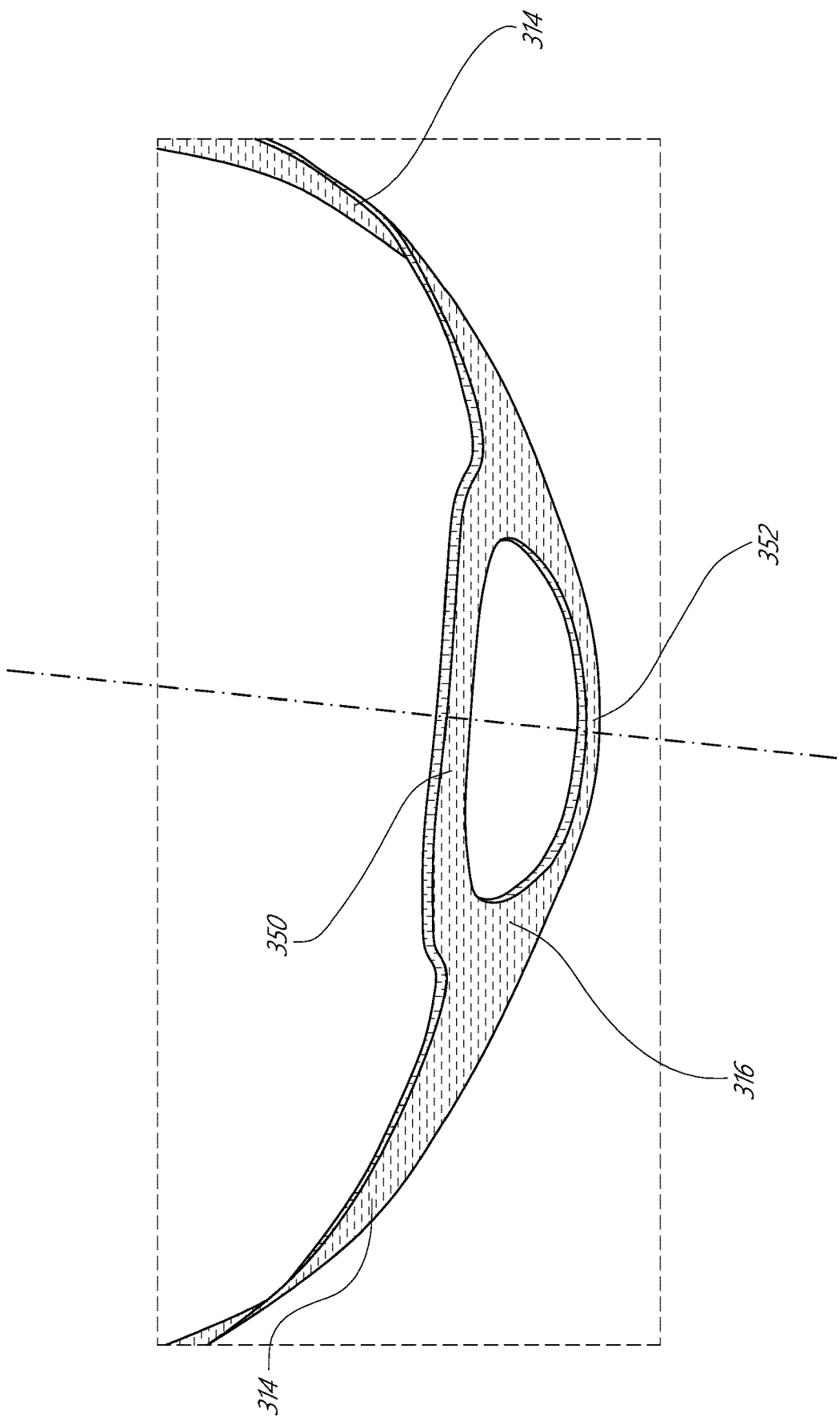
FIG. 19 is a perspective front view of the yoke of the headgear FIG. 18.

FIGS. 18 and 19 show another non-limiting exemplary embodiment of a headgear 304. For the purposes of this description, features of this embodiment that are substantially similar to those of the previous embodiment of headgear 204 are allocated reference numerals that are the same plus one hundred. For example headgear 204 becomes headgear 304 in the present embodiment. For the sake of brevity only those features which differ substantially from the previous embodiment will be described in detail here. It is to be understood that all other features are substantially as described in relation to the headgear 204.

Headgear 304 comprises a top strap 312, pair of opposing side arms 314, yoke 316 and a rear strap 318. As in the previous embodiment the top strap 312, side arms 314 and yoke 316 are rigid, semi-rigid, inelastic or substantially inextensible and formed as a single integrally formed component. The single integrally formed component can be arranged to form a closed loop that, in use, encircles an upper front portion of a user's face. The top strap 312, side arms 314 and rear strap 318 are substantially the same as the top strap 212, side arms 214 and rear strap 218 as previously described. As shown, the rear strap 318 can extend between and be connected to buckles 326 of the side arms 314. One or both ends of the rear strap 318 can include a grip tab 319 that can advantageously allow the user to more easily grip the end(s) of the rear strap 318 to adjust and/or secure the rear strap 318. The top strap 312 can be adjustment via an adjustment mechanism 328.

The yoke 316 of the present embodiment is configured to provide a connection between the headgear 304 and patient interface (not shown, but can be similar to patient interface 202). The yoke 316 is symmetrical about a sagittal plane (shown in FIG. 19), in use, and comprises a loop structure formed by an upper bridge 350 and a lower bridge 352 that are joined at lateral ends by a front end of each of the side arms 314. The upper and lower bridges 350, 352 are configured to removably connect to a frame (not shown, but may be similar to frame 100) about an inlet collar or connection of the frame. The upper and lower bridges 350, 352 are curved such that the loop structure they form is continuous and defines an aperture configured to encircle the inlet collar. This curved shape may be configured to fit within a perimeter of the frame, so as to reduce the overall size of the patient interface.

The upper and lower bridges 350, 352 are configured to resist rotational forces that may be applied to the patient interface. The upper and lower bridges 350, 352 provide two paths through which forces can be transferred from the frame to the headgear 300; this may evenly distribute rotational forces so that the there is no bias towards upwards or downwards rotation.

Alternative Frame Embodiment

Figure 20:
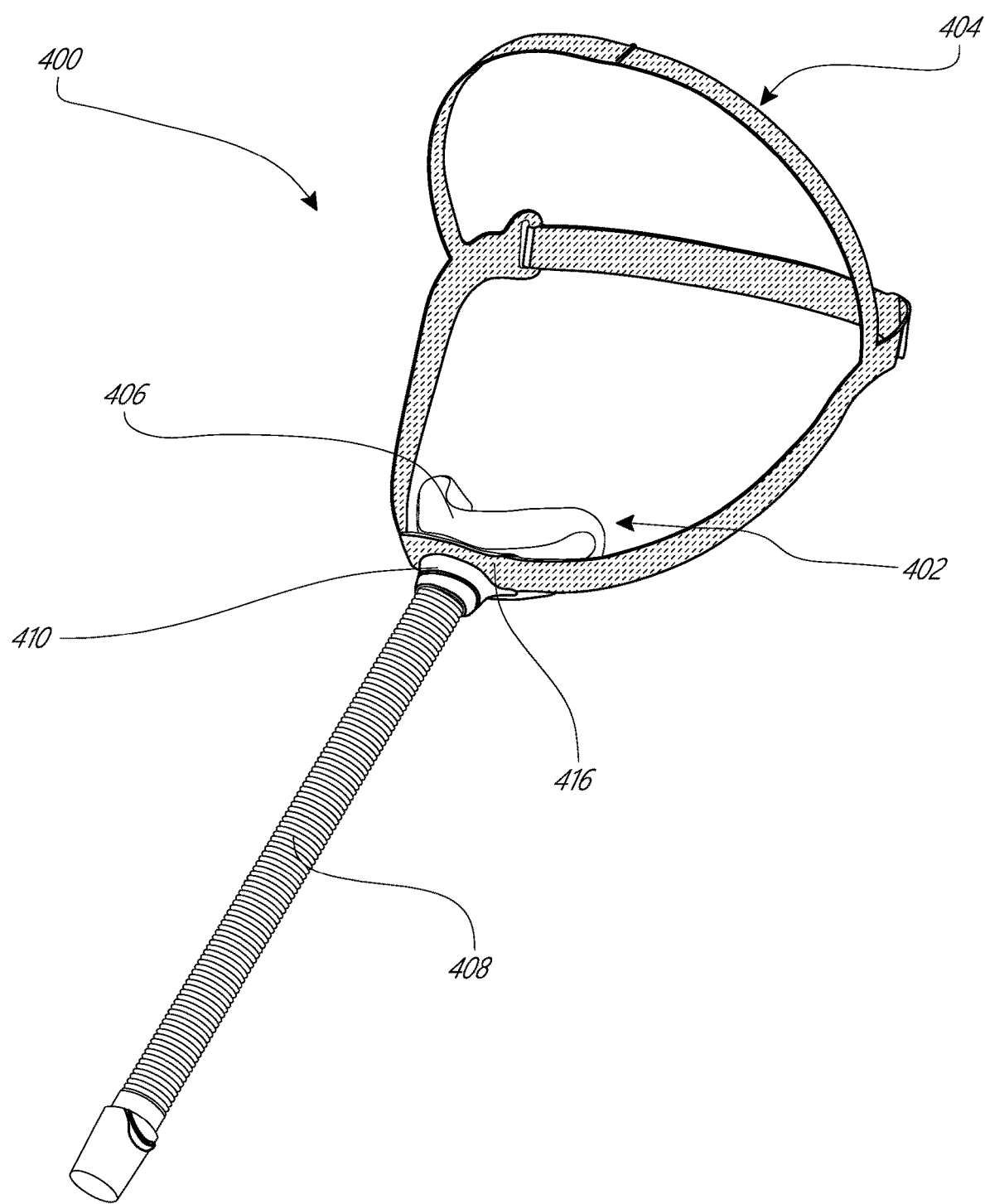
FIG. 20 is a perspective view of a non-limiting exemplary embodiment of a respiratory mask according to the present disclosure.
Figure 21:
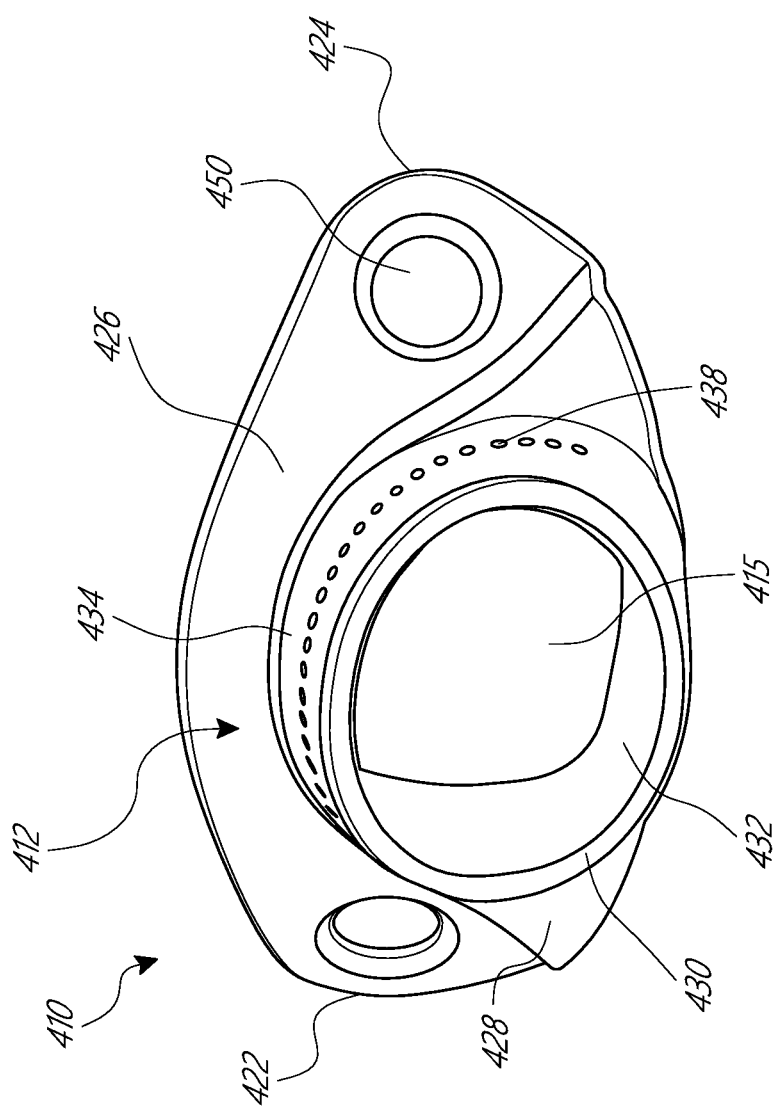
FIG. 21 is a front perspective view of a frame of the respiratory mask of FIG. 20.
Figure 22:
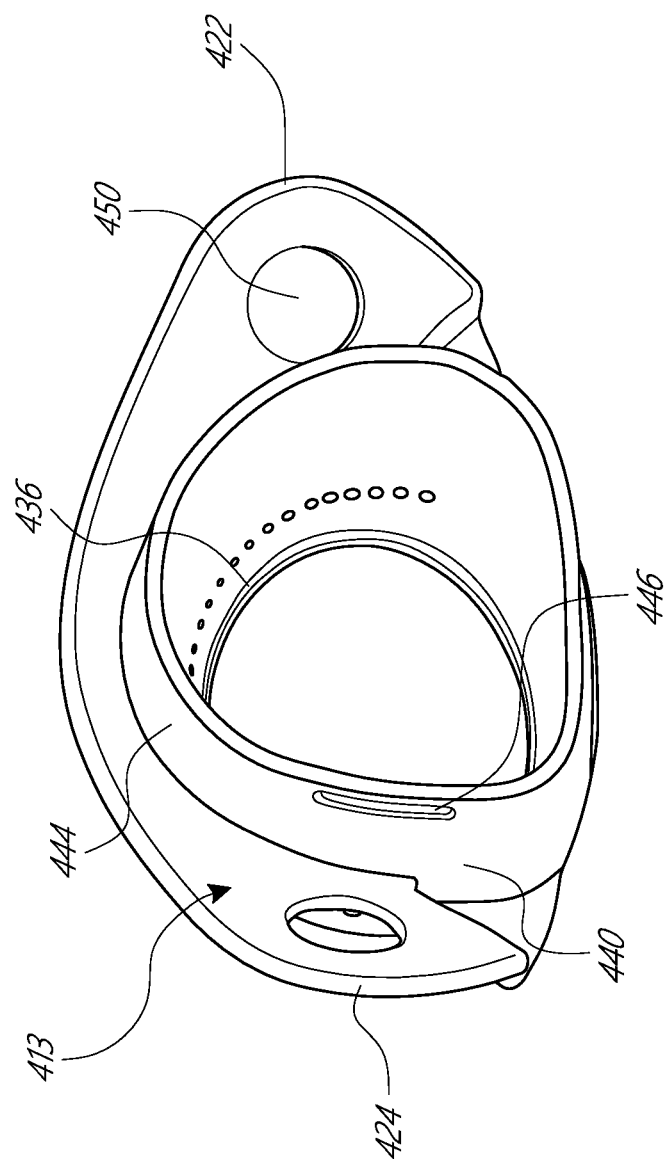
FIG. 22 is a rear perspective view of the frame of FIG. 21.
Figure 23A:
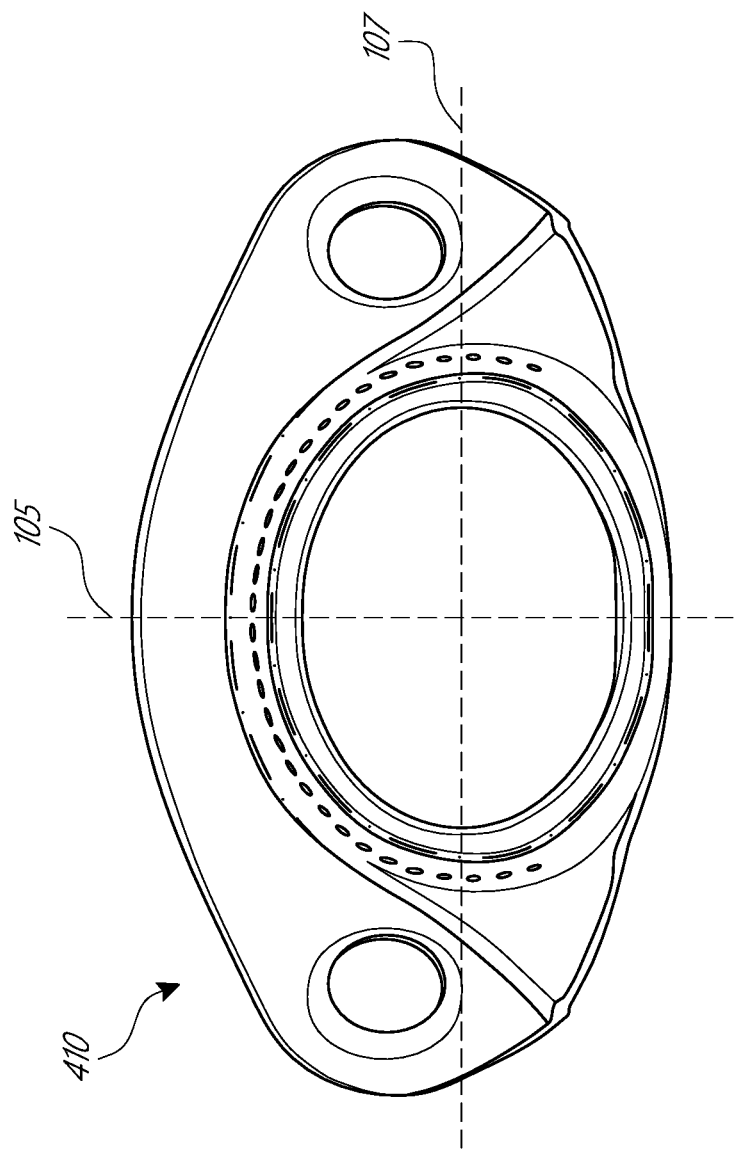
FIG. 23A is a front view of the frame of FIG. 21 showing axes of the frame.
Figure 23B:
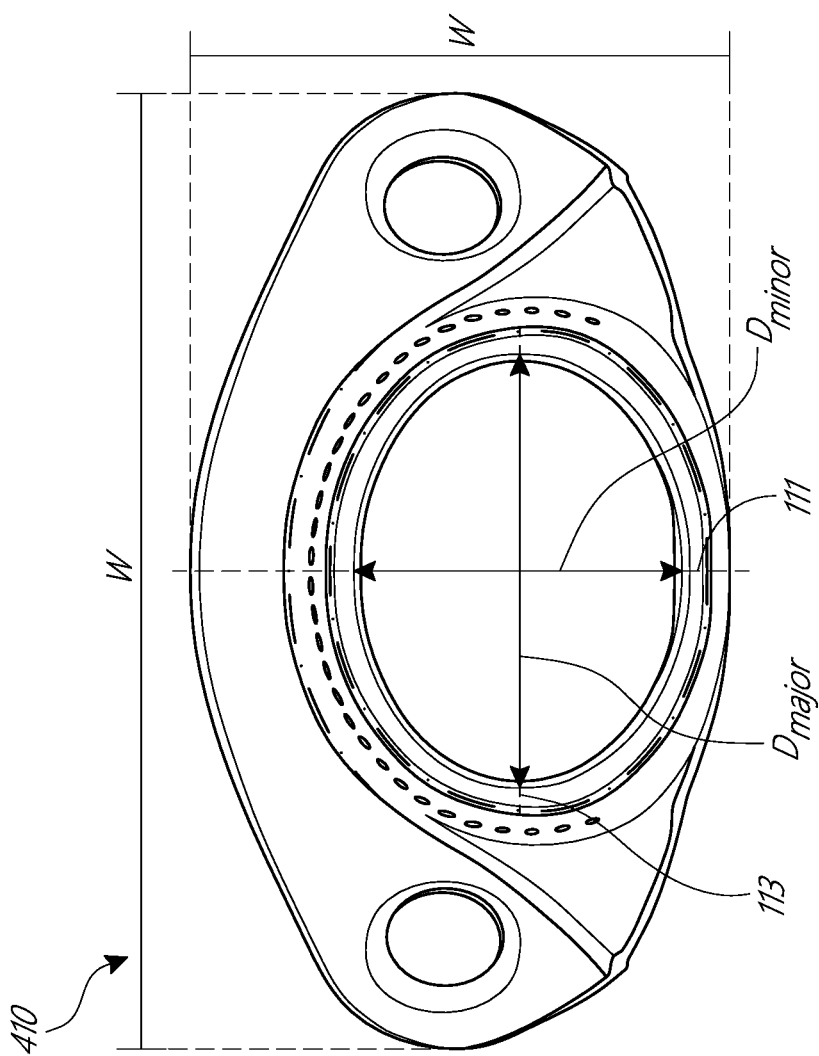
FIG. 23B is a front view of the frame of FIG. 21 showing various axes and dimensions.

FIG. 20 shows another non-limiting exemplary embodiment of a respiratory mask assembly 400. The respiratory mask assembly 400 includes a patient interface 402 and a headgear 404. The patient interface 402 includes a seal 406 configured to connect to a frame 410 and a gas delivery conduit 408. In some embodiments, the frame 410 has a reduced or smaller overall profile compared to the frame 100. The headgear 404 and frame 410 are configured to secure the seal 406 in a stable position below the nose of a user in use.

The seal 406 can be substantially similar to the seal 6 described above and has a reduced contact area with the user's face in comparison to more traditional nasal masks that seal around the user's nose, crossing the nose near or on the nasal bridge. The reduced contact area may result in reduced seal stability, which may require counteraction from the headgear 404, in order to prevent leaks and loss of therapy. The headgear 404 is configured to provide support to counteract forces that may act to break a seal between the seal 406 and the user's face. Forces that may interrupt the seal may include, but are not limited to, blow-off forces induced by the pressure of the CPAP therapy provided, hose drag forces, and/or contact between the patient interface 402 and bedding caused by movement of the user.

The frame 410, illustrated in FIGS. 21-23B and 26A-32B provides a connection between the seal 406 and the headgear 404. Like the frame 100, the frame 410 has an exterior surface 412, an interior surface 413, and a fluid path 415 extending therethrough as shown in FIGS. 21-23B. The exterior surface 412 and interior surface 413 span from a first lateral edge 422 to a second lateral edge 424. The exterior surface 412 faces away from the user in use and acts as an interface among the frame 410, a headgear (such as headgear 404), and a gas delivery conduit (such as gas delivery conduit 408). The interior surface 413 faces the user in use and may contact the seal 406 and/or a clip connected to the seal 406. In use, the gas delivery conduit 408 is coupled to the frame 410 such that the gas delivery conduit 408 is in fluid communication with the fluid path 415.

The exterior surface 412 includes a recessed surface 426 and an elevated surface 428. In some embodiments, a portion of the headgear 404, for example, a yoke 416, can be placed adjacent the recessed surface 426 when assembled. In the illustrated embodiment, the recessed surface 426 is above the elevated surface 428 and/or adjacent a top edge of the frame 410, while the elevated surface 428 is below the recessed surface 426 and/or adjacent a bottom edge of the frame 410. An inlet collar 430 projects outwardly (away from the user in use) from the exterior surface 412. The inlet collar 430 surrounds the fluid path 415. In the illustrated embodiment, a border between the recess surface 426 and the elevated surface 428 is partially defined by the inlet collar 430. The inlet collar 430 includes an inlet collar interior surface 432 (that defines the fluid path 415) and inlet collar surface 434 (located on an outside of the inlet collar 430). In some embodiments, the inlet collar surface 434 can be considered a part of or to partially define the exterior surface 412. In the illustrated embodiment, the inlet collar 430 includes a conduit retaining projection 436 (shown in FIG. 22). The inlet collar 430 can include one or more bias flow holes 438.

An outlet collar 440 projects inwardly (toward the user in use) from the interior surface 413. The outlet collar 440 has an outlet collar surface 444, which in some embodiments, can be considered a part of or to partially define the interior surface 413. The outlet collar 440 can include one or more seal retaining recesses 446. The seal retaining recesses 446 allow for interaction and/or connection between the frame 410 and the seal 406. In some embodiments, the seal retaining recess 446 allow for interaction and/or connection between the frame 410 and a clip that connects to the seal 406. In the illustrated embodiment, the outlet collar surface 444 includes the seal retaining recesses 446.

The fluid path 415 is defined or formed by the inlet collar 430 and the outlet collar 440. In use, the gas delivery conduit 408 is coupled to the inlet collar 430 and the seal 406 is coupled to the outlet collar 440. Gases can be delivered from the gas delivery conduit 408, through the fluid path 415 (i.e., through the inlet collar 430 and outlet collar 440), to the seal 406 to be delivered to the user.

In the illustrated embodiment, the inlet collar 430 can be oval and have a major axis 113 and a minor axis 111. In some embodiments, the inlet collar 430 can have a circular, triangular, "D", or other shape. In the illustrated embodiment, the frame 410 is symmetric about the minor axis 111 or vertical axis 105. In the illustrated embodiment, a major dimension $D_{major}$ (illustrated in FIG. 23B) of an aperture defined by the inlet collar 430 is 21.9 mm or approximately 21.9 mm, and a minor dimension $D_{minor}$ of the aperture is 16.7 mm or approximately 16.7 mm. In other words, a ration between the major dimension and the minor dimension is 1.31:1 or approximately 1.31:1.

In the illustrated embodiment, a lateral dimension (or a width) W of the frame 410 (illustrated in FIG. 23B) is 49.3 mm or approximately 49.3 mm. The ratio between the major dimension of the aperture defined by the inlet collar 430 and the lateral dimension W of the frame 410 is therefore 1:2.25 or approximately 1:2.25. The lateral dimension of the frame 410 can be selected to optimize or enhance the function of the frame 410 when assembled with the seal 406 and headgear 404. In some embodiments, the lateral dimension of the frame 410 can be in the range of 30 mm (or approximately 30 mm) to 75 mm (or approximately 75 mm).

In the illustrated embodiment, a vertical dimension (or a height) H of the frame 410 (illustrated in FIG. 23B) is 28.0 mm or approximately 28.0 mm. The ratio between the minor dimension of the aperture defined by the inlet collar 430 and the vertical dimension of the frame 410 is therefore 1:1.68 or approximately 1:1.68. One consideration in selecting the vertical dimension of the frame 410 is the area needed for the recessed surface 426 and/or headgear retaining features as described herein to maintain an effective connection between the frame 410 and the headgear 404. The vertical dimension of the frame 410 can be selected to provide adequate structure to enable the headgear 404 to connect effectively to the frame 410 and/or to provide adequate structural and rotational integrity required by the seal 406. In some embodiments, the vertical dimension of the frame 410 can be in the range of 20 mm (or approximately 20 mm) to 50 mm (or approximately 50 mm). The vertical dimension can be varied to accommodate different seal sizes, headgear profiles, and/or headgear connection methods or mechanisms.

In the illustrated embodiment, a proximal dimension (or a thickness) T of the frame 410 (illustrated in FIG. 26B) is 17.05 mm or approximately 17.05 mm. As shown in the side views of FIGS. 26A and 26B, an entirety of a periphery or distal end of the inlet collar 430 (in other words, a rim of the inlet collar 430 farthest away from the user in use) is not aligned with the illustrated vertical axis 105. Vertical extremes (in other words, the top and bottom) of the inlet collar 430 intersect the vertical axis, but central portions (in other words, sides or lateral extremes) of the inlet collar 430 are displaced proximally (or toward the user in use). In other words, when viewed from the side (as in FIGS. 26A-26B), the periphery of the inlet collar 430 is distally facing concave (or concave facing away from the user in use). The concave profile can advantageously allow the frame 410 to have reduced material requirements. In some embodiments, the oval shape of the inlet collar 430 and/or the offset vertical and lateral extremes of the distal end of the inlet collar 430 provide beneficial behavior when a gas delivery conduit, such as gas delivery conduit 408, is coupled to the inlet collar 430. For example, if the gas delivery conduit 408 is removably coupled to the inlet collar 430, for example, via a press fit, snap fit, or other connection that cooperates with the conduit retaining projection 436, it can be difficult to unintentionally remove the gas delivery conduit 408 if a force is applied axially (in an axial direction of the inlet collar 430 and/or gas delivery conduit 408). The oval shape and/or concave distal end of the inlet collar 430 can therefore inhibit unintentional removal of the gas delivery conduit 408. However, the gas delivery conduit can be detached from the frame 410 more easily or with less effort if the gas delivery conduit is twisted about the axial axis of the inlet collar 430.

Figure 24A:
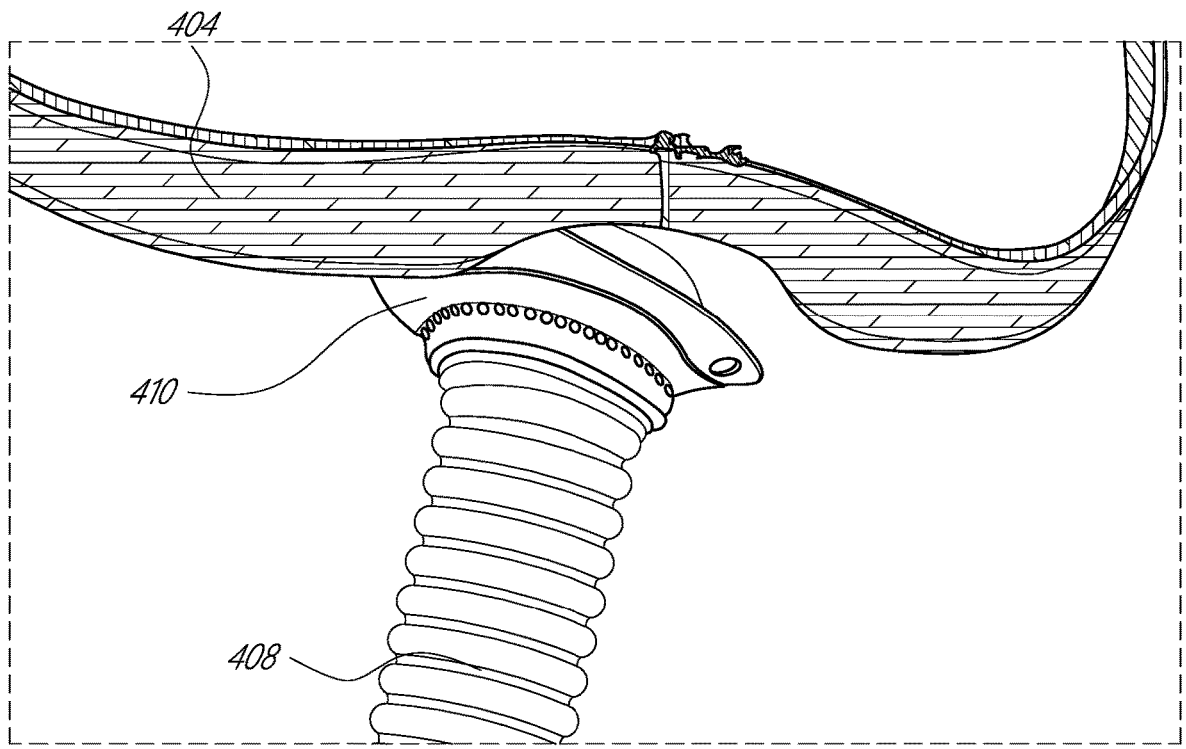
FIGS. 24A-24B show a method of coupling a headgear of the respiratory mask of FIG. 20 to the frame of FIG. 21.
Figure 24B:
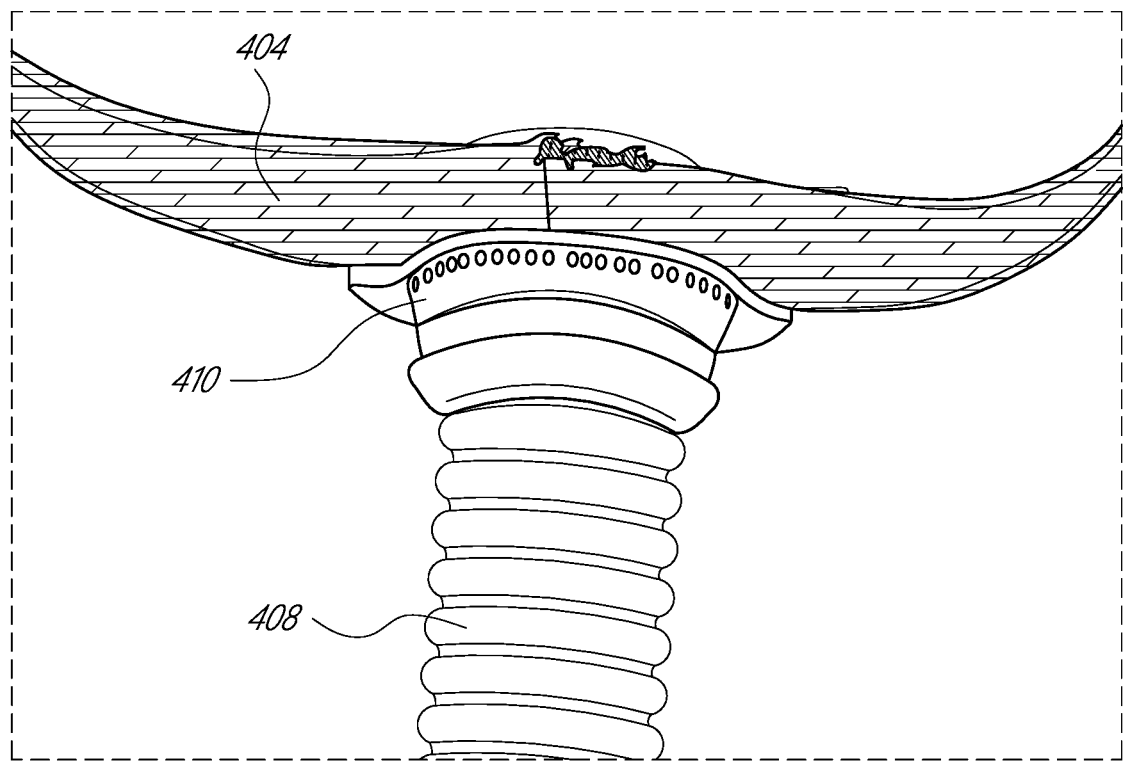
Figure 24C:
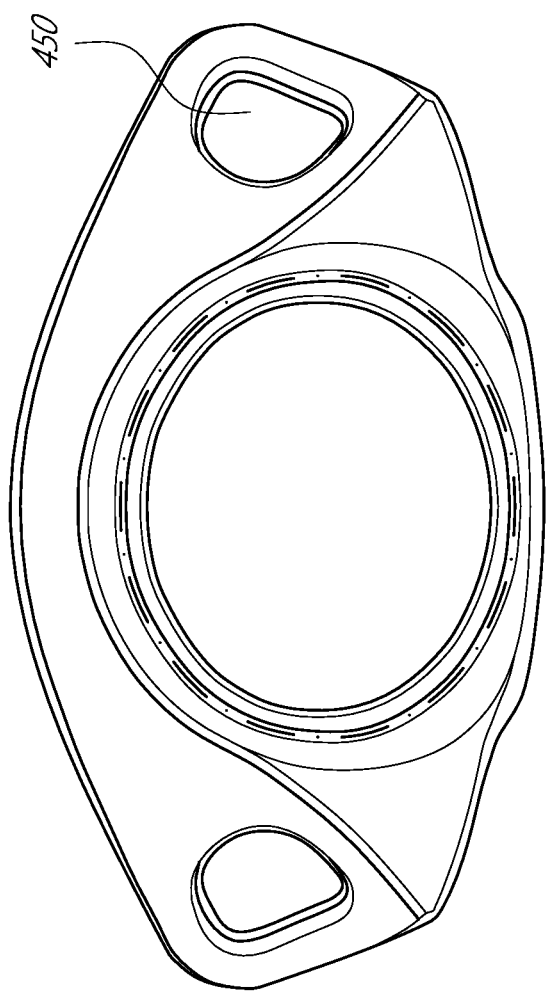
FIG. 24C is a front view of an alternative embodiment of the frame of FIG. 21.
Figure 24D:
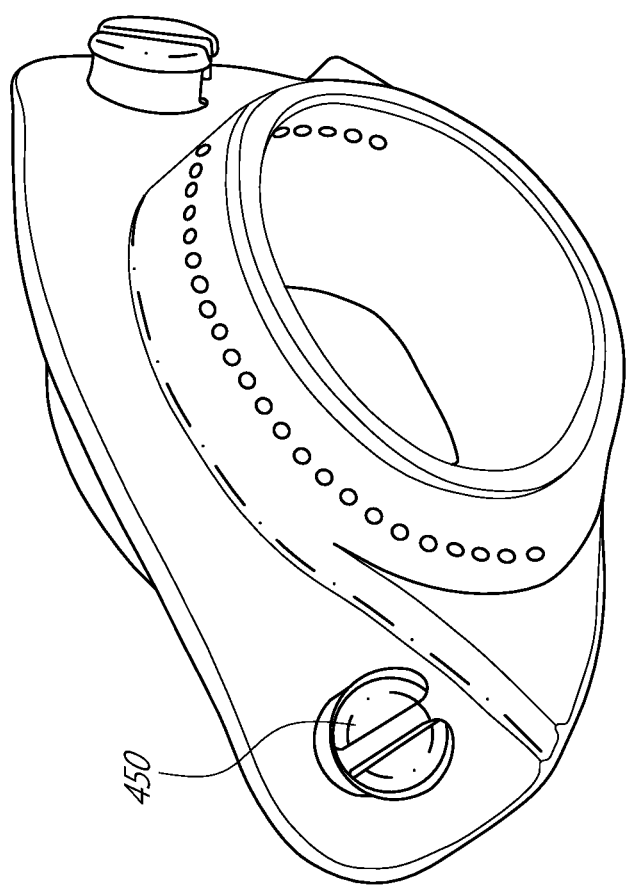
FIG. 24D is a front perspective view of an alternative embodiment of the frame of FIG. 21.
Figure 25:
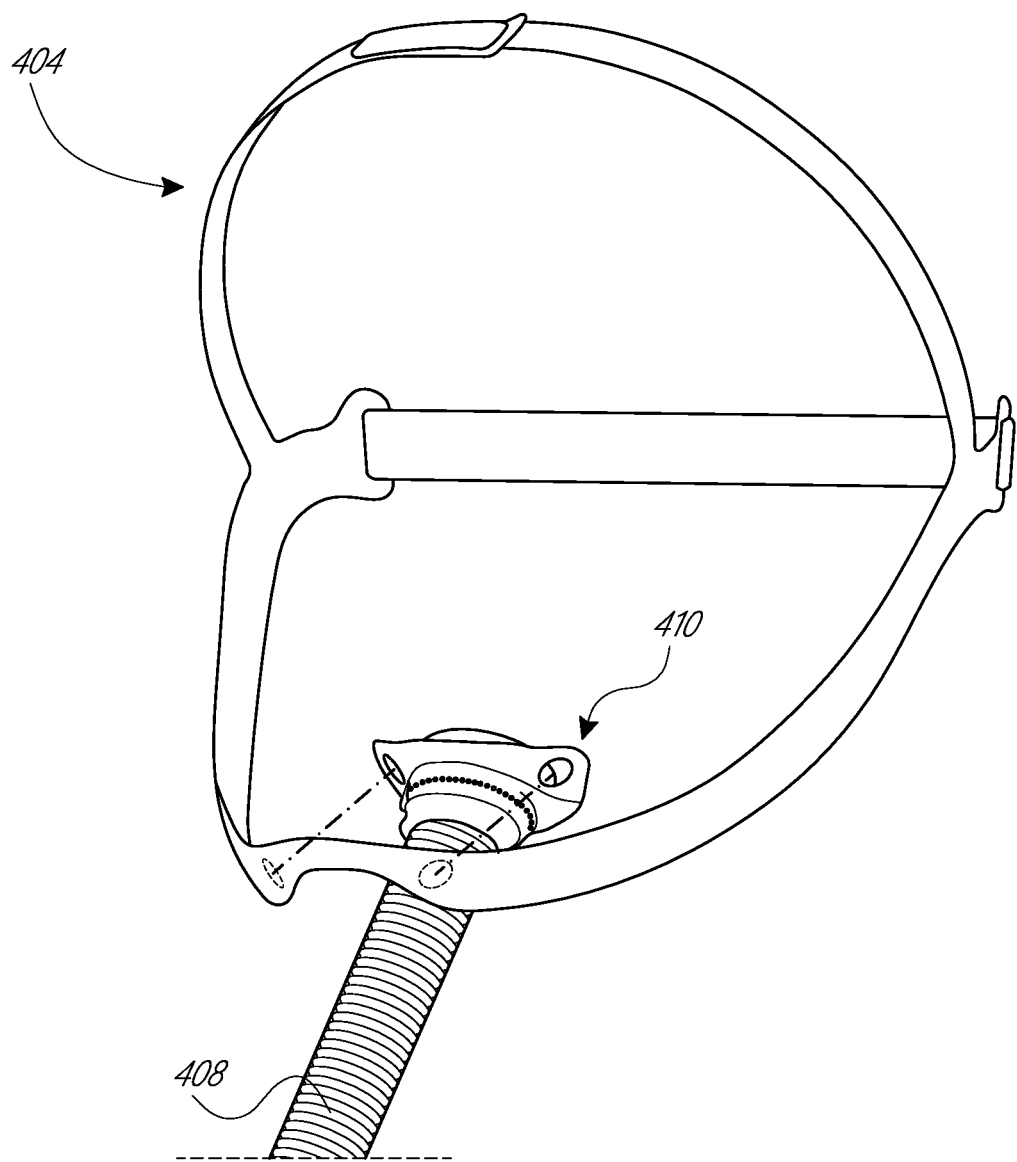
FIG. 25 is a perspective partially exploded view of the respiratory mask of FIG. 20.

The frame 410 can include various headgear retaining features. The retaining features are used to couple the frame 410 to the headgear 404 as shown in FIG. 25. In the illustrated embodiment of FIGS. 21-23B, the frame 410 includes two retaining features 450 located in the recessed surface 426. More or fewer retaining features 450 are also possible. As shown, each retaining features 450 is displaced laterally with respect to or spaced laterally from the vertical axis, with one of the retaining features 450 on each side of the vertical axis. In the illustrated embodiment, the retaining features 450 are circular holes. In some embodiments, the retaining features 450 are holes having an oval, rectangular, "D" (for example, as shown in FIG. 24C), or other shape. In some embodiments, the two retaining features 450 are different from each other. Differing shapes for the right and left headgear retaining features 450 can help guide the user in properly connecting the headgear 404 to the frame 410. In some embodiments, the headgear retaining features 450 have anti-rotation shapes and/or features. The headgear 404 can include projections that correspond to the retaining features 450 and are designed to fit into the retaining features 450. The projections can be secured to the retaining features 450 and the frame 410 via a snap-fit or other suitable means. In some embodiments, the retaining features 450 can be structures projecting outwardly from the recessed surface 426, for example as shown in FIG. 24D. In some such embodiments, the headgear 404 can include corresponding holes that receive the retaining features 450. In the illustrated embodiment, each of the retaining features 450 is a circular projection with a central channel that extends between and/or divides the retaining feature 450 into two semi-circular or approximately semi-circular sides or portions. The projections can be secured to correspondingly sized holes in the headgear 404 via a snap fit or other suitable means. In some embodiments, the retaining features 450 can includes one or more magnets or a magnetic material that attract to one or more magnets or magnetic material in the headgear 404.

As described above, in the illustrated embodiment the frame 410 includes two retaining features 450. The inclusion of two retaining features 450 and/or the use of circular retaining features 450 can advantageously allow for ease of donning and doffing the headgear 404 from the frame 410. As shown in FIG. 24A, a first of the retaining features 450 can be used to connect the frame 410 and headgear 404 at an angle. The frame 410 can then be rotated about the first retaining feature 450 so that a second of the retaining features 450 can be connected to the headgear 404 as shown in FIG. 24B.

Figure 28:
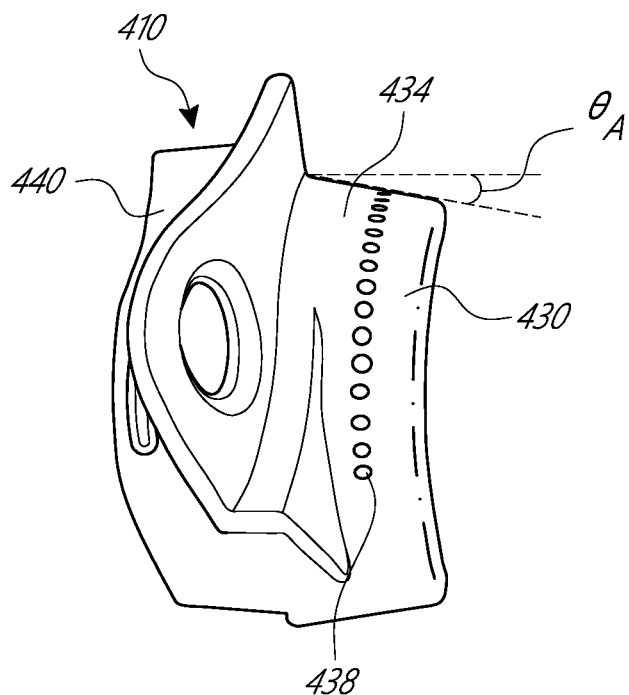
FIG. 28 is a side view of the frame of FIG. 21.
Figure 29A:
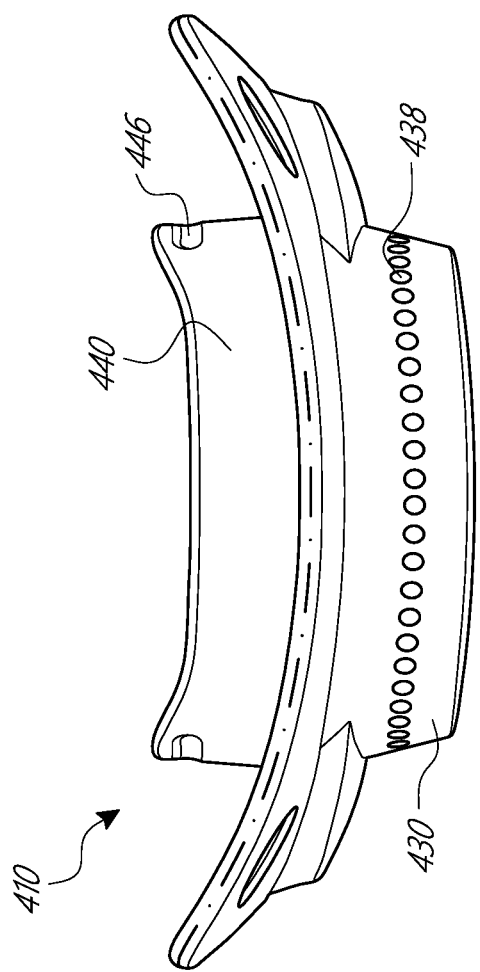
FIG. 29A is a top view of the frame of FIG. 21.
Figure 29B:
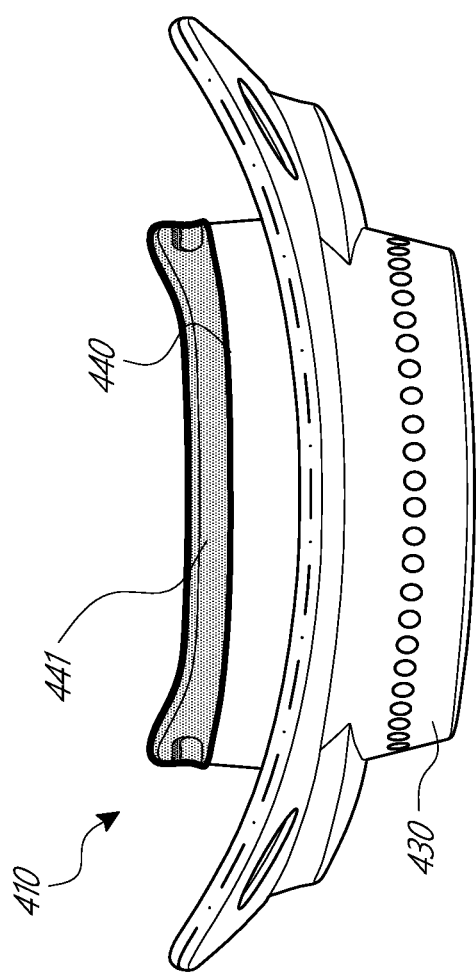
FIG. 29B is a top view of an alternative embodiment of the frame of FIG. 29A.
Figure 29C:
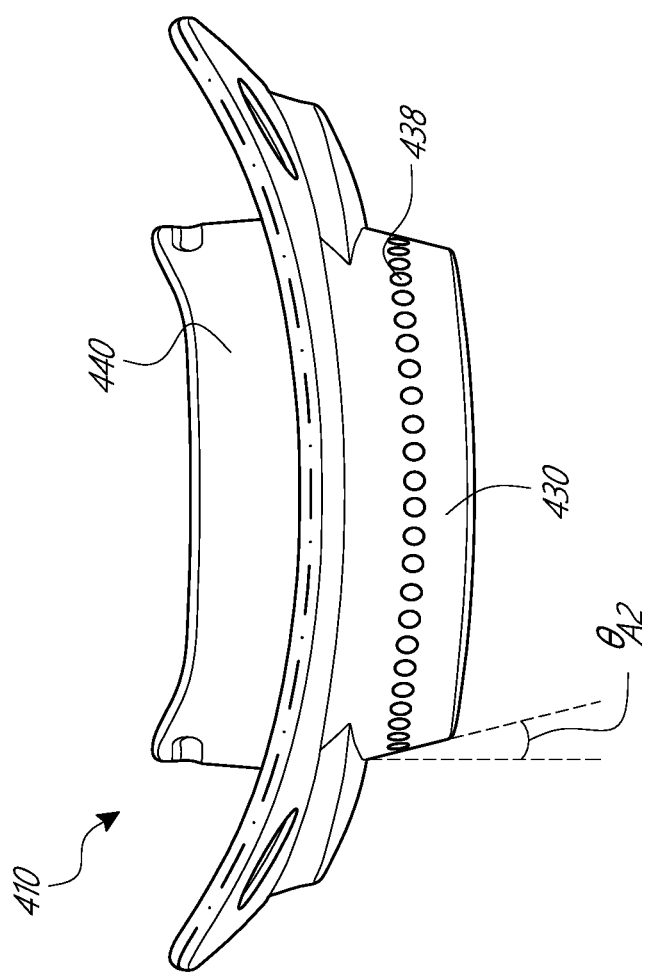
FIG. 29C is a top view of the frame of FIG. 21.
Figure 30:
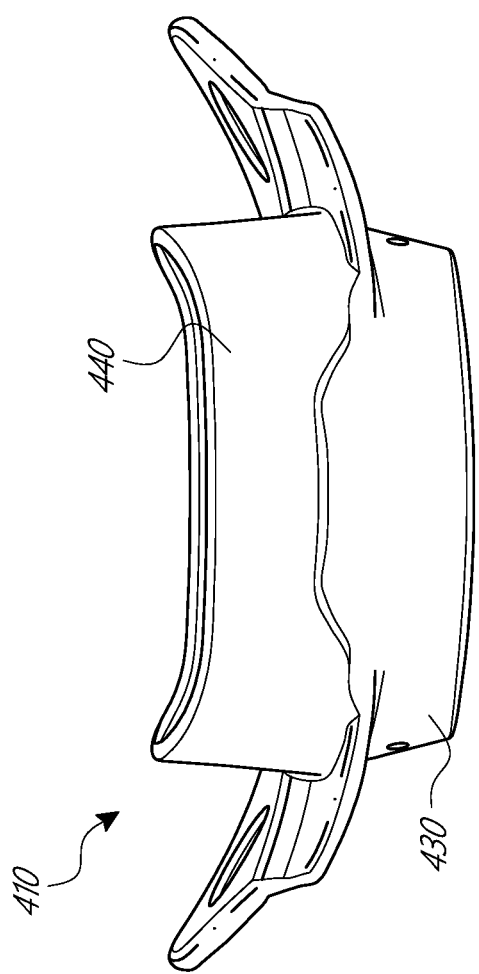
FIG. 30 is a bottom view of the frame of FIG. 21.

In the illustrated embodiment, the inlet collar 430, or the inlet collar surface 434, is angled by an angled surface angle $\theta_A$ such that a diameter of a base of the inlet collar 430 nearest the user in use is greater than a diameter of the periphery of the inlet collar 430 farthest away from the user in use, as shown in FIGS. 28 and 29C. The inlet collar 430 may resemble a hollow frustum. The angle of the inlet collar 430 causes or allows air passing through the bias flow holes 438 (generally or approximately perpendicularly to the angled inlet collar 430 or inlet collar surface 434) to be directed away from the user's face. This advantageously prevents or reduces the likelihood of the user feeling a draft resulting from air flow through the bias flow holes 438 and/or entrainment.

A first angled surface angle can be defined as the angle between the top (or upper vertical extreme) of the inlet collar 430, or inlet collar surface 434, and an axis parallel to the proximal axis and located at an intersection of the inlet collar 430 and the exterior surface 412 or recessed surface 426 of the frame 410 as shown in FIG. 28. A second angled surface angle $\theta_{A2}$ can be defined as the angle between the lateral side of the inlet collar 430, or inlet collar surface 434, and an axis parallel to the proximal axis and located at an intersection of the inlet collar 430 and the exterior surface 412 or elevated surface 428 of the frame 410 as shown in FIG. 29C. In some embodiments, the angled surface angles can be in the range of approximately 10° to about 15°. In the illustrated embodiment, the first angled surface angle is approximately 10°, the second angled surface angle is approximately 15°, and the angled surface angle transitions from approximately 10° to about 15° between the top and side of the inlet collar 430. In some embodiments, the angled surface angle can be constant around the entirety of the inlet collar 430. In some embodiments, the angled surface angle can vary around the inlet collar 430. In some embodiments, the angled surface angle can be in the range of approximately 0° to approximately 90°, for example, approximately 0°, approximately 45°, or approximately 90°.

In the illustrated embodiment, each bias flow hole 438 is displaced or spaced equally from the distal end of the inlet collar 430. In other words, an arrangement of the bias flow holes 438 follows the profile of the distal end or periphery of the inlet collar 430, with bias flow hole(s) 438 located at or proximate a vertical extreme (top or bottom) of the inlet collar 430 being distal to or farther away from the user in use than bias flow hole(s) 438 located at or proximate lateral sides of the inlet collar 430. In some embodiments, an arc connecting the bias flow hole(s) 438 is parallel or generally parallel to the periphery of the inlet collar 430. Maintaining a constant and controlled distance between the bias flow holes 438 and the periphery of the inlet collar 430 can allow for better and easier control of noise produced by flow through the bias flow holes 438. The distance between the bias flow holes 438 and the periphery of the inlet collar 430 can be selected to reduce or minimize noise produced by flow through the bias flow holes 438. In the illustrated embodiment, the bias flow holes 438 are positioned 3.1 mm or approximately 3.1 mm from the periphery of the inlet collar 430. In the illustrated embodiment, the bias flow holes 438 are located at or approximately at a mid-point of a length of the inlet collar 430.

Figure 26A:
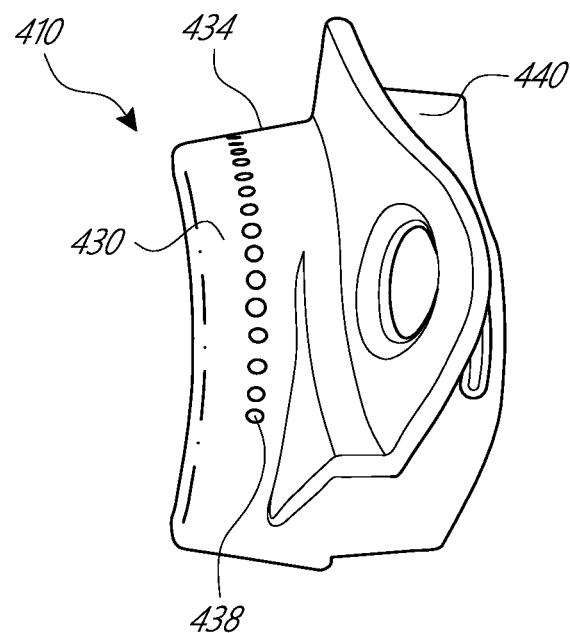
FIG. 26A is a side view of the frame of FIG. 21.
Figure 26B:
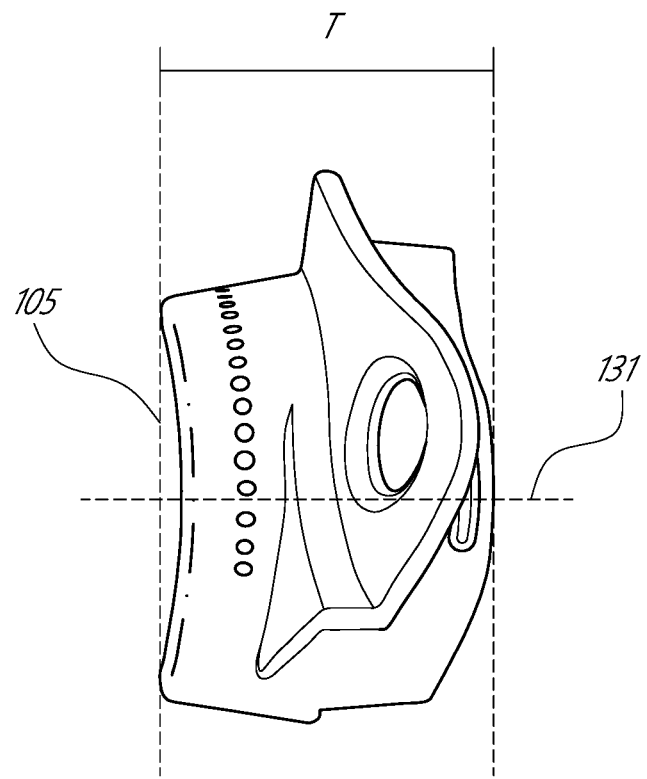
FIG. 26B is a side view of the frame of FIG. 21 showing various axes and dimensions.
Figure 26C:
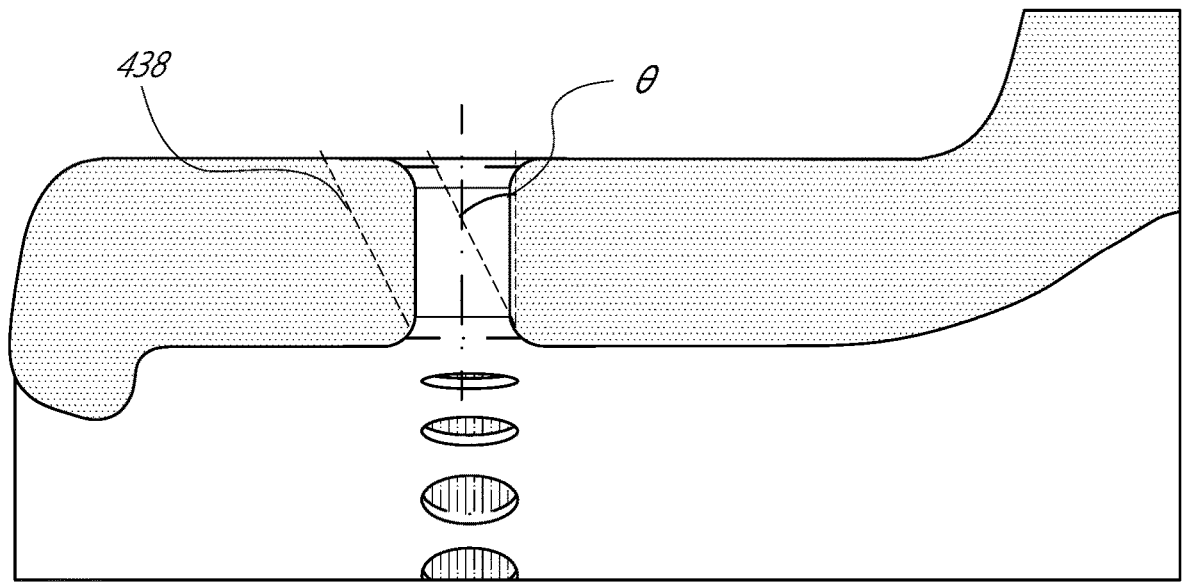
FIG. 26C is a partial section view of an inlet collar of the frame of FIG. 21.
Figure 26D:
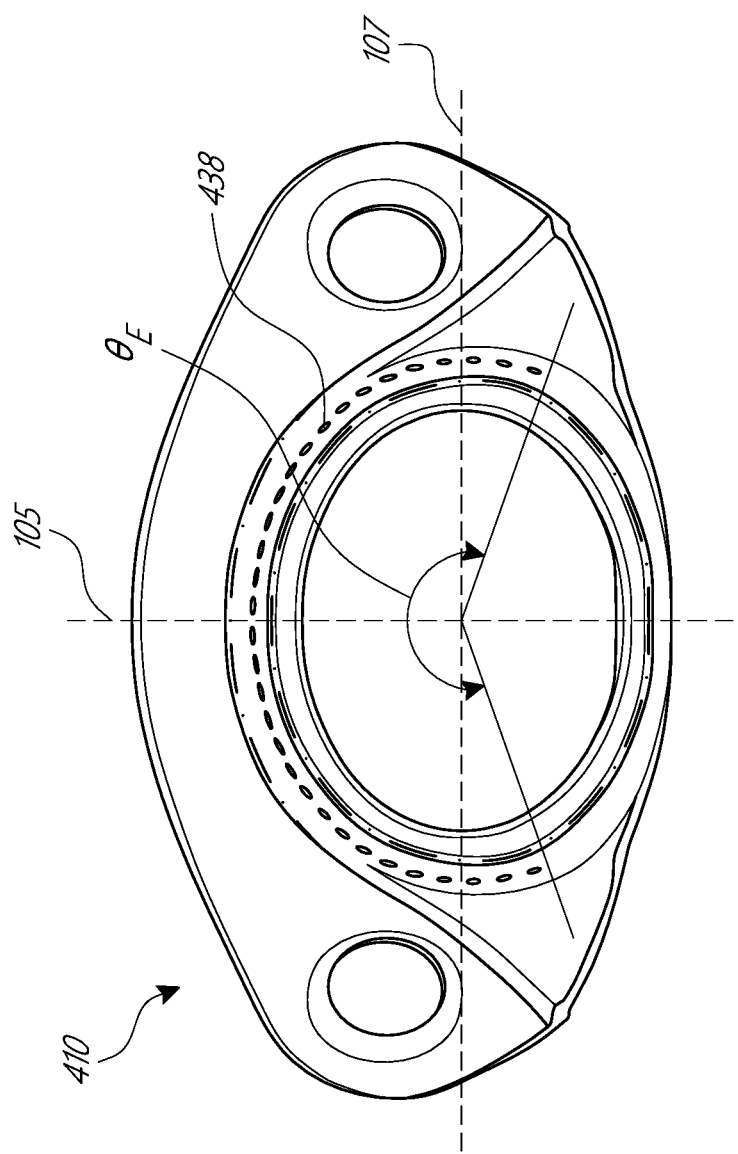
FIG. 26D is a front view of the frame of FIG. 21.

In the illustrated embodiment, as shown in FIG. 26D, bias flow holes 428 are disposed about or in a portion of the inlet collar 430. The portion of the inlet collar 430 including bias flow holes 428 can be defined by an exhaust angle $\theta_E$, which is defined with respect to an origin centered at the intersection of the vertical axis 105 and the lateral axis 107 of the inlet collar 430 as shown. In some embodiments, the exhaust angle and/or the bias flow holes 428 can span from approximately 4:00 to approximately 8:00 (as on a clock). In some embodiments, the exhaust angle and/or the bias flow holes 428 can span from approximately 5:00 to approximately 7:00 or from approximately 3:00 to approximately 9:00. In some embodiments, the exhaust angle can be approximately 220°, approximately 218°, in the range of approximately 180° to approximately 270°, in the range of approximately 190° to approximately 260°, in the range of approximately 200° to approximately 250°, in the range of approximately 210° to approximately 240°, or in the range of approximately 220° to approximately 230°. In some embodiments, the exhaust angle can be 360°. In other words, in some embodiments, the bias flow holes 428 can span the circumference of or entirely encircle the inlet collar 430.

As shown in FIG. 26C, in the illustrated embodiment, the bias flow holes 438 extend through the inlet collar 430 perpendicularly or approximately perpendicularly to the inlet collar surface 434 and/or the inlet collar interior surface 432. In some embodiments, as indicated by the dashed lines in FIG. 26C, the bias flow holes 438 can extend through the inlet collar 430 at an angle θ relative to perpendicular. Angle θ can be in the range of approximately ±10° to approximately ±45°, for example, ±10°, ±25°, or ±45°. As illustrated, bias flow holes 438 oriented at a positive angle extend such that the hole is closer to the periphery of the inlet collar 430 on the inlet collar surface 434 than on the inlet collar interior surface 423. Angles greater than or equal to 0 can advantageously direct flow through the bias flow holes 438 away from the user in use.

Figure 27A:
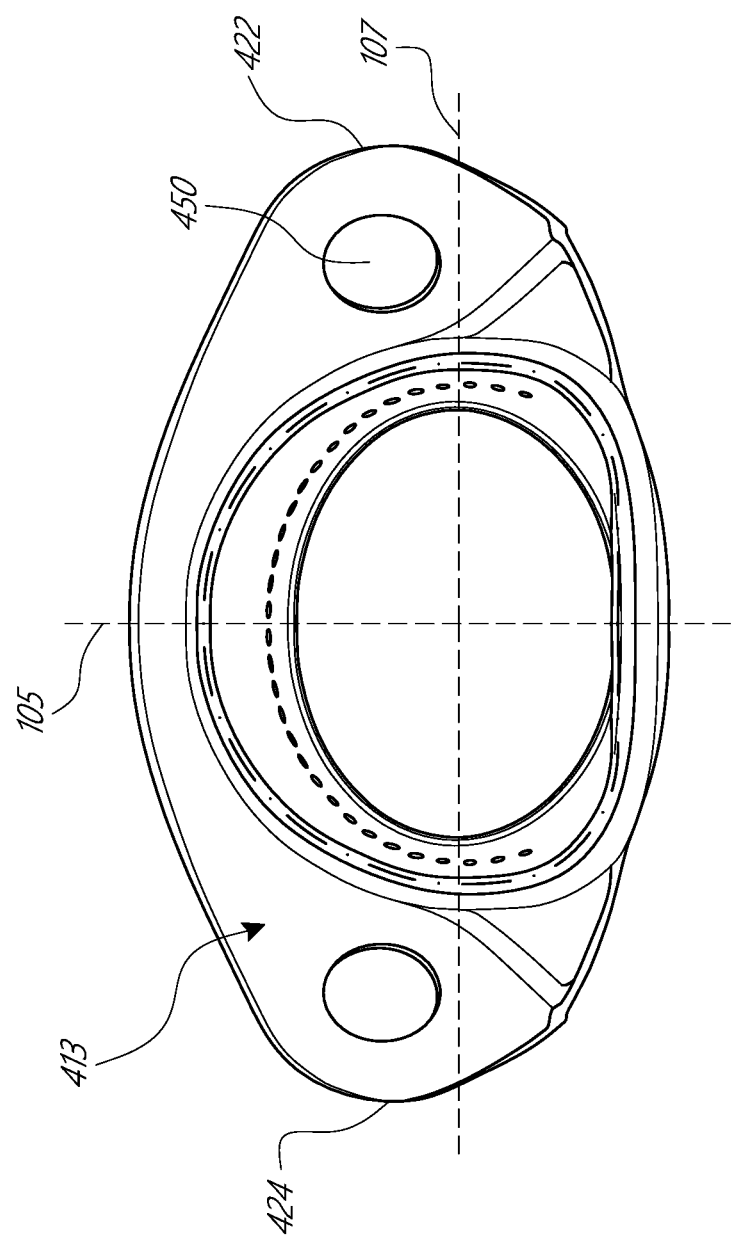
FIG. 27A is a rear view of the frame of FIG. 21 showing various axes.
Figure 27B:
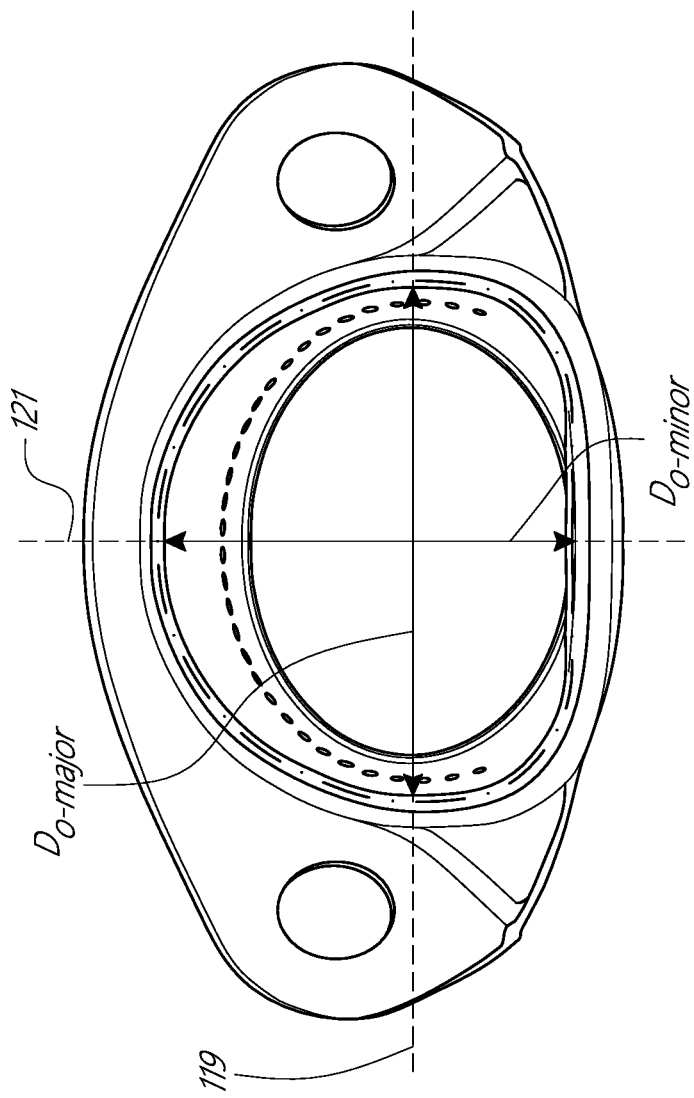
FIG. 27B is a rear view of the frame of FIG. 21 showing various axes and dimensions.

As shown in FIG. 27B, the outlet collar 440 has a major axis 119 and a minor axis 121. In the illustrated embodiment, the outlet collar 440 has a "D" shape. A major axis dimension $D_{o\text{-}major}$ of the outlet collar 440 is the dimension of an aperture defined by a proximal-most end or edge of the inlet collar 440 along the major axis 119 at a position at which the aperture has a maximum lateral dimension. In some embodiments, the outlet collar 440 can have a circular, triangular, or other shape. A minor axis dimension $D_{o\text{-}minor}$ of the outlet collar 440 is the dimension of the aperture along the minor axis 121, which is parallel and/or aligned with the vertical axis, shown in FIG. 27A, in the illustrated embodiment. As shown in FIG. 27A, the vertical axis and lateral axis intersect at an origin at or corresponding to the center of the aperture of the inlet collar 430. In the illustrated embodiment, the outlet major axis corresponds to or is located at the same position as the lateral axis. In some embodiments, the outlet major axis can be vertically displaced or spaced from the lateral axis. In other words, in some embodiments, a center of the aperture of the inlet collar 430 is offset from a center of the aperture of the outlet collar 440.

In the illustrated embodiment, the outlet major axis dimension $D_{o\text{-}major}$ is 25.9 mm or approximately 25.9 mm, and the outlet minor axis dimension $D_{o\text{-}minor}$ is 20.7 mm or approximately 20.7 mm. In other words, a ratio between the outlet major axis dimension $D_{o\text{-}major}$ and the outlet minor axis dimension $D_{o\text{-}minor}$ is 1.25:1 or approximately 1.25:1. In the illustrated embodiment, the aperture of the outlet collar 440 is larger than the aperture of the inlet collar 430.

In some embodiments, the outlet collar 440 or a portion of the outlet collar 440, e.g., a rim 441 of the outlet collar in the illustrated embodiment, is a different color compared to other portions of the frame 410. In some embodiments, the majority of the frame 410 can be transparent, and the outlet collar 440 or a portion of the outlet collar 440 can be a transparent blue color. In some embodiments, the majority of the frame 410 can be transparent, and the outlet collar 440 or a portion of the outlet collar 440 can be opaque. In some embodiments, the majority of the frame 410 can be opaque and the outlet collar 440 or a portion of the outlet collar 440 can be transparent. The different color (and/or transparency) of the outlet collar 440 or portion thereof can advantageously provide an indication to the user that the outlet collar 440 is designed to engage with another component of the assembly, e.g., a clip of the seal 406, in use. As shown in FIG. 29B, a proximal rim 441 extending to a certain depth of the outlet collar 440 can have a different color. In some embodiments, the different color can be produced using a Pad Printing process. In some embodiments, the inlet collar 430 or a portion of the inlet collar 430 is a different color compared to other portions of the frame 410. In some embodiments, the outlet collar 440 and/or inlet collar 430 can be made from a material that differs in at least one property from a material of the majority of the frame 410 or of other portion(s) of the frame 410. For example, the outlet collar 440 can be made from a material that differs in at least one property from a material of the inlet collar 430. In such an embodiment, the frame 410 can be formed using, for example, a two-shot molding, co-molding, or over-molding process. In some embodiments, the frame 410 can be formed using a two-shot molding, co-molding, or over-molding process even if the frame 410 is made of a single material and/or the material of the inlet collar 430 does not differ from a material of the outlet collar 440.

Figure 31:
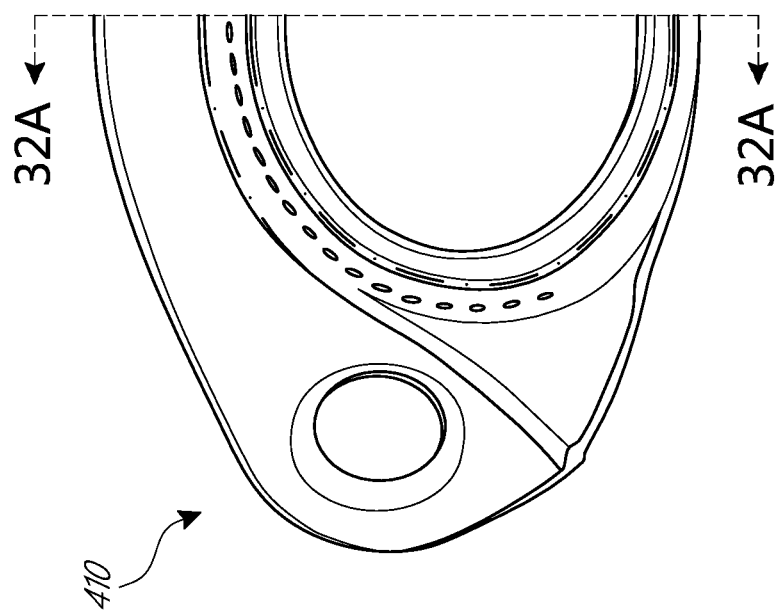
FIG. 31 is a partial front view of the frame of FIG. 21 showing a section plane.
Figure 32A:
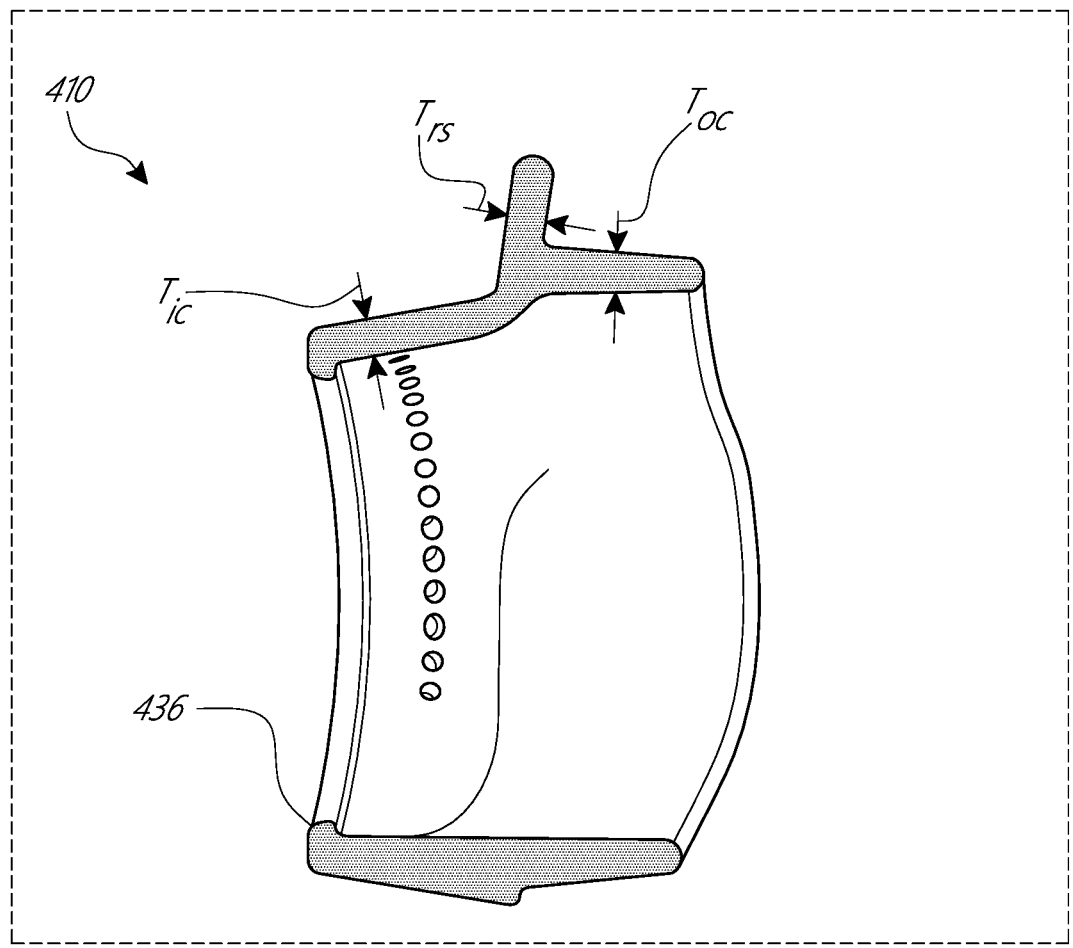
FIG. 32A is a section view of the frame of FIG. 21 taken along line 32A-32A in FIG. 31.
Figure 32B:
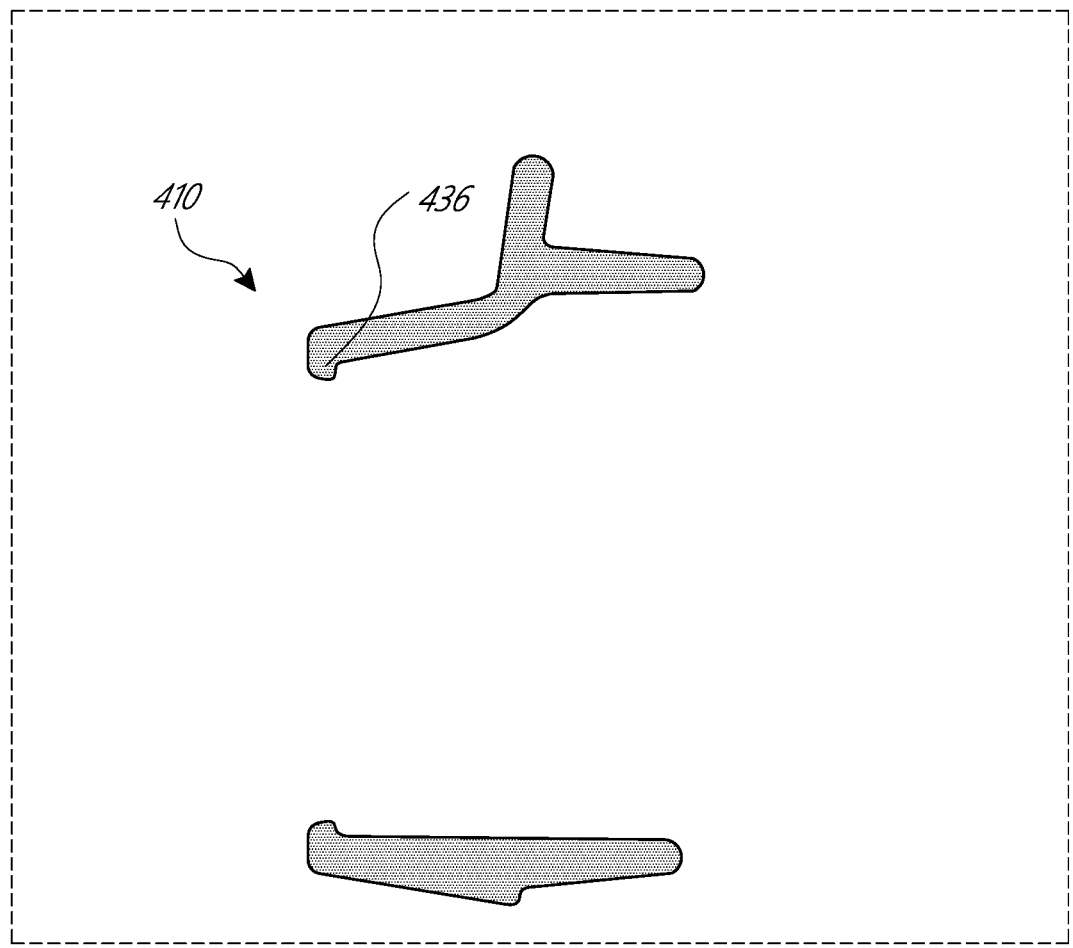
FIG. 32B is a 2D view of the section of FIG. 32A.

FIG. 32A illustrates a section view taken along line 32A-32A in FIG. 31. The section line is centrally located with respect to the frame 410 and is aligned with the vertical axis. FIG. 32B illustrates a 2D view of the section of FIG. 32A. A thickness of the frame 410, or thicknesses of various parts of the frame 410, can be selected to provide sufficient rigidity to the frame 410 in use while reducing or minimizing the weight and/or profile of the frame 410. In some embodiments, the recessed surface 426 (or the frame 410 in the region of the recessed surface 426) has a thickness $t_{rs}$ of 1.5 mm or approximately 1.5 mm. In some embodiments, the inlet collar 430 has a thickness $t_{ic}$ of 1.46 mm or approximately 1.46 mm. In some embodiments, the conduit retaining projection 436 projects inwardly from the inlet collar interior surface 432 0.5 mm or approximately 0.5 mm. In the illustrated embodiment, the conduit retaining projection 436 extends around an entirety of the periphery of the inlet collar 430. In some embodiments, the outlet collar 440 has a thickness $t_{oc}$ of 1.5 mm or approximately 1.5 mm. Other thicknesses for the inlet collar 430, recessed surface 426 (or frame 410 in the region of the recessed surface 426), and/or outlet collar 440 are also possible. In some embodiments, the frame 410 is made of or includes Nylon 12. Altering characteristics of the compound can allow the frame 410 to exhibit the same or similar rigidity when the inlet collar 430, recessed surface 426 (or frame 410 in the region of the recessed surface 426), and/or outlet collar 440 have thicknesses in the range of 0.6 mm or approximately 0.6 mm to 2 mm or approximately 2 mm or greater than 2 mm.

Alternative Headgear Embodiment

Figure 34:
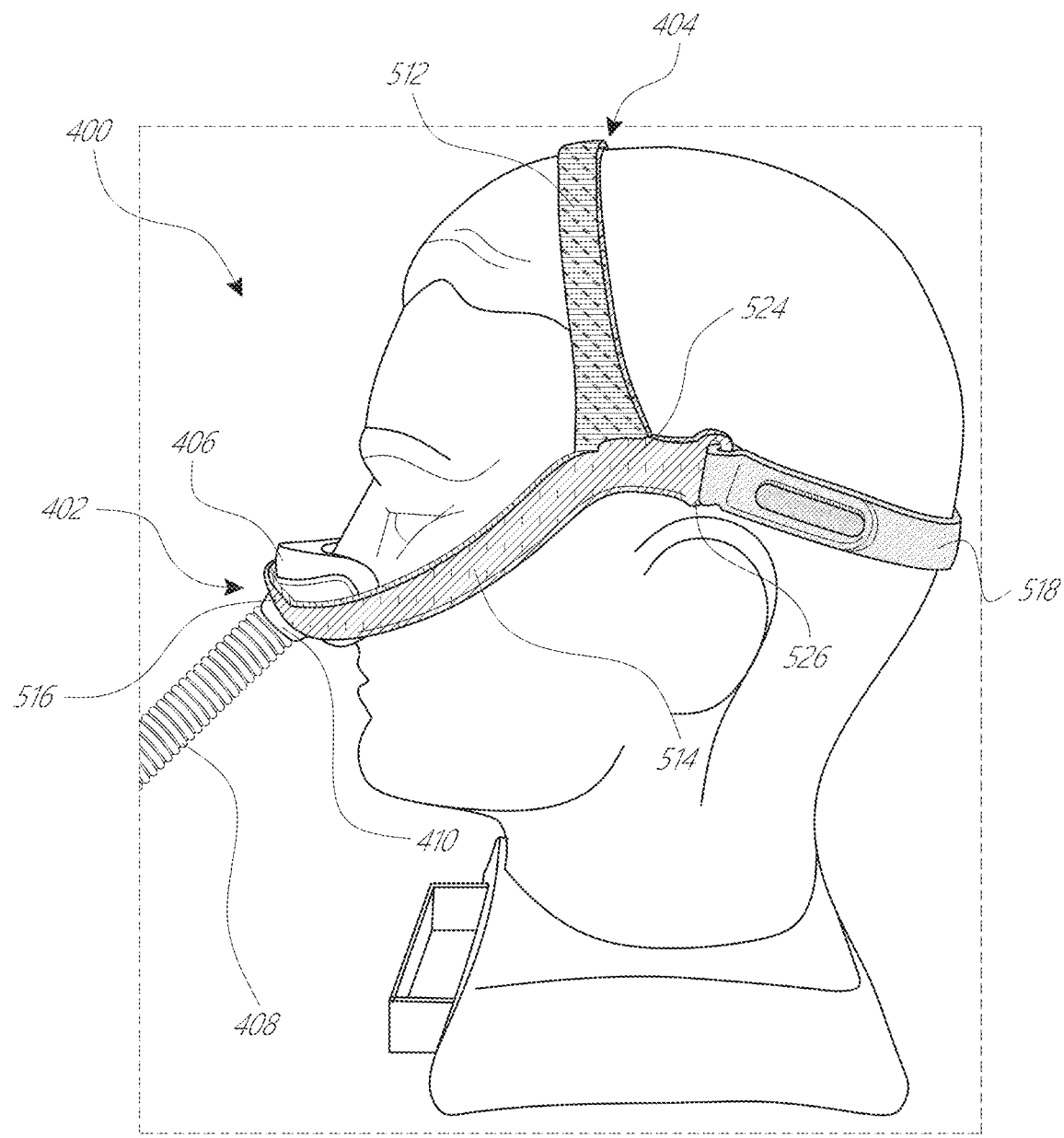
FIG. 34 is a side view of the respiratory mask of FIG. 33 as worn by a user.

FIGS. 33-34 show an exemplary embodiment of the headgear 404 that can be used with frame 410. In the illustrated embodiment, the headgear 404 has a bifurcated configuration. The headgear 404 can be similar to the headgear 204 in some ways. Features of the headgear 404 that are the same as or similar to corresponding features of the headgear 204 are indicated by reference numerals that are the same plus 300 herein (e.g., the headgear 404 includes a top strap 512, a pair of opposing side arms 514, a yoke 516, and a rear strap 518). The top strap 512 and rear strap 518 form the bifurcated configuration.

Figure 37:
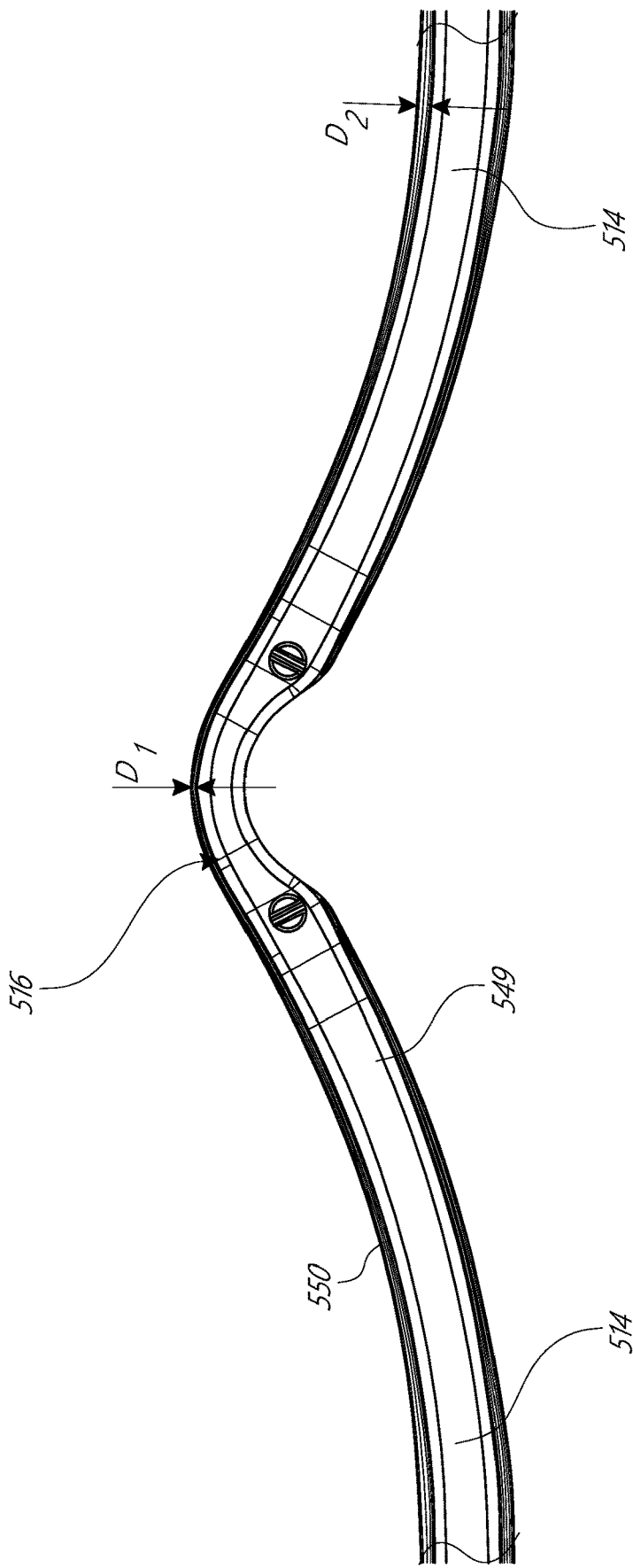
FIG. 37 is a front view of the yoke and portions of side arms of the headgear of the mask of FIG. 33.

The side arms 514 and/or top strap 512 can include a core 549 and an outer casing 551. In some embodiments, the core is made of or includes a plastic material. In some embodiments, the outer casing is or includes a textile. The outer casing can be permanently bonded to the core. A textile outer casing can advantageously provide a soft and comfortable finish for contacting the user in use. A longitudinal edge portion of the outer casing 551 that protrudes from edges of the core 549 and is not filled by the core 549 can form a soft edge 550 as shown in FIG. 37. Soft edges 550 can advantageously provide a cushioned edge that can improve user comfort, for example, by softening potential contact between edges of the top strap 512 and/or side arms 514 and the user's head. In some cases, having a cushioned edge can be of particular benefit on a lower edge of the side arms 514 that sit above the user's ears in use. A thickness of the soft edge 550 can vary along a length of each side arm 514. In the illustrated embodiment, the thickness of the soft edge 550 varies from a maximum of 2 mm or approximately 2 mm at lateral ends of the side arms 514 (indicated by $D_2$ in FIG. 37) to a minimum of 1 mm or approximately 1 mm on an upper ridge of the yoke 516 (indicated by $D_1$ in FIG. 37). In some embodiments, a lower edge of the yoke 516 does not include a soft edge, for example, because the lower edge of the yoke 516 is not intended to be in contact with the user's face in use, for aesthetic and/or industrial design benefits, to allow for tolerances between parts, and/or other reasons. The omission of a soft edge in this region provides additional space to allow for increasing a thickness of the core 549 of the yoke 516 to improve or increase the structural integrity of that region.

Figure 35A:
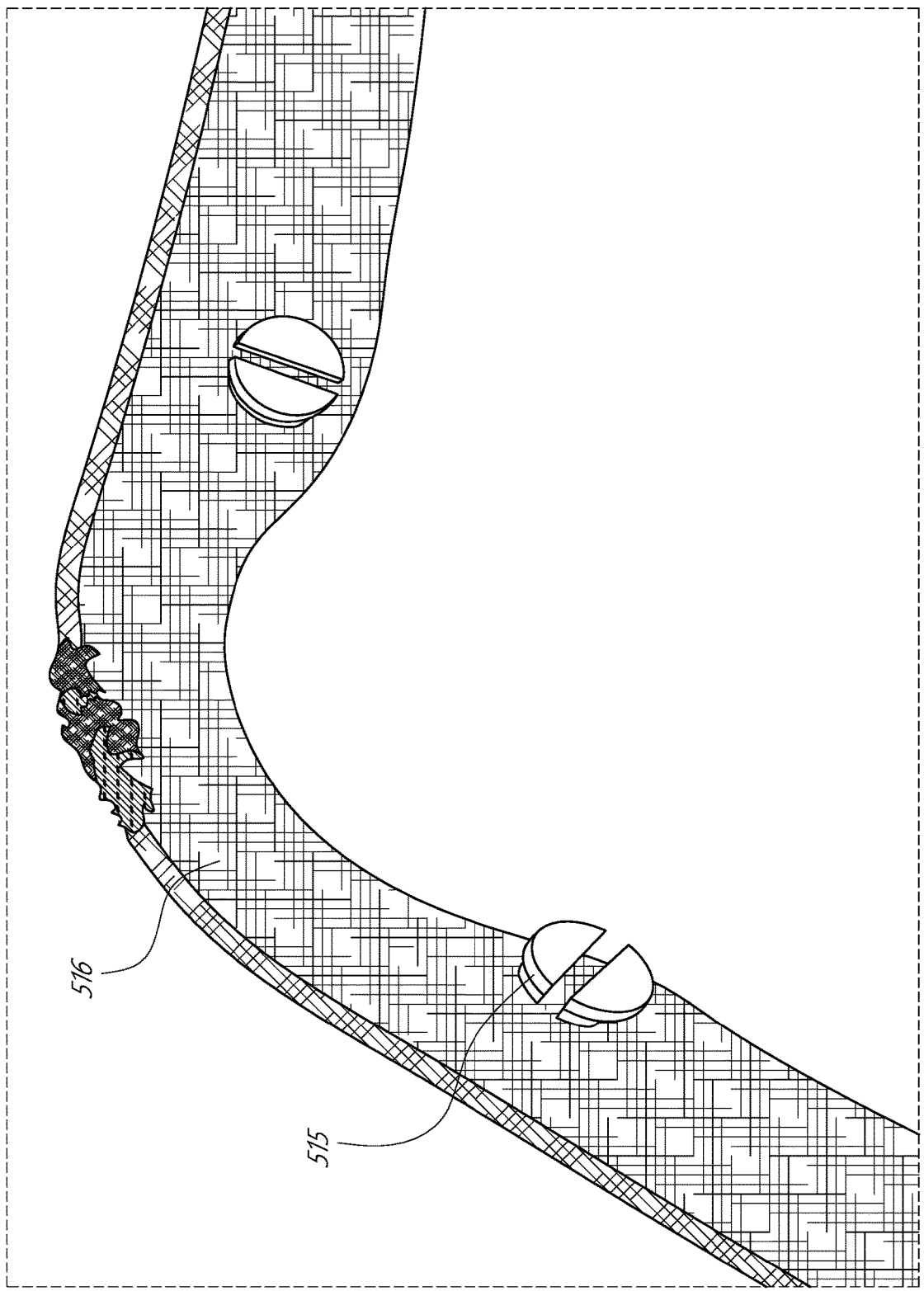
FIG. 35A is a rear view of a yoke of a headgear of the mask of FIG. 33.
Figure 35B:
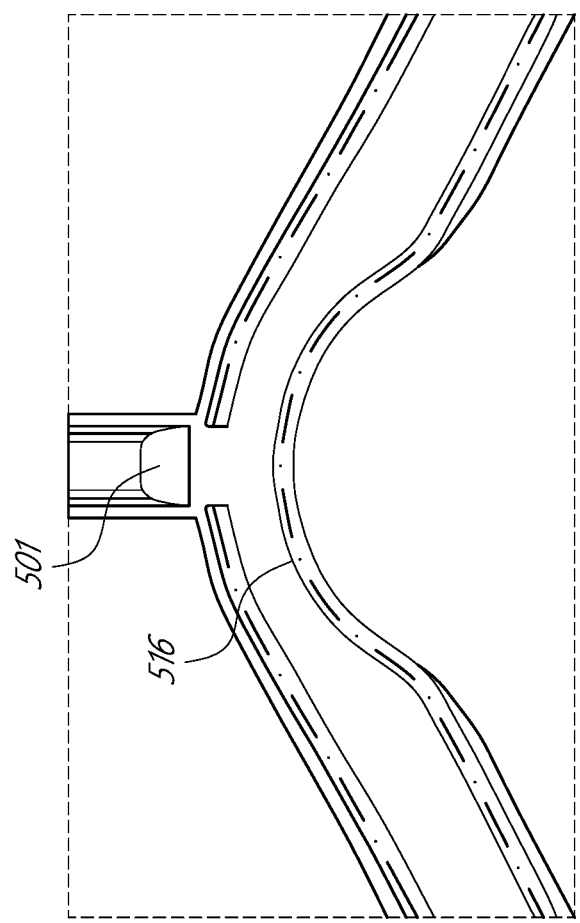
FIG. 35B is a rear view of the yoke of the headgear of the mask of FIG. 33 showing a gate used in molding.

In the illustrated embodiment, the outer casing 551 is made of a textile that is a non-stretch or low-stretch yarn. A non-stretch or low-stretch yarn requires a relatively high force for elastic deformation. In some cases, yarns having a high elasticity perform poorly (or worse compared to yarns having a lower elasticity) in an intra-molding process used to form the top strap 512 and/or side arms 514 as the yarn fibers may stretch to an extent that the molten plastic can escape outside of the outer casing. Using a non-stretch or low-stretch yarn for the side arm 514 outer casing advantageously improves the finish and/or consistency of the finished side arms 514. A non-stretch or low-stretch yarn reduces or minimizes the amount or degree to which the fibers of the yarn can stretch, which can prevent or reduce the likelihood of the plastic stretching and escaping from the textile outer casing during the intra-molding process. The use of a non-stretch or low-stretch yarn can therefore also help improve the reliability of the manufacturing process. In some embodiments, the textile outer casing can be made of or include a yarn having a degree of elasticity. A yarn having a low elasticity (i.e., that requires a relatively high force to elastically stretch) may perform adequately in the molding process. In some embodiments, a gate 501 for the molding process is located at or near a central point on the yoke 516 of the headgear 404 as shown in FIG. 35B.

Figure 36A:
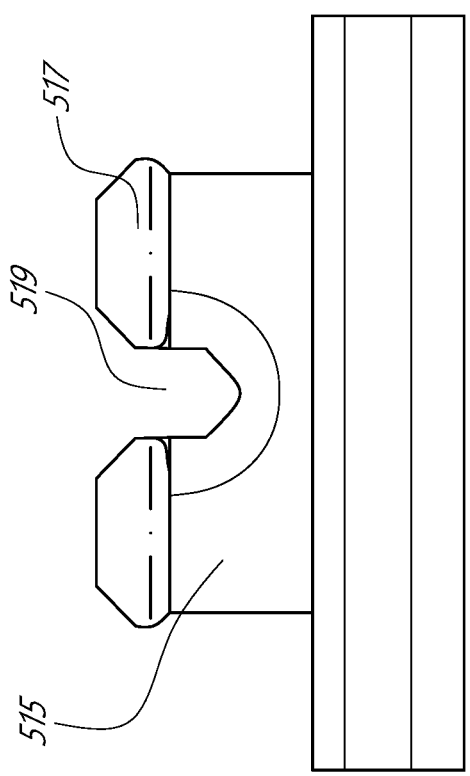
FIG. 36A is a side view of a frame retaining feature of the headgear of the mask of FIG. 33.
Figure 36B:
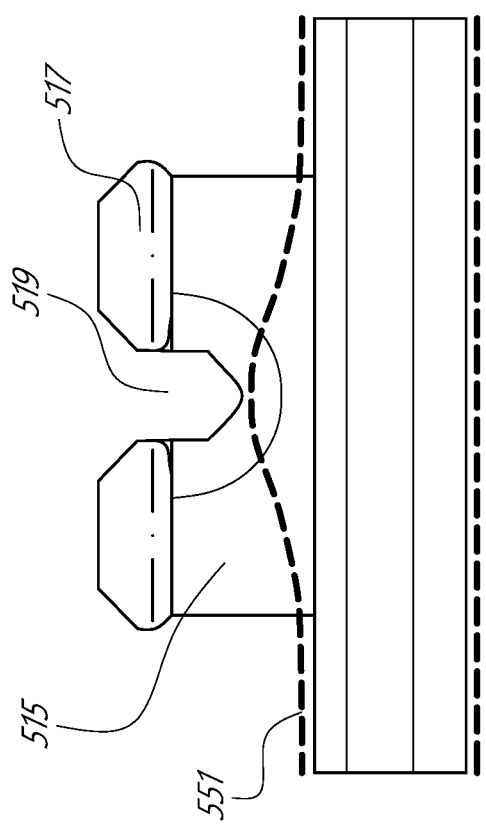
FIG. 36B is a side view of the frame retaining feature of FIG. 36A showing an outline of a casing of the headgear.
Figure 36C:
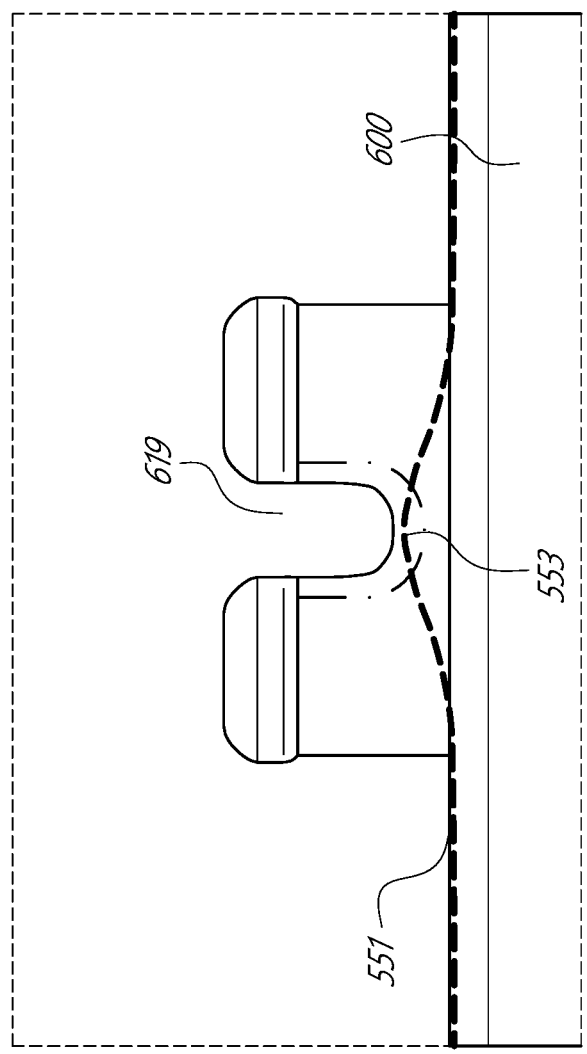
FIG. 36C is a side view of a mold used to create the frame retaining feature of FIG. 36A.

As described herein, the frame 410 can include headgear retaining features 450 in the form of holes that are designed to receive projections 515 of the headgear 404. As shown in FIG. 35A, the projections 515, also referred to as frame retaining features herein, can be located on either side of the yoke 516. In the illustrated embodiment, each of the projections 515 includes two retaining portions 517 separated by a channel 519 as shown in FIGS. 35A and 36A-36B. The channel 519 is formed by a projection 619 in the mold tool 600 that fills the region forming the channel 519 as shown in FIG. 36C. During molding, molten plastic forces itself through the outer casing 551 under pressure or is allowed to exit the outer casing 551 to form the retaining portions 517. The projection 619 of the mold tool 600 also restrains the outer casing 551 fabric or material to prevent or inhibit the outer casing 551 fabric or material from expanding beyond the base of the channel 519 as the plastic exits to form the retaining portions 517, as indicated by 553 in FIG. 36C. The outer casing 551 can also or alternatively be restrained in other ways. For example, if the retaining portions 517 (and/or other projections that protrude from the outer casing 551) have a thin profile or dimension relative to a profile or dimension of the textile outer casing 551, the outer casing 551 may not be able to protrude onto the projection to a large extent. This advantageously prevents or inhibits deformation of the outer casing 551 and/or helps ensure the retaining portions 517 include or are made of only plastic. Having the retaining portions 517 made only or primarily of plastic, rather than including the outer casing, can advantageously improve the function of the frame retaining features 515, e.g., by allowing the frame retaining features 515 to snap into the headgear retaining features 450 more securely. The channel 519 can also or alternatively allow the retaining portions 517 to flex relative to each other to improve performance of the frame retaining features 515, e.g., to allow the frame retaining features 515 to flex to snap into the headgear retaining features 450.

Figure 38A:
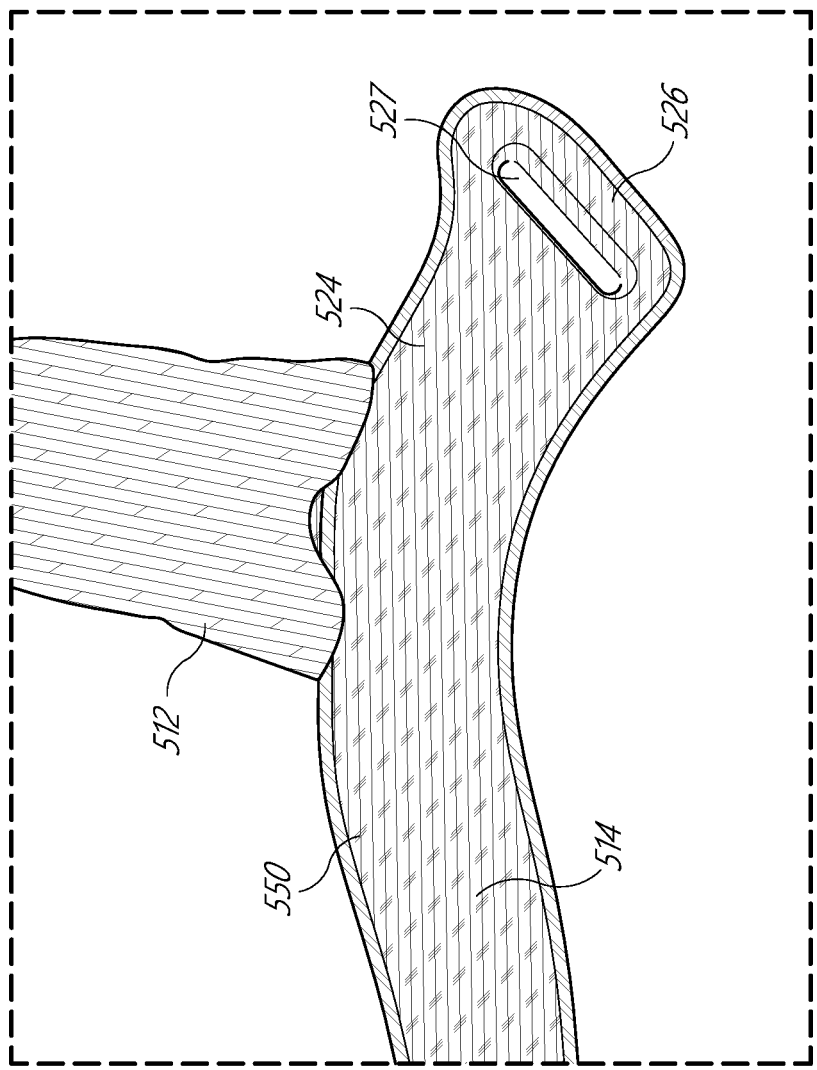
FIG. 38A is a close-up view of a portion of the headgear of the mask of FIG. 33.
Figure 38B:
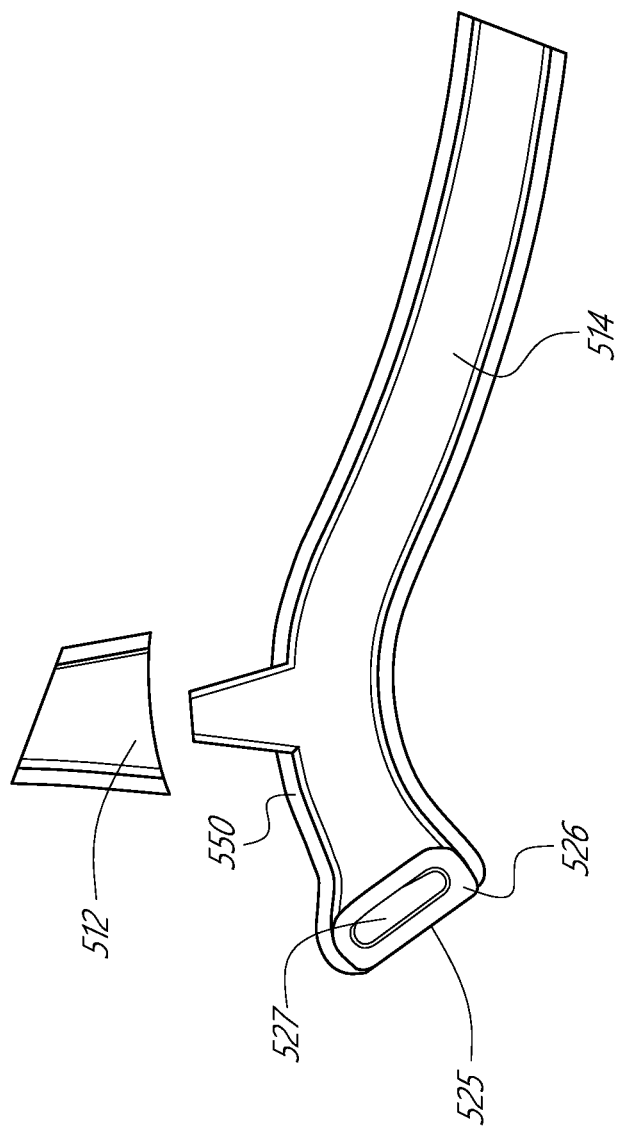
FIG. 38B is a close-up view of a portion of the headgear of the mask of FIG. 33.

As shown in FIG. 38A, each side arm 514 includes a buckle 526. The buckle 526 is formed by an extension of the free end of the side arm 514 and includes an aperture 527 extending through the thickness of the side arm 514. The aperture 527 is configured to receive the rear strap 518. In the illustrated embodiment, the buckle 526 is integrally formed with the side arm 514. In some embodiments, the structure of the buckle 526 can be maintain by the core 549, and the outer casing 551 can make the buckle 526 soft to the touch. The buckle can be formed by intra-molding the entire buckle structure with a complete plastic core, including the location of the aperture 527, and then die cutting the aperture 527. Alternatively, the aperture 527 can be formed in the intra-molding process, where the outer casing 551 of the side arm 514 splits into two tubes at the end of the aperture 527 adjacent the side arm 514, and then the tubes re-combine on the opposite side of the aperture 527. In some embodiments, the buckle 526 can be formed by plastic (or other core 549 material) that bursts through an end of the casing 551, such that the buckle 526 does not include an outer casing 551. In some embodiments, the soft edge 550 of the side arms 514 extends on the top and bottom of the side arms 514 and the buckle 526, and the lateral end 525 of the buckle 526 does not include a soft edge 550, for example as shown in FIG. 38B. In the illustrated embodiment, the buckle 526 is coplanar or in line with the side arm 514 when the headgear 404 is laid flat. In some embodiments, the buckle 526 is offset from the side arm 514, for example, away from or toward the user in use.

Figure 39:
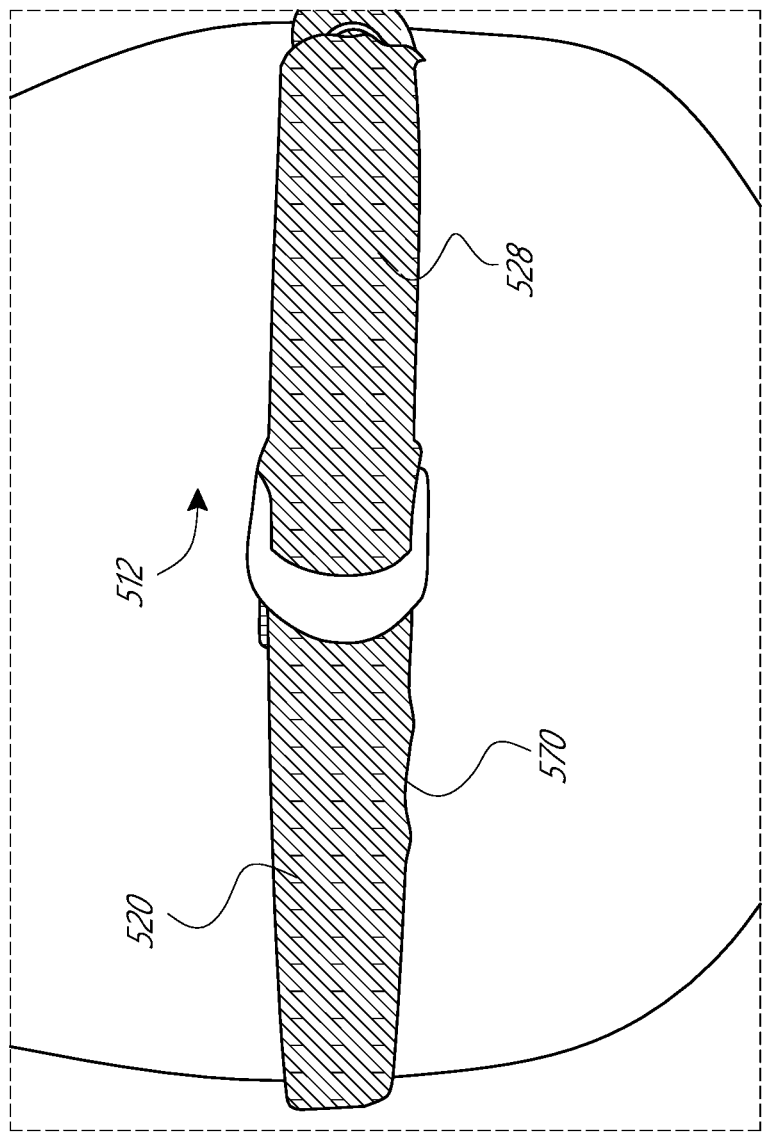
FIG. 39 is a top view of the top strap of the headgear of the mask of FIG. 33.
Figure 40:
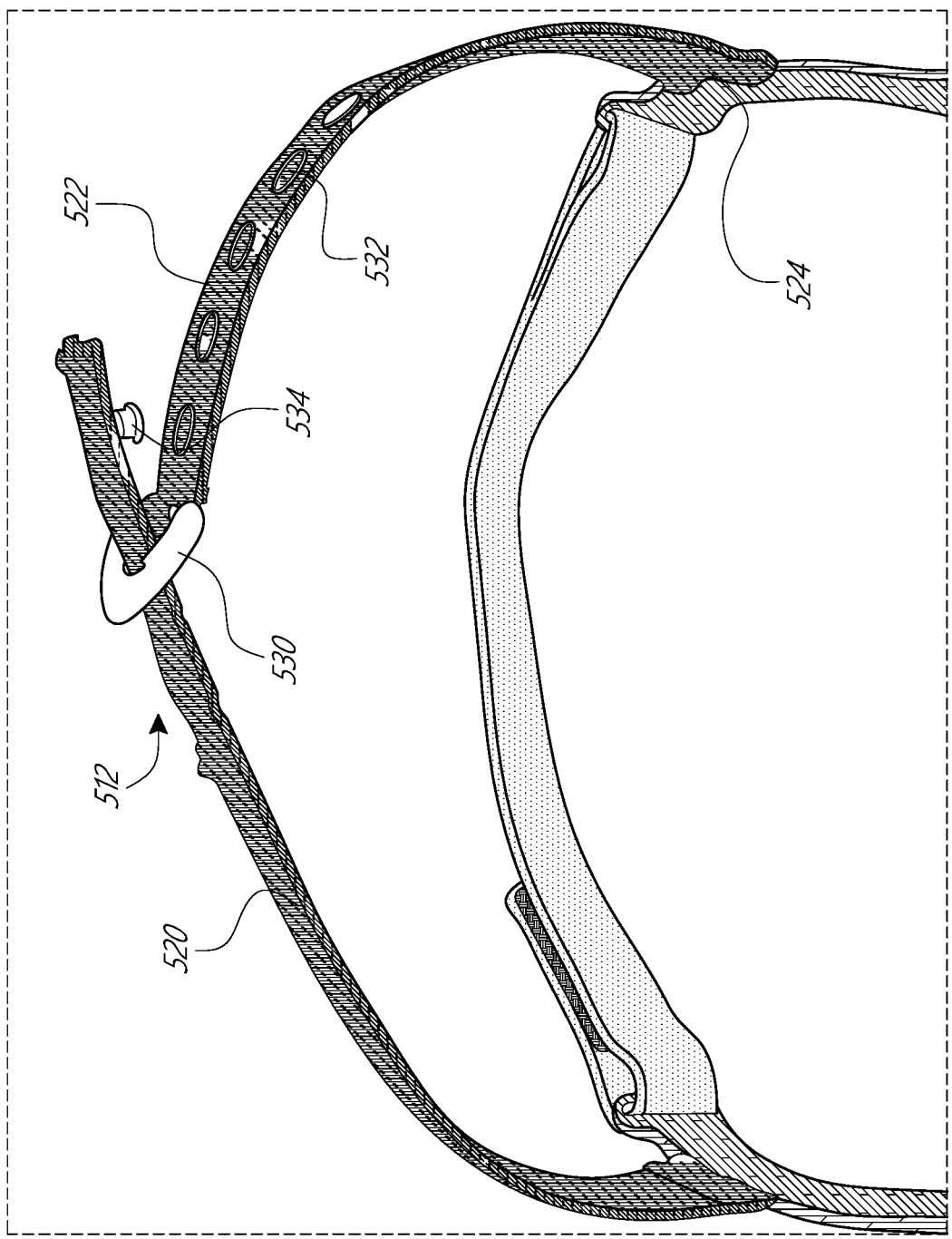
FIG. 40 is a top perspective view of the top strap of the headgear of the mask of FIG. 33 in a disengaged position or configuration.

Similar to headgear 204, the top strap 512 of the headgear 404 includes a first (or left) portion 520 and a second (or right) portion 522 as shown in FIGS. 39-40. The first 520 and second 522 portions are separate from each other. Each of the first 520 and second 522 portions has a free end and a fixed end. The fixed ends extend at an angle from the side arms 514 at the junctions 524. The free ends are configured to be adjustably connected by an adjustment mechanism 528. The adjustment mechanism 528 allows the top strap 512 to be adjusted and secured at a desired length.

Figure 41:
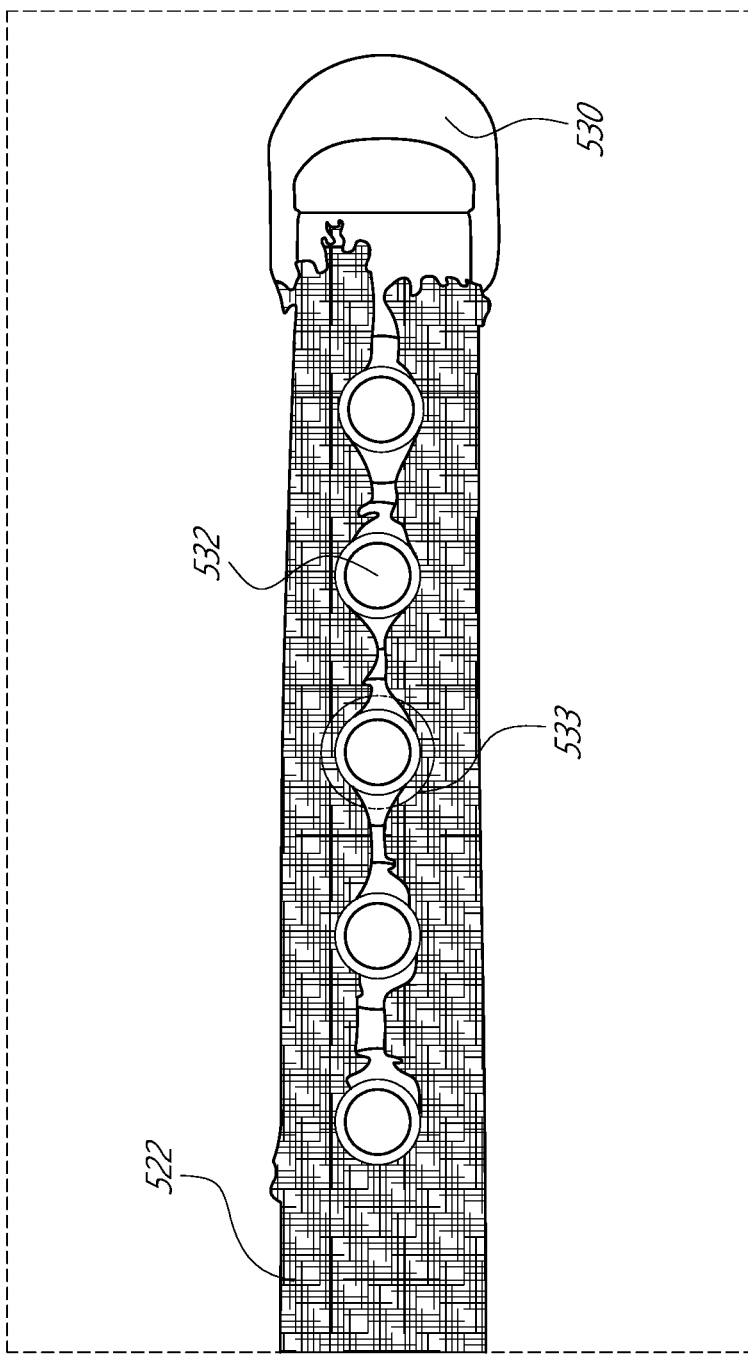
FIG. 41 is a close-up view of a portion of a second portion of the top strap of FIG. 40.

As shown in FIGS. 39-41, the free end of the second portion 522 includes a guide loop 530, and the second portion 522 includes a plurality of holes 532 spaced along a length of the second portion 522 proximate the free end. In the illustrated embodiment, the guide loop 530 is plastic. The guide loop 530 can be formed by a burst-through molding process. "Burst-through molding" is described in the Applicant's Applications U.S. 62/309,400, U.S. 62/323,459, U.S. 62/364,767, and U.S. 62/401,462. Burst-through molding is a variation of intra-molding as described above. The burst-through molding process comprises introducing molten plastic into a textile casing and pushing the molten plastic through a portion of the textile casing. A component formed by the burst-through molding process comprises a unitary plastic core that is integrally formed with a textile casing and the unitary plastic core has a portion that extends through the textile casing. In some embodiments, the guide loop 530 can be coupled to the free end of the second portion 522. In some embodiments, the guide loop 530 includes an outer casing, such as an extension of the outer casing 551. In some embodiments, the guide loop 530 is made of or includes only the outer casing material and no plastic (or other core material). The first portion 520 includes a projection 534 that protrudes from an internal surface of the first portion 520 (i.e., a surface of the first portion 520 that faces the second portion 522 in use) proximate the free end. The first portion 520 can also include a number of position indicators. To adjust and/or secure the first 520 and second 522 portions relative to each other, the free end of the first portion 520 is passed through the guide loop 530, and the projection 534 is passed through and/or secured in one of the holes 532, for example, via a snap-fit connection.

The holes 532 can be formed using a burst-through intra-molding process. In some embodiments, the outer casing 551 of the second portion 522 can split into two parallel (and enclosed) casing portions adjacent (on the junction 524 side of) the first hole 532 (i.e., the hole 532 closest to the junction 524), and the parallel casing portions can extend along the length of the second portion 522 including the holes 532. The parallel casing portions can recombine into a single casing after (or on the free end side of) the last hole 532 (i.e., the hole 532 farthest away from the junction 524). The parallel casing portions can bend towards each other between holes 532 such that a gap in the fabric or material of the casing 551 may not be easily observed by the user. In some embodiments, the parallel casing portions do not recombine after the last hole 532. In some such embodiments, pressure from the plastic or core 549 material can force the parallel casing portions to move closer together after the final hole 532 such that a gap in the fabric is not easily observed. In some embodiments, the outer casing 551 includes the holes 532, and the mold tool is designed to restrict the flow of molten plastic (or other core 549 material) from extending into the holes 532 during molding. In some embodiments, the second portion 522 can be intra-molded without holes 532, and the holes 532 can be created via post-processing, for example, via die cutting. In some embodiments, the outer casing 551 can terminate proximate or adjacent (on the junction 524 side of) the first hole 532, and the remainder of the second portion 522 can be formed using the burst-through process to include only plastic (or other core 549 material).

In some embodiments, each hole 532 is at least partially surrounded (on one or both of an internal and external surface of the second portion 522) by a surrounding channel 533. The surrounding channel 533 can assist with forming the hole 532 via intra-molding. The mold tool can include a projection that applies pressure on the outer casing 551 during molding to form the channel 533. The mold tool projection can restrict movement of the outer casing 551 during molding. Restricting movement of the outer casing 551 advantageously helps ensure that a periphery of the hole 532 (in other words, the plastic, or other core 549 material, structure inside the boundary of the surrounding channel 533) is entirely or substantially entirely plastic (or other core 549 material). An entirely plastic (or other core 549 material) hole 532 periphery can improve the function of the adjustment mechanism 528 and/or help maintain tolerances associated with the holes 532.

Figure 42:
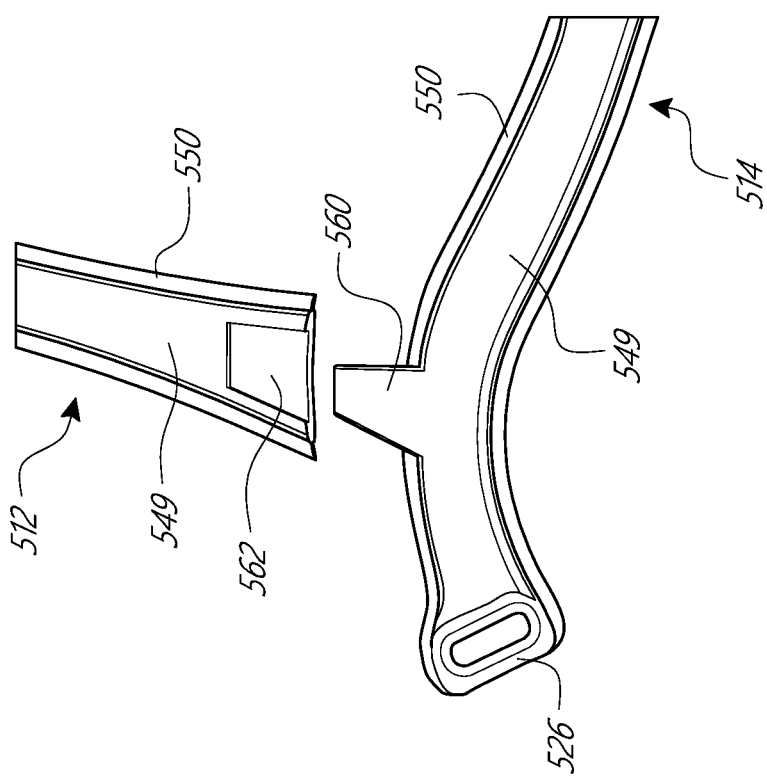
FIG. 42 is a close-up view of a portion of the headgear of the mask of FIG. 33 showing an embodiment of a connection between the side arm and the top strap of the headgear.

In some embodiments, each of the first 520 and second 522 portions of the top strap 512 is integrally formed with the adjacent side arm 514, for example, via the burst-through intra-molding process. In some embodiments, each of the first 520 and second 522 portions is an independent component that is coupled or connected, permanently or removably, to the respective side arm 514. For example, as shown in FIG. 42, the junction 524 of each side arm 514 includes a junction projection 560. The junction projections 560 can be formed during molding of the side arms 514, for example, using the burst-through intra-molding process. Each of the first 520 and second 522 portions of the top strap 512 includes a recessed surface 562 at or proximate the junction end. The recessed surfaces 562 have a profile that is inverse (or approximately inverse) of or corresponds to a profile of the junction projections 560. After molding, each of the junction projections 560 is inserted into the outer casing 551 of the junction end of the respective first 520 or second 522 portion of the top strap 512 and positioned within the recessed surface 562. Each side arm 514 and the respective one of the first 520 and second 522 portions can then be welded together, for example, using ultrasonic welding, RF welding, or other suitable means. After welding, the side arms 514 and top strap 512 form a single plastic (or other core material) component. The outer casing 551 of the top strap 512 can be welded to the outer casing 551 of the side arm 514. In some embodiments, an area of the top strap 512 adjacent to the junction 524 does not include a soft edge 550. In such an embodiment, welding the core 549 of the side arm 514 and top strap 512 sufficiently secures the outer casings 551 together without needing to weld the outer casings 551 of the side arm 514 and top strap 512. In some embodiments, the junction projections 560 are approximately the same thickness as a remainder of the core 549 of the side arms 514. In some embodiments, the junction projections 560 have a reduced thickness. In some embodiments, the junction projections 560 are offset from a central plane of the side arms 514. A reduced thickness and offset junction projection 560 can allow the core 549 of the side arm 514 and top strap 512 to be flush at the boundary between the junction projection 560 and recessed surface 562 when the junction projection 560 is seated in the recessed surface 562.

Figure 43A:
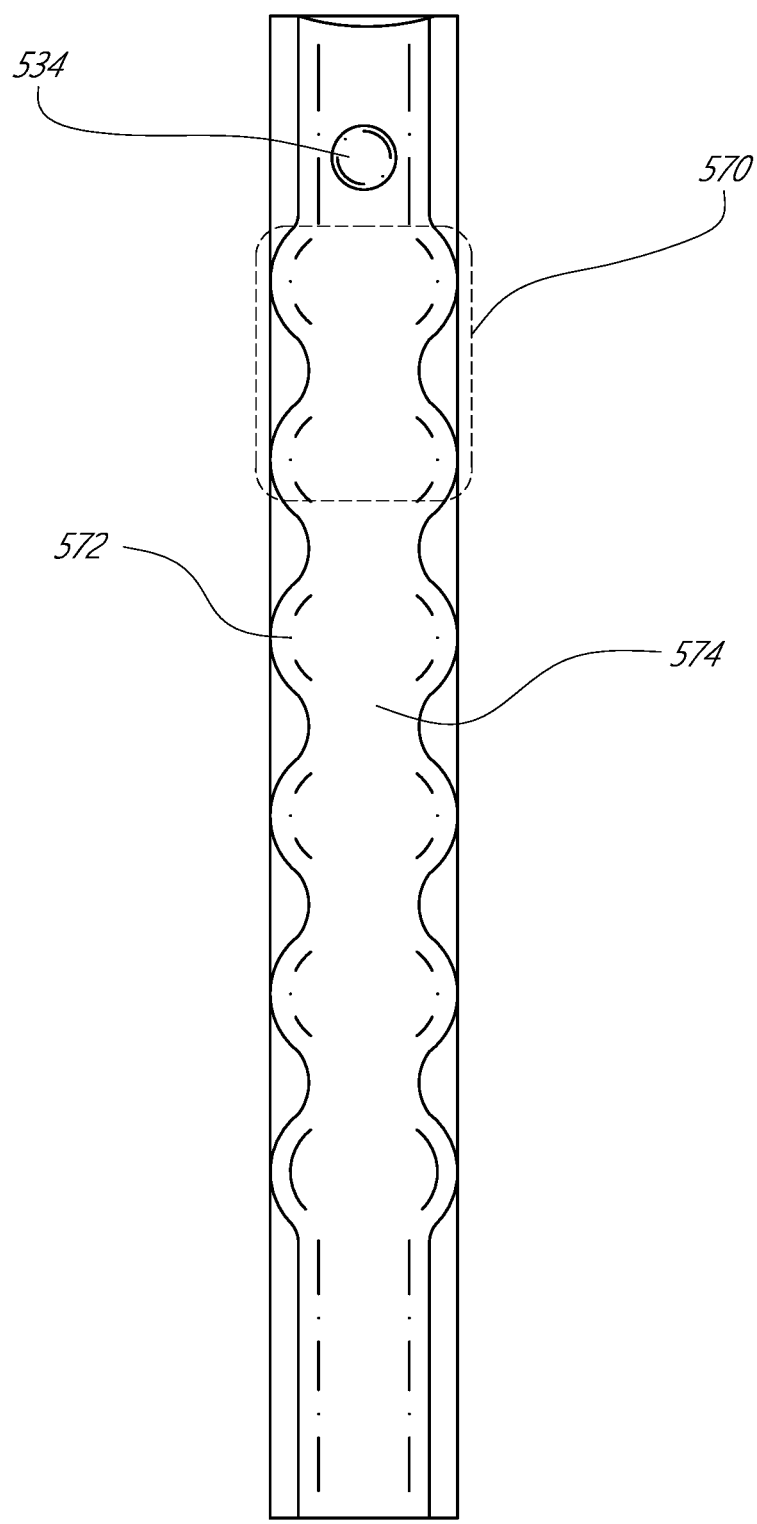
FIG. 43A is a bottom view of an example embodiment of a location guide of a first portion of the top strap of the headgear.
Figure 43B:
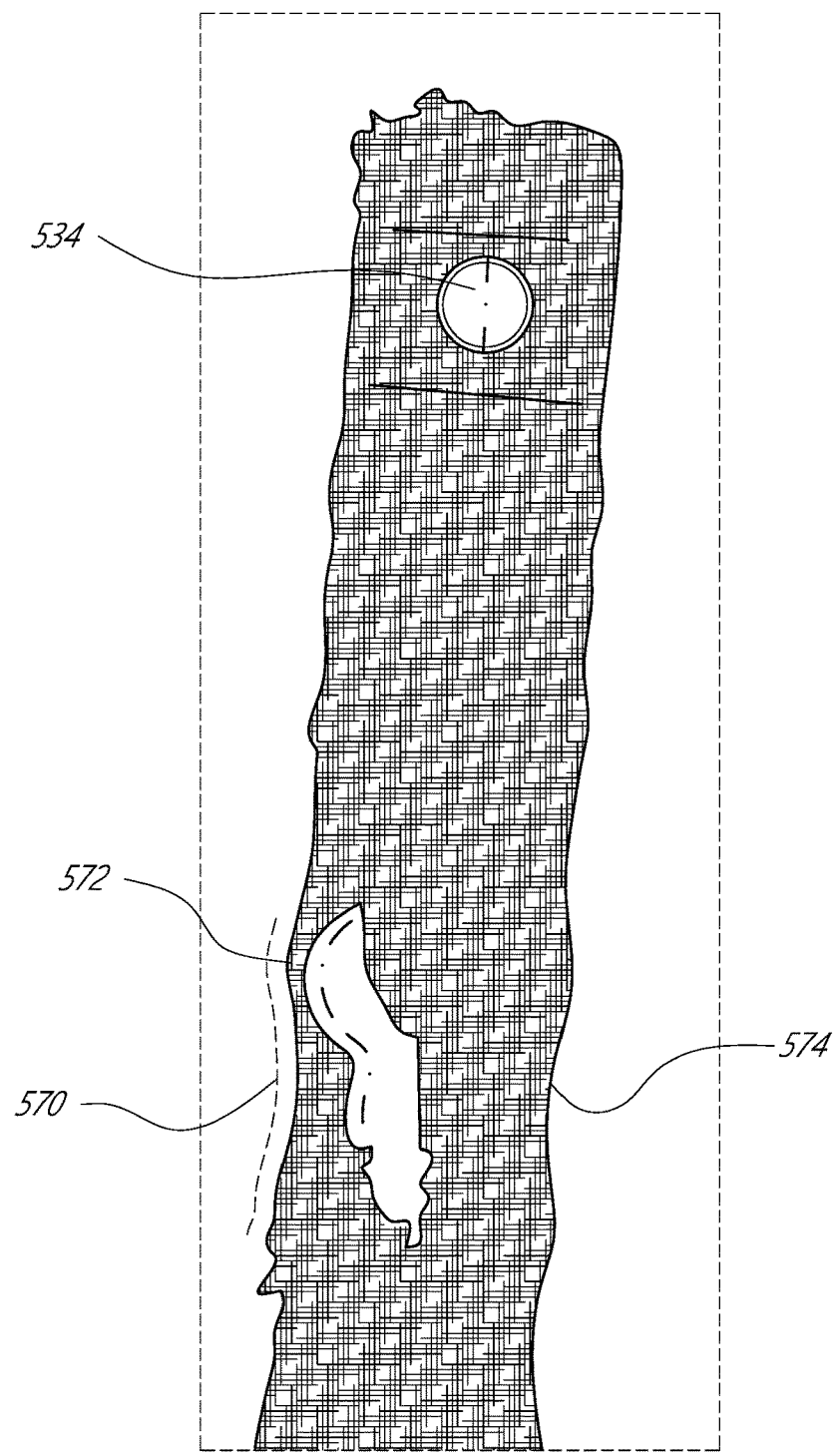
FIG. 43B is a bottom view of an example embodiment of a location guide of a first portion of the top strap of the headgear.
Figure 43C:
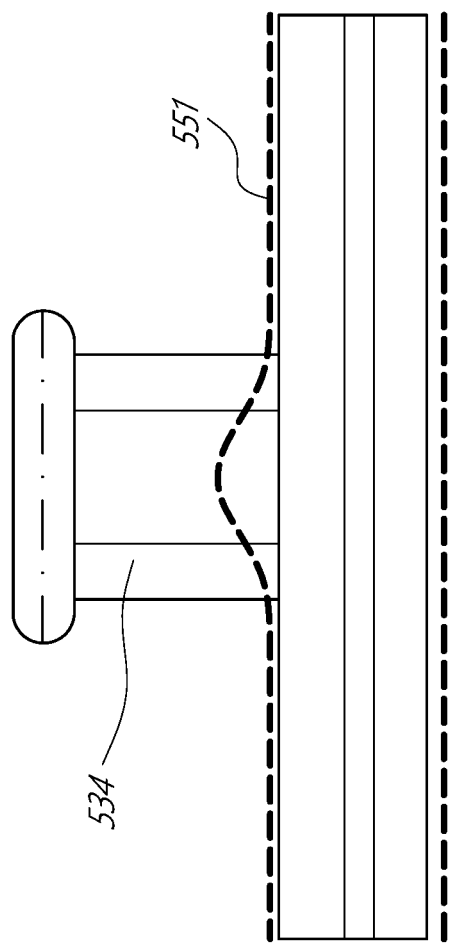
FIG. 43C is a side view of a portion of the first portion of the top strap.

In some embodiments, the first portion 520 of the top strap 512 includes location guides 570 to assist the user in setting and retaining a particular headgear setting, length, or size. As shown in FIGS. 43A-43B, the location guides 570 can include a series of protruding edges 572. A central portion 574 of the first portion 520 has a reduced lateral profile compared to the protruding edges 572. The protruding edges 572 have a slightly greater profile or width than a diameter or width of the guide loop 530. Therefore, as the first portion 520 of the top strap 512 is slid through the guide loop 530 of the second portion 522, the contact and interaction between the protruding edges 572 and the guide loop 530 provides a friction force or resistive force. The resistive force can prevent or reduce the likelihood of passive movement of the first portion 520 through the guide loop 530. The user can therefore disengage the projection 534 from the holes 532, and the resistive force can help resist relative movement between the first 520 and second 522 portions to maintain the length of the strap 512 unless and until the user applies sufficient force to overcome the resistive force. In the illustrated embodiment, the protruding edges 572 are curved or domed outwardly convex. Other shapes or configurations for the protruding edges 572 are also possible. For example, the protruding edges 572 can be triangular.

Figure 44:
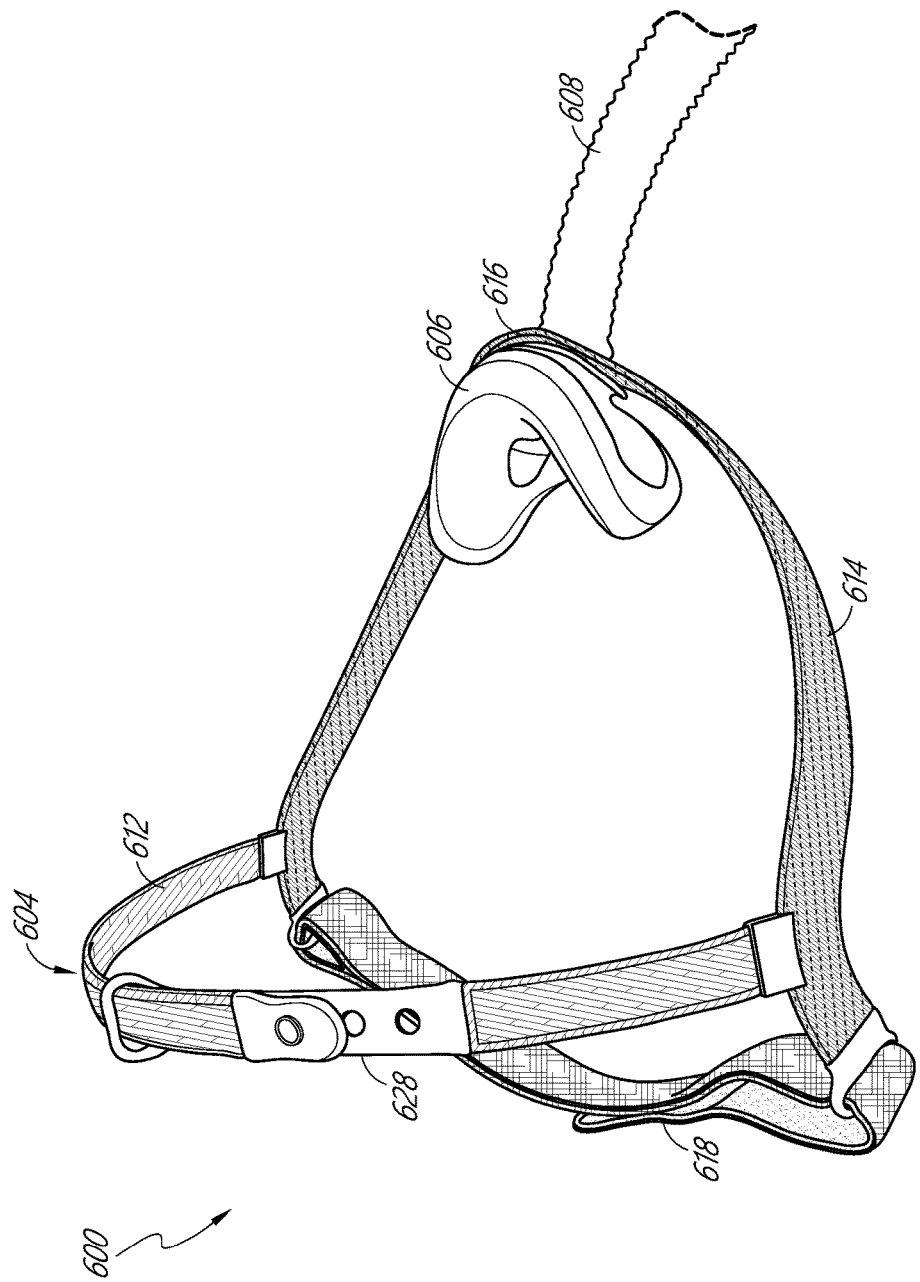
FIG. 44 is a top perspective view of a non-limiting exemplary embodiment of a respiratory mask assembly according to the present disclosure.
Figure 45:
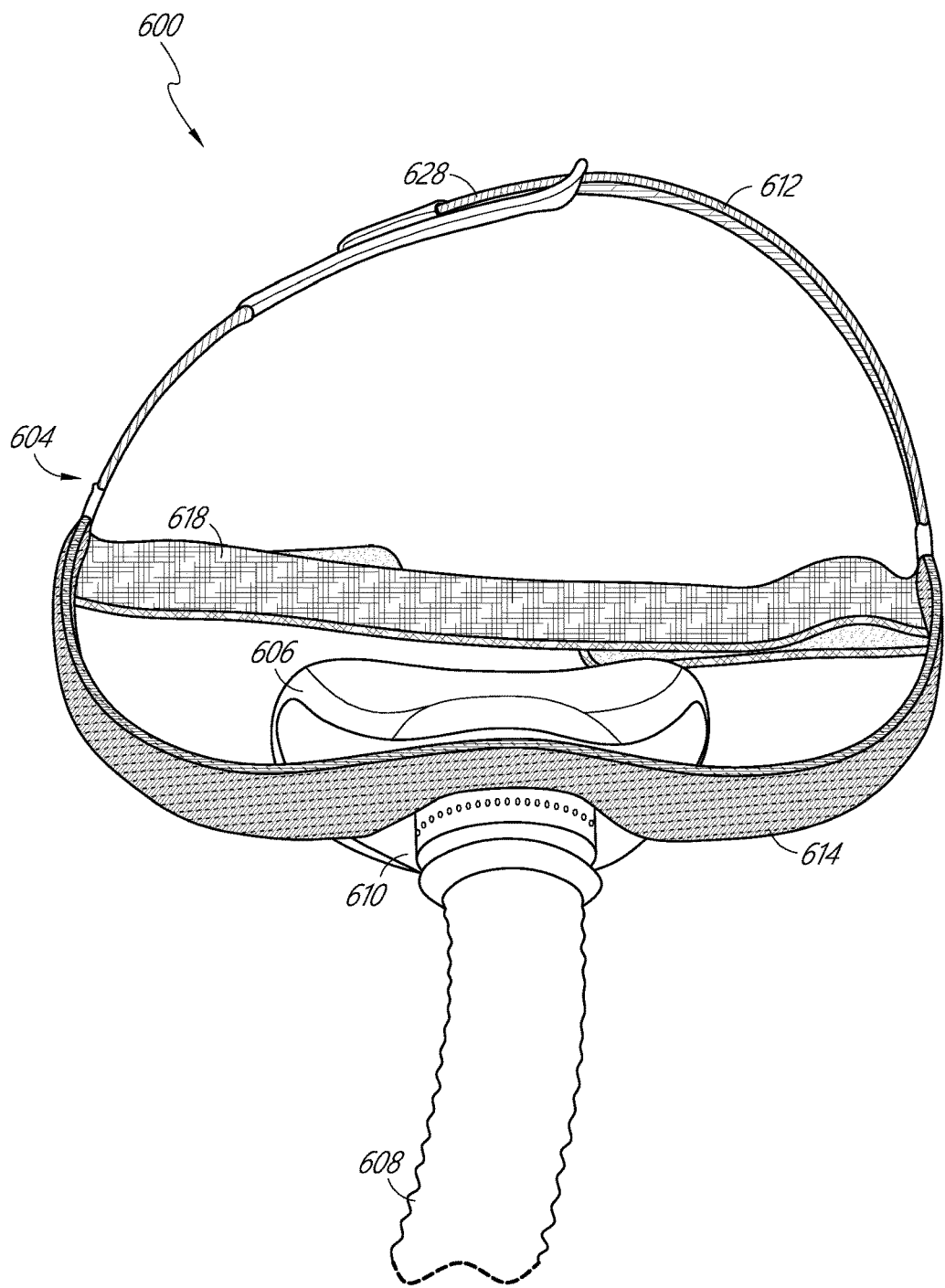
FIG. 45 is a front view of the respiratory mask assembly of FIG. 44.
Figure 46:
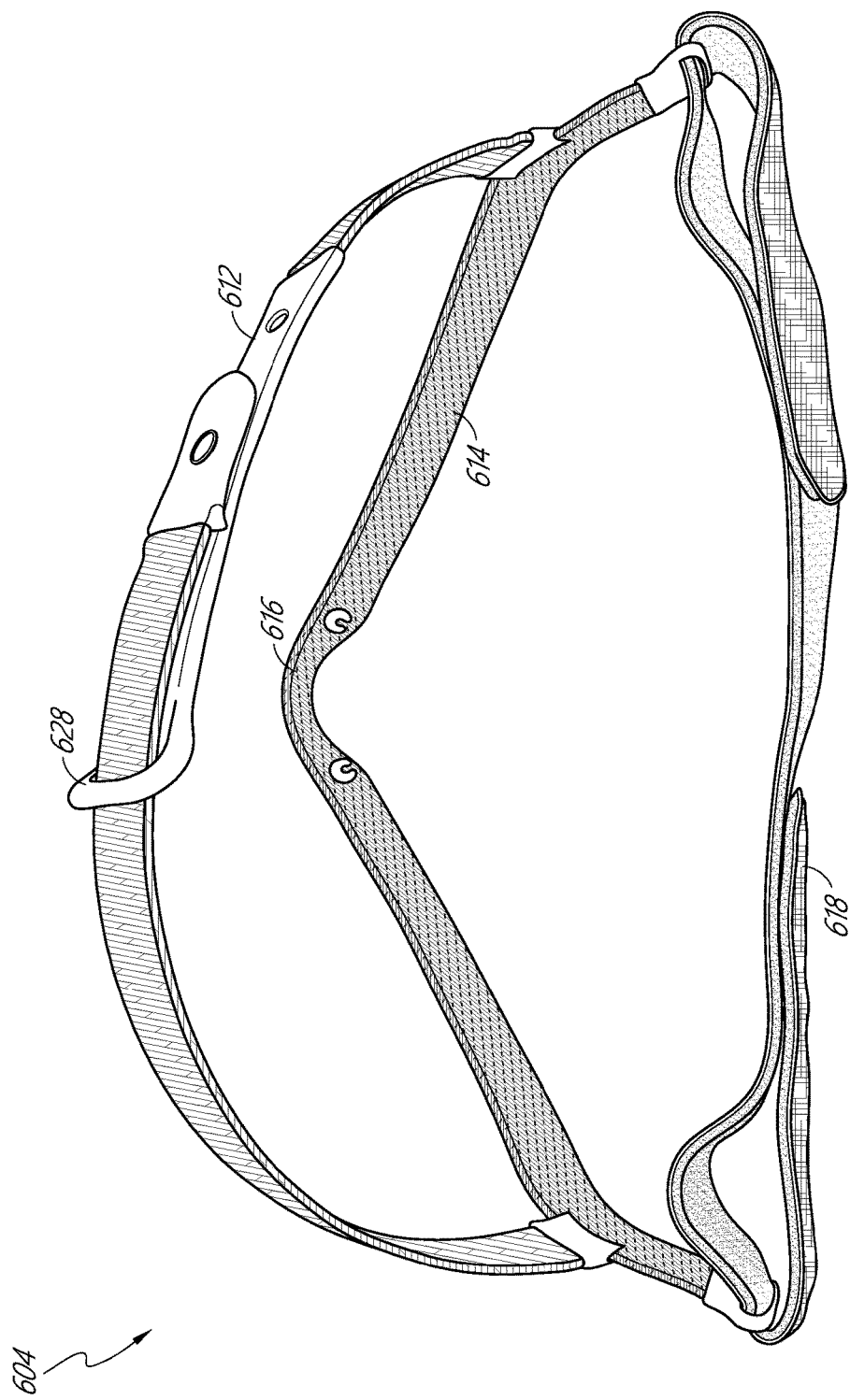
FIG. 46 is a rear view of a headgear of the respiratory mask assembly of FIG. 44.
Figure 48B:
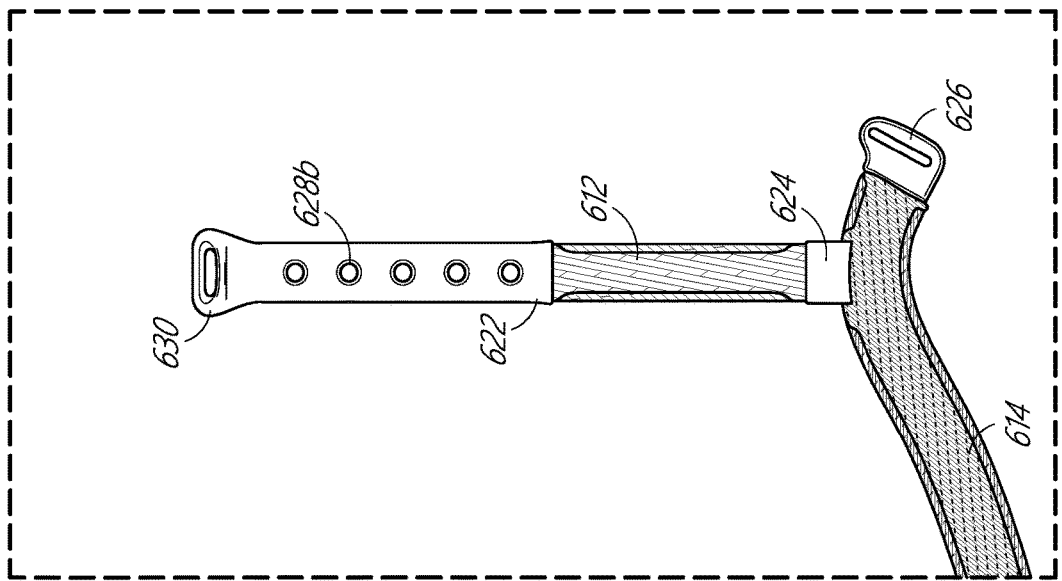
FIG. 48B is a rear or internal view of FIG. 48A.
Figure 48A:
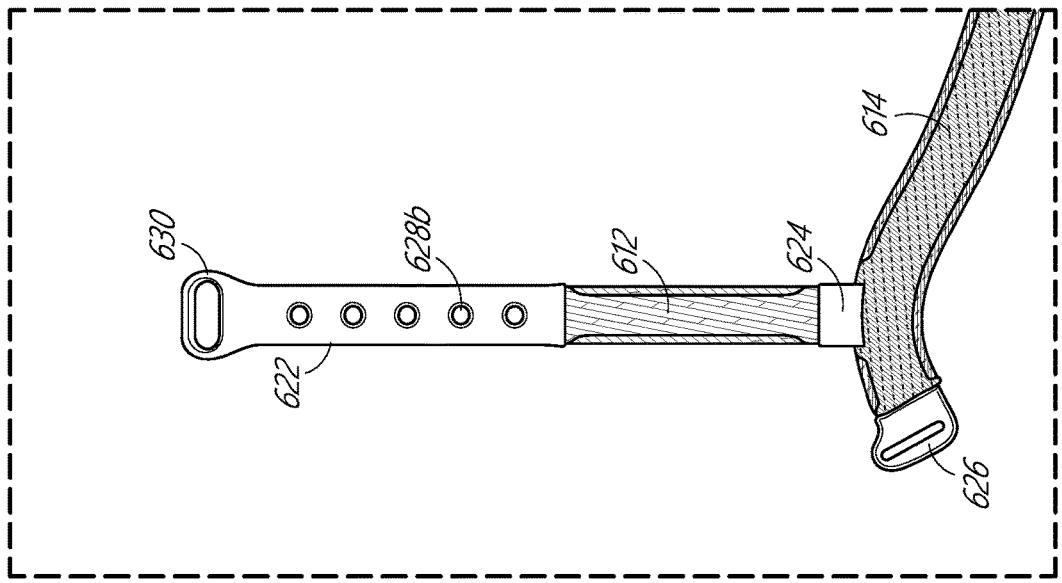
FIG. 48A is a front or external view of the right side of the headgear of FIG. 47A.

FIGS. 44-45 show another non-limiting exemplary embodiment of a respiratory mask assembly 600. The respiratory mask assembly 600 includes a patient interface and a headgear 604. The patient interface includes a seal 606 configured to connect to a frame 610 and a gas delivery conduit 608. The frame 610 is similar to and/or include some or all of the features of frame 410. The headgear 604 and frame 610 are configured to secure the seal 606 in a stable position below the nose of a user in use. FIGS. 46-47 show an exemplary embodiment of the headgear 604 that is used with frame 610. In the illustrated embodiment, the headgear 604 has a bifurcated configuration. The headgear 604 is similar to the headgear 404 in some ways, e.g., the headgear 604 has the same or a similar overall shape as the headgear 404 and includes a top strap 612, a pair of opposing side arms (or bottom or front strap) 614, a yoke 616, and a rear strap 618. The top strap 612 and rear strap 618 form the bifurcated configuration. In some embodiments, one or more of the top strap 612, bottom strap 614 and yoke 616, and/or rear strap 618 are a different color than one or more of the other straps.

The side arms 614 and/or top strap 612 include a core and an outer casing, for example, similar to the headgear 504. In some embodiments, the core is made of or includes a plastic material. In some embodiments, the outer casing is or includes a textile.

The top strap 612 of the headgear 604 includes a first (or left) portion 620 and a second (or right) portion 622 as shown in FIGS. 47A-49B. The first 620 and second 622 portions are separate from each other. Each of the first 620 and second 622 portions has a free end and a fixed end. The fixed ends extend from, e.g., at an angle from, the front strap 614. In the illustrated embodiment, the front strap 614, first portion 620 of the top strap 612, and second portion 622 of the top strap 612 can be formed independently from each other via intra-molding and then joined together via over-molded joints. As shown, each of the first 620 and second 622 portions is coupled to the front strap 614 via an over-molded joint 624.

The free ends of the first 620 and second 622 portions of the top strap 612 are configured to be adjustably connected by an adjustment mechanism 628. The adjustment mechanism 628 allows the top strap 612 to be adjusted and secured at a desired length. The adjustment mechanism 628 includes inter-engaging portions provided on respective first and second top strap portions 620, 622. The inter-engaging portions are selectively engaged in one of a plurality of discrete configurations to set the length of the top strap 612. When the inter-engaging portions are engaged, the first and second top strap portions 620, 622 are in a partial overlapping configuration. In this overlapping configuration, a portion of an internal surface of the first portion 620 of the top strap overlays a portion of an external surface of the second portion 622 of the top strap 612. The internal surface of the top strap first portion 620, in use, faces towards the user and the external surface of the top strap second portion 622, in use, faces away from the user. The inter-engaging portions can be disengaged and re-engaged in a different configuration to facilitate adjustment of the length of the top strap. For the different lengths of the top strap 612 the first and second portions 620, 622 overlap in differing lengths or to differing extents. In the illustrated embodiment, the inter-engaging portion of the first portion 620 includes a male connector 628a and the inter-engaging portion of the second portion 622 includes a female connector 628b; although in some embodiments, the inter-engaging portion of the first portion 620 includes a female connector and the inter-engaging portion of the second portion 622 includes a male connector.

Figure 49B:
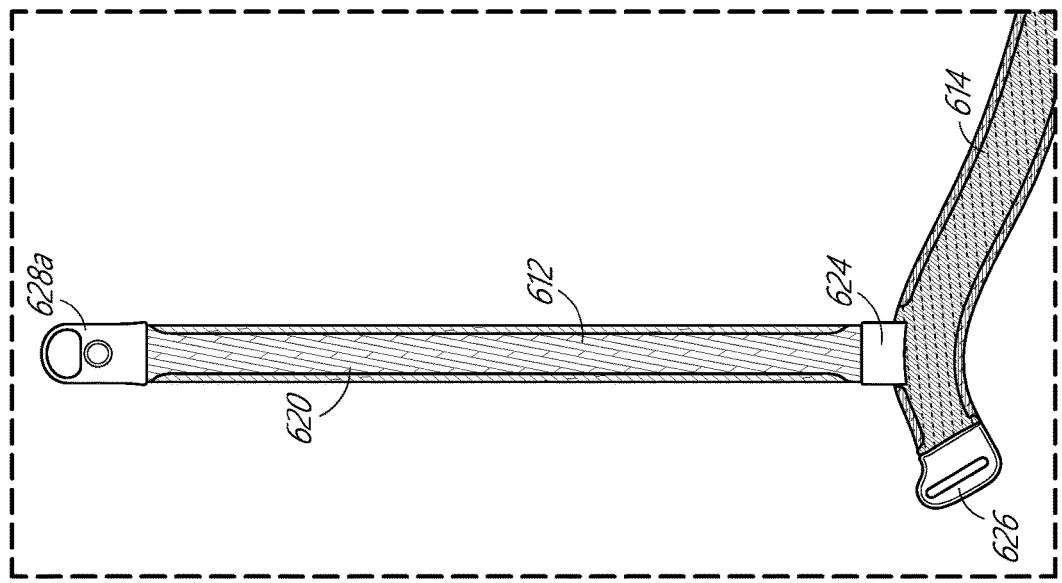
FIG. 49B is a rear or internal view of FIG. 49A.
Figure 49A:
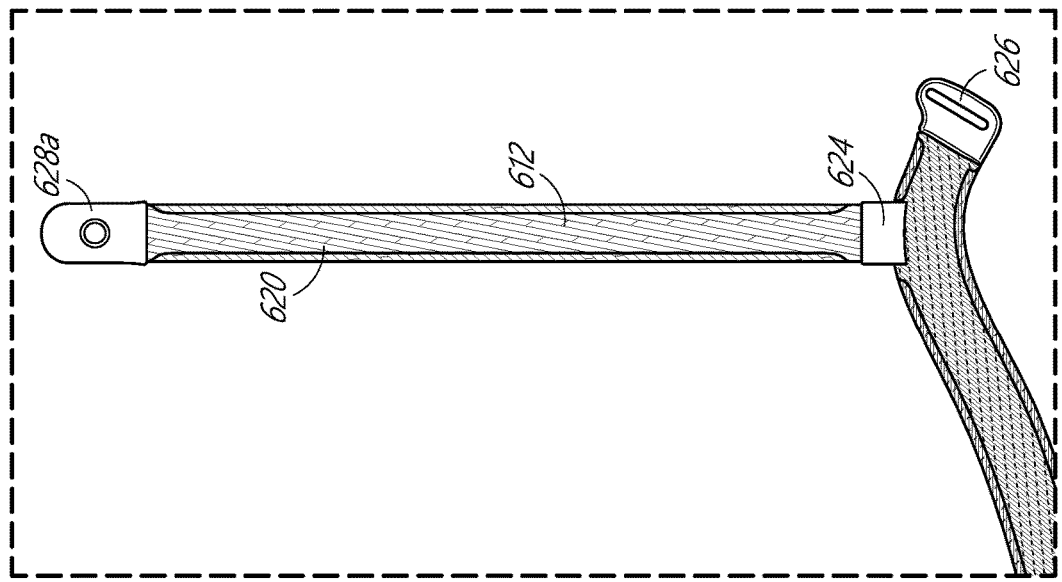
FIG. 49A is a front or external view of the left side of the headgear of FIG. 47A.

As shown in FIGS. 47A-48B, the free end of the second portion 622 includes a guide loop 630. The inter-engaging portion of the second portion 622 includes a plurality of recesses in the form of holes 632 spaced along a length of the second portion 622 proximate the free end. As illustrated, each of the holes 632 extends through the second portion 622 of the top strap 612. In other embodiments, the inter-engaging portion of the second portion 622 includes recesses extending into the top strap second portion through its external surface. As shown in FIGS. 47A, 49B, and 50B the inter-engaging portion of the top strap first portion 620 includes a projection 634 that protrudes from the internal surface of the first portion 620 proximate the free end. To adjust and/or secure the first 620 and second 622 portions relative to each other, the free end of the first portion 620 is passed through the guide loop 630, and the projection 634 is inserted into and/or secured in one of the holes 632, for example, via a snap-fit connection.

In the illustrated embodiment, the inter-engaging portions of the adjustment mechanism 628 (i.e., the male connector 628a and female connector 628b) are not covered by the outer casing. This can advantageously provide a neater finish (e.g., hiding loose thread ends) and/or ease of manufacturing.

Figure 51B:
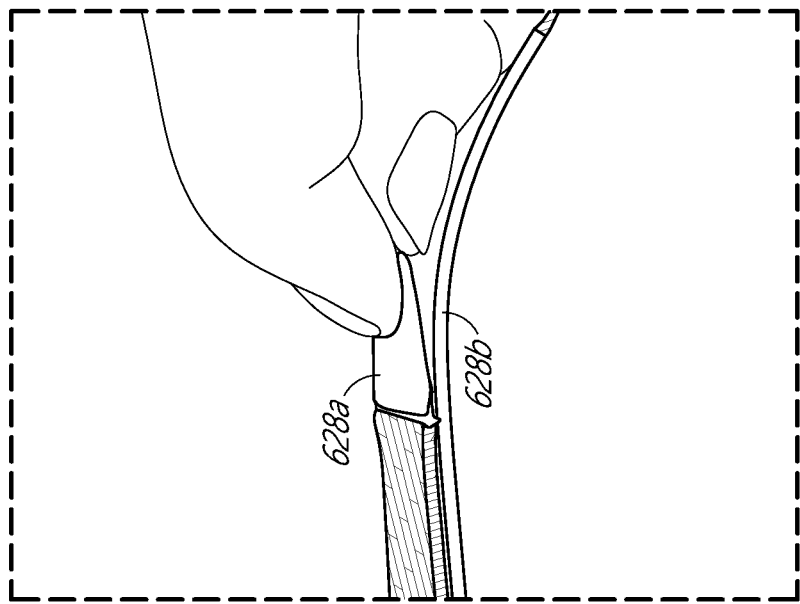
FIGS. 51A and 51B show different methods of connecting and/or disconnecting the male connector of FIG. 50A and a female connector of the headgear of FIGS. 46 and 47A.
Figure 51A:
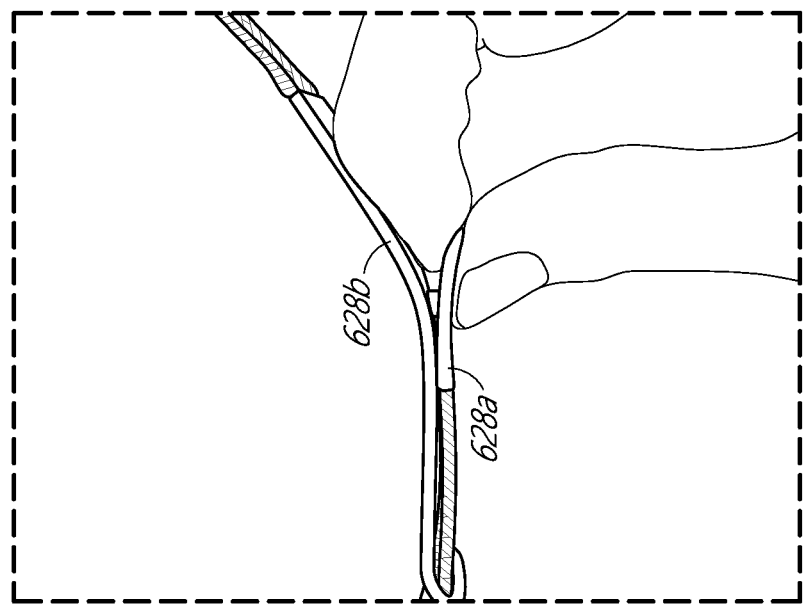

As shown in FIGS. 50A-50C, the first portion 620 of the top strap is provided with or includes a thumb grip 629 on and/or in the external surface of the first portion (e.g., on and/or in the external surface of the male connector 628a) (i.e., a surface that faces away from the top strap second portion and the user 622 in use). The thumb grip 629 is provided on the opposite side of the top strap first portion 620 to or from the projection 634. The thumb grip 629 can include a recessed portion (e.g., as shown in FIG. 50C) and/or a raised rib (e.g., a raised ring as shown in FIG. 50A). The first portion 620 is provided with or includes a finger grip 631 on and/or in the internal surface of the top strap first portion 620 (e.g., on and/or in the internal surface of the male connector 628a). In the illustrated embodiment, the finger grip 631 includes an indent or recessed portion. The finger grip 631 is located on the top strap first portion 620 beyond or distal to (i.e., toward the free end) the projection 634. The finger grip 631 is provided on the same side of the top strap first portion 620 to or as the thumb grip 629. The finger grip 631 is thus on the opposite side of the top strap first portion 620 to or form the thumb grip 629. The thumb 629 and/or finger 631 grips advantageously allow a user to grip the male connector 628a more easily. The thumb 629 and/or finger 631 grips also or alternatively provide visual and/or tactile cues to the user as to how to grip and use the adjustment mechanism 628, which improves ease of use. The indent or recessed portion of the finger grip 631 thins or reduces the thickness of that portion of the top strap first portion 620. This thinning can make the inter-engaging portion of the top strap first portion 620 more flexible, which advantageously allows the user to disengage the inter-engaging portion. For example, the user is able to more easily flex and/or lift the male connector 628a away from the female connector 628b. In use, the thumb grip 629 can be gripped by the user's thumb or finger and/or the finger grip 631 can be gripped by the user's thumb or finger, depending on what is comfortable for the user. FIG. 51A illustrates a user gripping the finger grip 631 with a finger and the thumb grip 629 with a thumb, whereas FIG. 51B illustrates a user gripping the finger grip 631 with a thumb and the thumb grip 629 with a finger. In this respect, the thumb and finger grips 629, 631 are first and second grips that can be engaged interchangeably by a user's thumb and finger to clamp the free end of the top strap first portion therebetween.

Figure 53A:
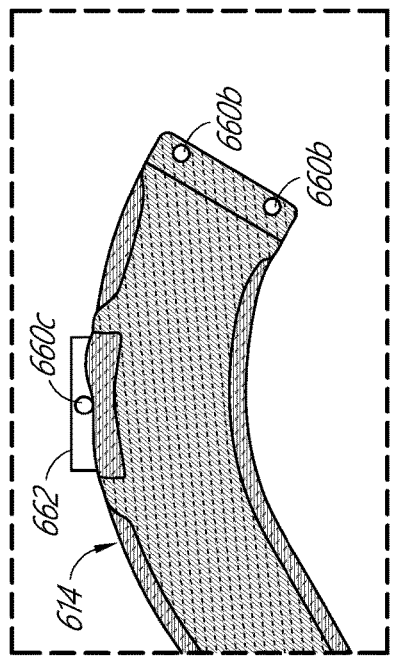
FIG. 53A is a partial external view of a bottom strap of the headgear of FIG. 46.
Figure 53B:
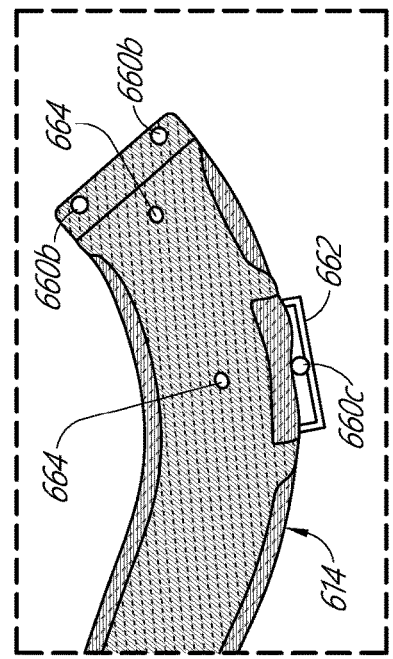
FIG. 53B is a partial internal view of the bottom strap of FIG. 53A.
Figure 52A:
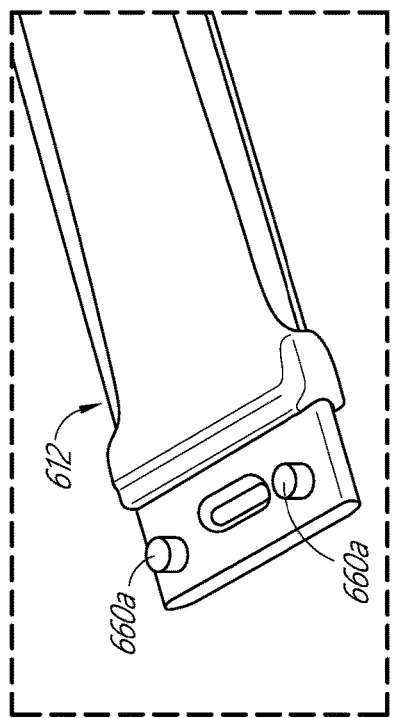
FIG. 52A is a partial perspective external view of a top strap of the headgear of FIG. 46.
Figure 52B:
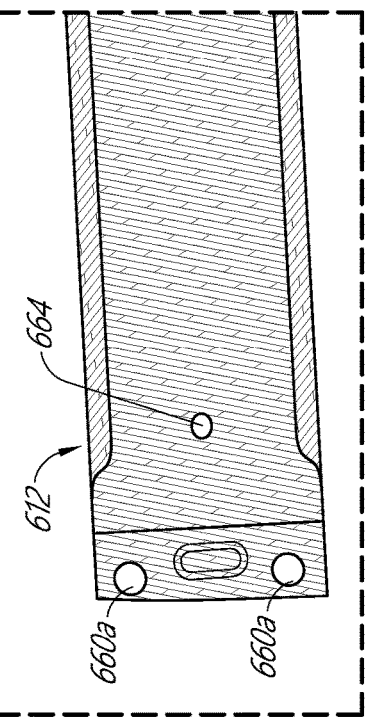
FIG. 52B is a partial internal view of the top strap of FIG. 52A.
Figure 54A:
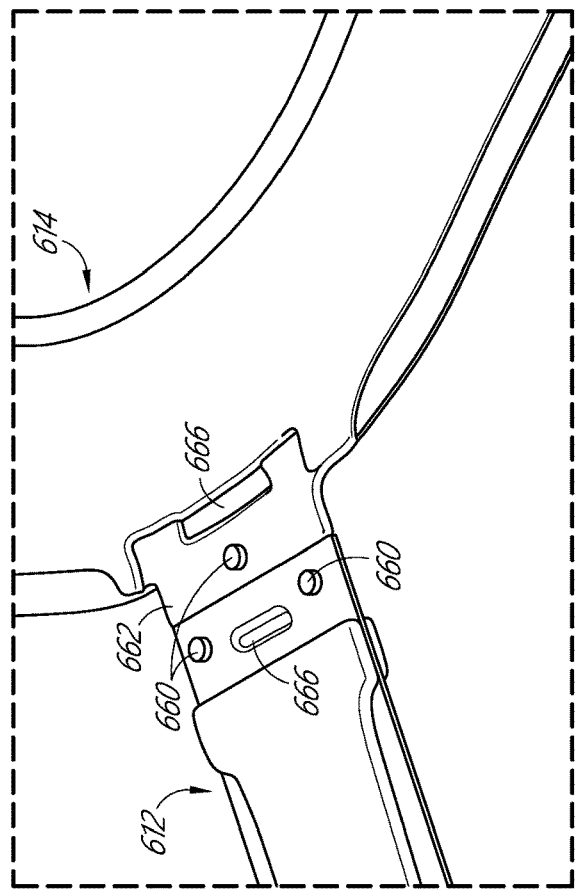
FIG. 54A is a partial external view of a joint between the top strap of FIG. 52A and the bottom strap of FIG. 53A.
Figure 54B:
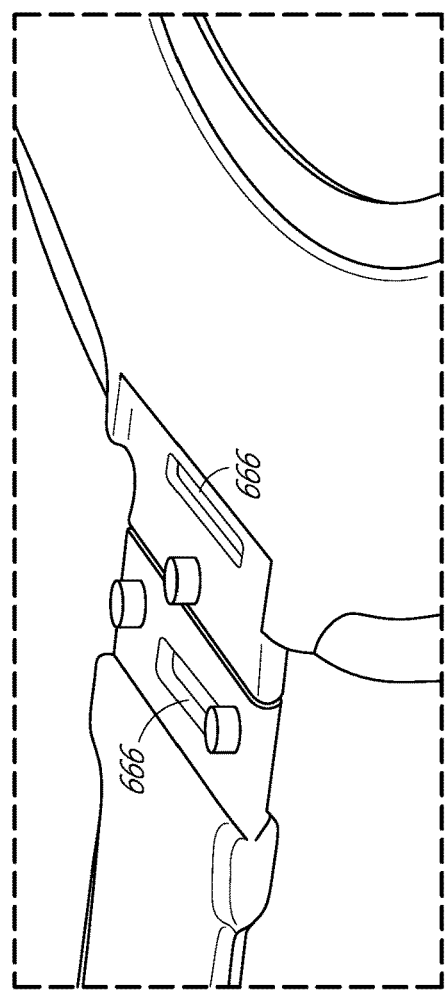
FIG. 54B is a perspective view of the joint of FIG. 54A.
Figure 55B:
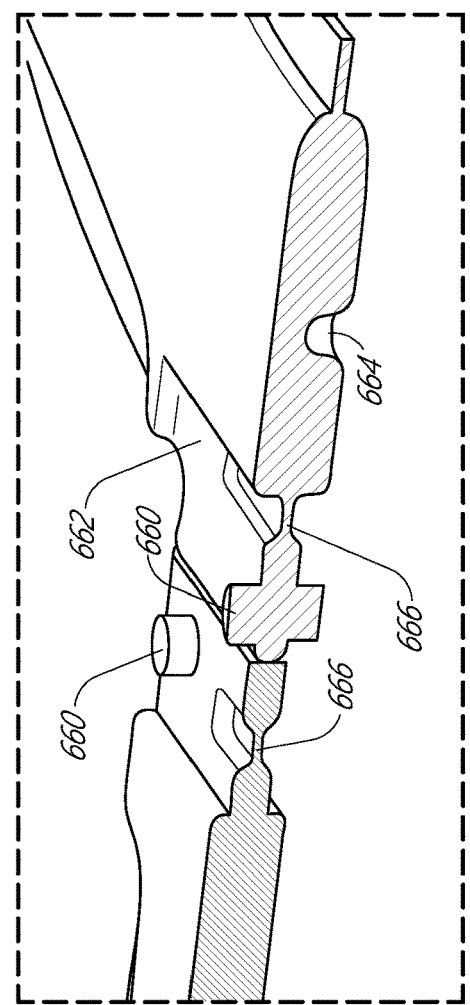
FIG. 55B is a section view of the joint of FIG. 54A.
Figure 55A:
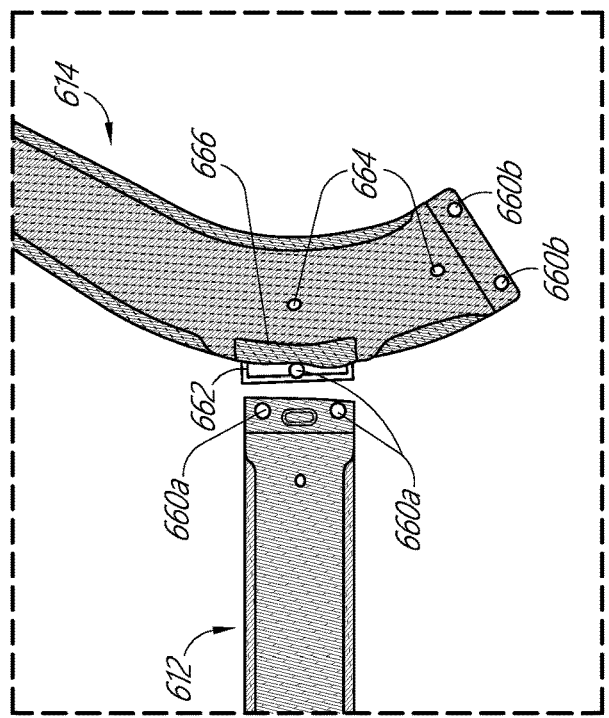
FIG. 55A is a partial internal view of the joint of FIG. 54A and an end of the bottom strap.

As described above, the front strap 614, first portion 620 of the top strap 612, and second portion 622 of the top strap 612 are formed independently from each other via intra-molding and then joined together via over-molded joints 624. As shown in FIGS. 52A-52B, the top strap 612 includes at least one alignment post 660 (e.g., two alignment posts 660a in the illustrated embodiment) proximate each of the fixed ends. As shown in FIG. 53A-53B, the bottom strap 614 includes at least one alignment post 660 (e.g., two alignment posts 660b in the illustrated embodiment) proximate each end. The bottom strap 614 includes at least one alignment post 660 (e.g., one alignment post 660c in the illustrated embodiment) positioned in each of two tabs 662 extending from an upper or top edge of the bottom strap 614. In some embodiments, the tabs 662 are formed via a burst-through process. The alignment posts 660 protrude through the outer casing on the internal and/or external surface of the top strap 612. The alignment posts 660 abut internal surfaces of an over-molding tool cavity to assist with alignment and positioning of the ends of the first portion 620 and second portion 622 (e.g., in a thickness direction) with respect to the front strap 614 within the over-molding tool during manufacturing. The alignment posts 660 also or alternatively increase the surface area of the top strap 612 available for the over-molding material to bond with.

The top strap 612 and/or bottom strap 614 include one or more pin holes 664 extending partially into the thickness of the strap from the inner surface of the strap. In the illustrated embodiment, the first portion 620 and second portion 622 of the top strap 612 each include a pin hole 664 near the fixed ends, and the bottom strap 614 includes a pin hole 664 near each end and a pin hole 664 near each burst-through tab 662. The pin holes 664 are designed to receive pins that form part of the over-molding tool during manufacturing. The pins and pin holes 664 engage each other to retain the straps in predetermined positions within the over-molding tool and inhibit the straps from moving within the over-molding tool, for example, as the over-molding material (e.g., plastic) is injected into the tool.

Figure 56B:
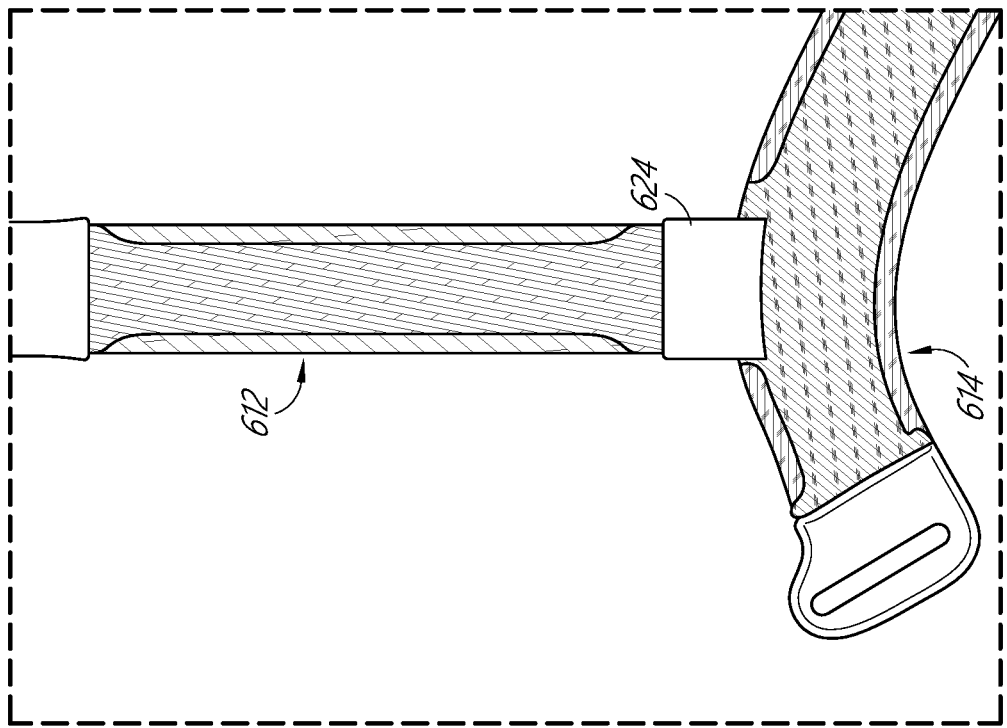
FIG. 56B is an external view of FIG. 56A.
Figure 56A:
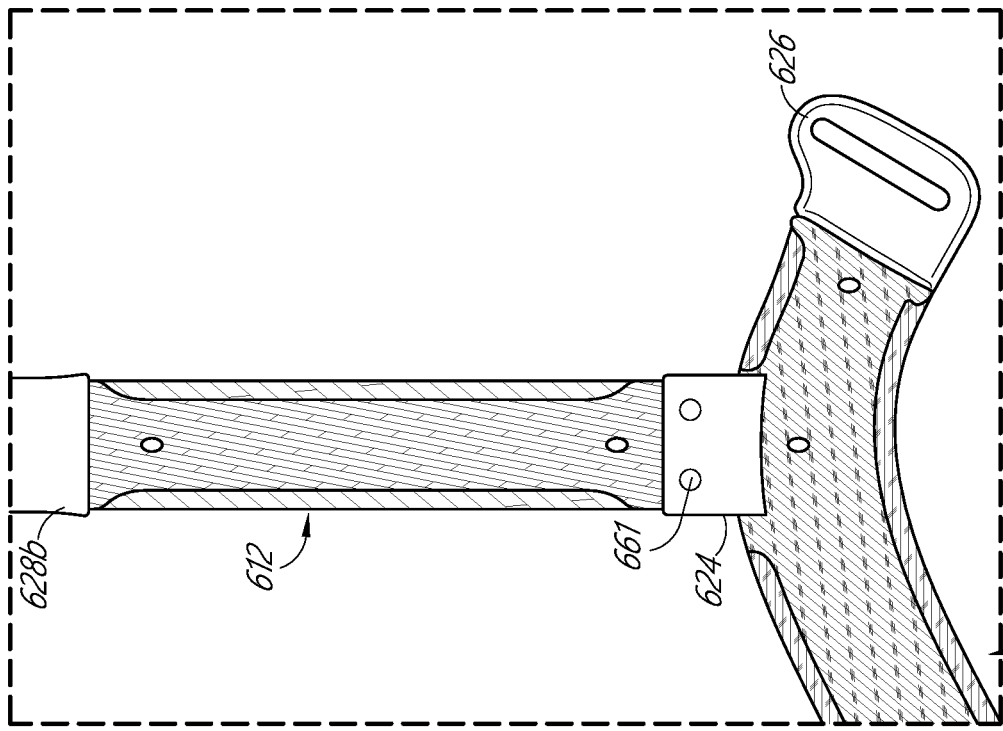
FIG. 56A is a partial internal view of an over-molded joint between the top strap and the bottom strap and a buckle over-molded onto the end of the bottom strap.
Figure 57:
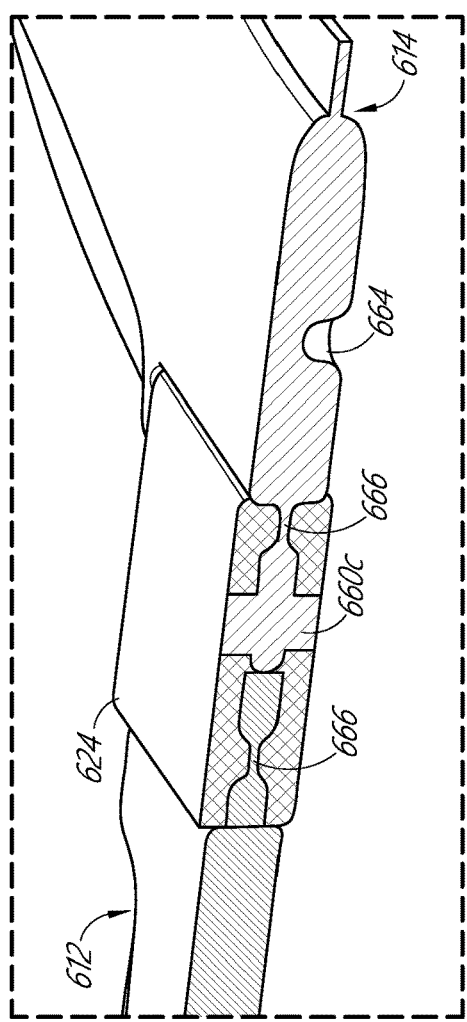
FIG. 57 is a section view of the over-molded joint of FIG. 56A.

During manufacturing, each of the fixed ends of the first portion 620 and second portion 622 is aligned with one of the burst-through tabs 662 as shown in FIGS. 54A-55B. As shown, the burst-through tabs 662, the fixed ends of the top strap 612, and/or the ends of the bottom strap 614 include indents 666 in the outer and/or inner surface. The indents 666 advantageously provide an increased thickness of over-mold material in the over-mold joints 624, as shown in FIG. 57, and/or an increased surface area for the over-mold material to bond with to improve the mechanical connection between the over-mold joint and the straps, thereby strengthening the joint 624. As shown in FIGS. 54A-55B, the burst-through tab 662 can have a reduced thickness compared to the thickness of a main body of the bottom strap 614. This reduced thickness forms a recess for the over-mold material to fill and allows the finished over-mold joint 624 to have a thickness that is the same as or similar to the thickness of the main body of the bottom strap 614 and/or top strap 612, as shown in FIGS. 56A-58. This inhibits the formation of protrusions that could apply force or pressure to the user's head and cause discomfort. In some embodiments, the alignment posts 660 have the same or a similar thickness as the over-mold joint 624, for example as shown in FIG. 57. In such embodiments, the alignment posts 660 may leave witness marks 661 in the over-mold joints 624. In some embodiments, the over-mold joint 624 overlaps the edge of the bottom strap 614, for example as shown in FIGS. 56A-56B. This improves the strength of the joint 624 between the top 612 and bottom 614 straps. The over-mold joints 624 advantageously provide improved strength to the joints between the top 612 and bottom 614 straps, and provide a neater and more aesthetically pleasing finish (e.g., compared to an intra-molded connection).

Figure 59:
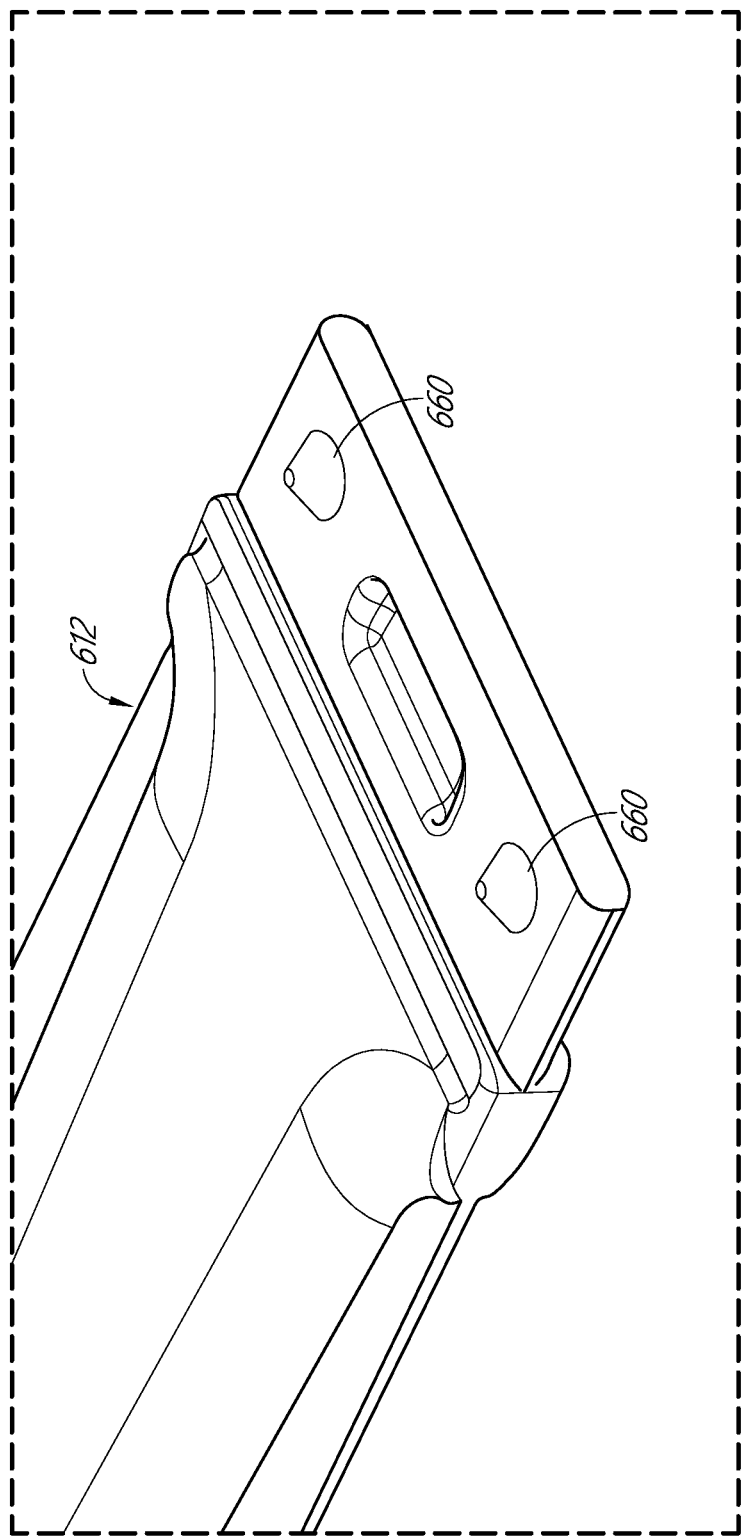
FIG. 59 is a perspective view of an alternative embodiment of an end of the top strap.
Figure 60A:
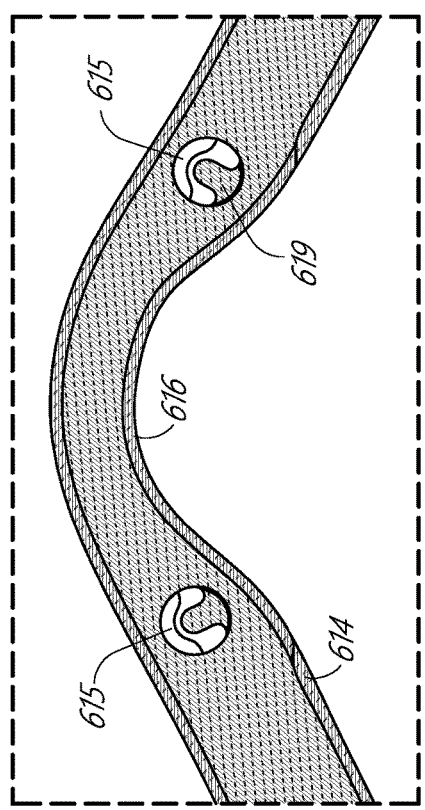
FIG. 60A is a rear view of the bottom strap and a yoke of the headgear of FIG. 46.
Figure 60B:
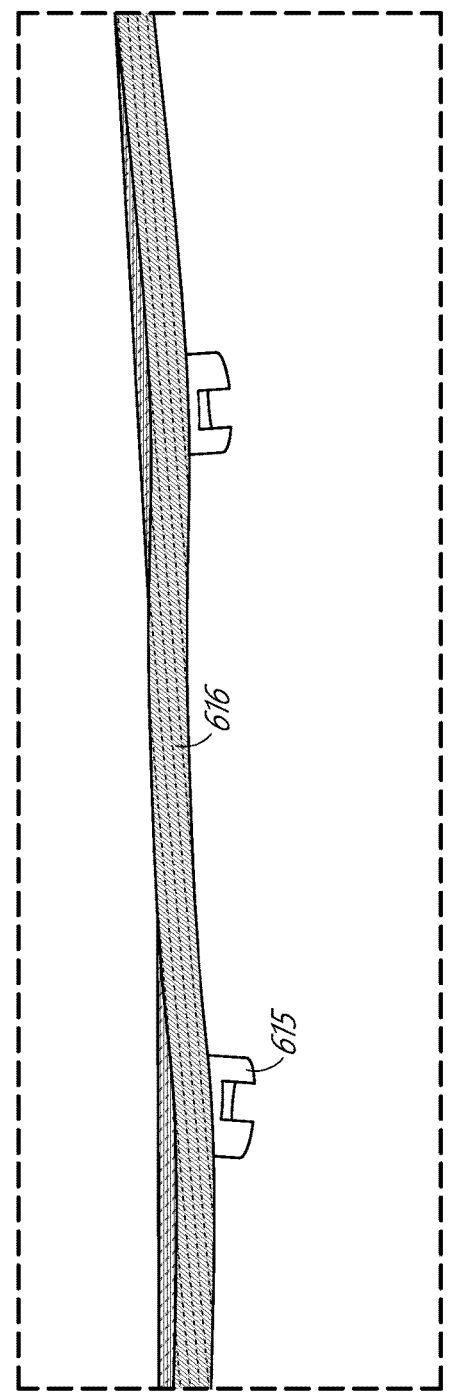
FIG. 60B is a bottom view of the yoke of FIG. 60A.
Figure 61:
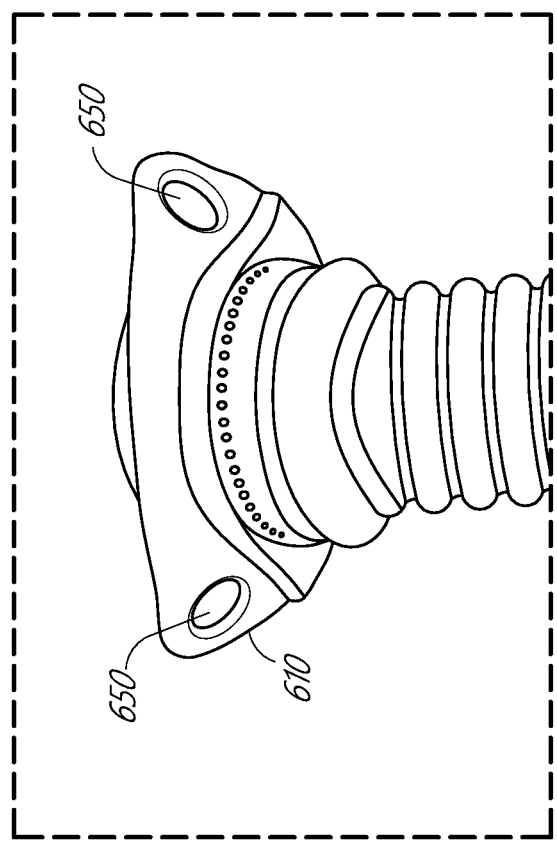
FIG. 61 is a front top perspective view of a frame and gas delivery conduit of the respiratory mask assembly of FIG. 44.
Figure 62A:
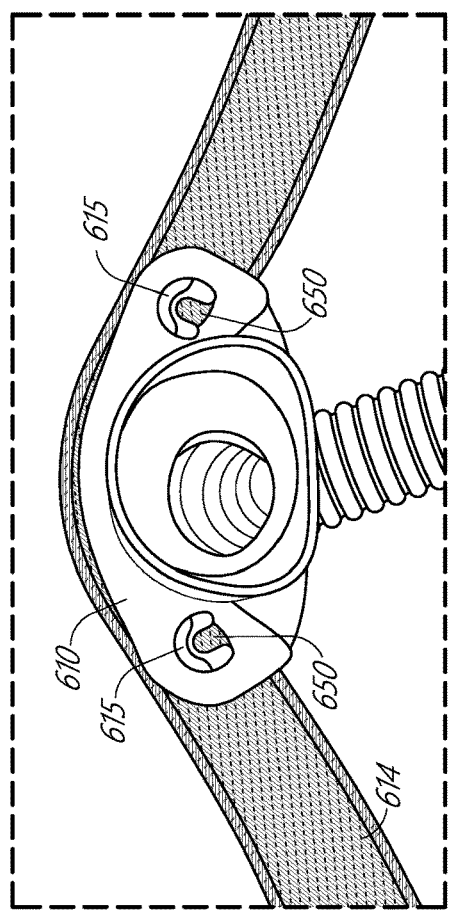
FIG. 62A is a rear view of the bottom strap of FIG. 60A coupled to the frame of FIG. 61.
Figure 62B:
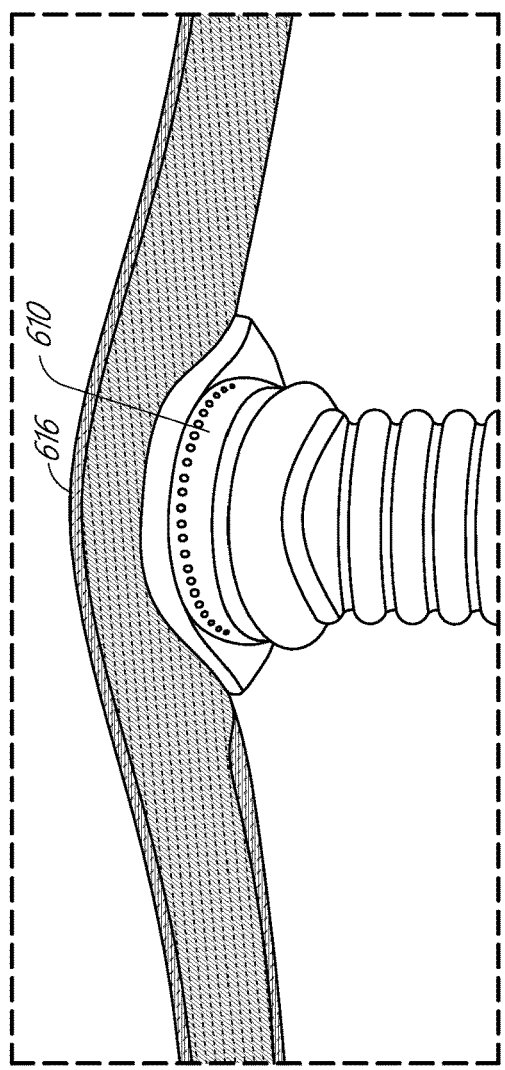
FIG. 62B is a front view of the bottom strap and frame of FIG. 62A.

FIG. 59 illustrates an example embodiment of a variation in the geometry of the alignment posts 660. In the illustrated embodiment, the alignment posts are conical. This shape minimizes or reduces witness marks on the finished over-molded joints 624. The distal end or surface of the alignment posts 660 (the end or surface of the alignment posts 660 away from the strap body) has a reduced diameter, which provides a smaller contact area with the internal surfaces of the over-mold tool cavity. This allows the over-mold material to cover a greater area of the alignment posts 660, which reduces the size of witness marks while still allowing the strap(s) to be positioned vertically within the over-mold tool.

Figure 58:
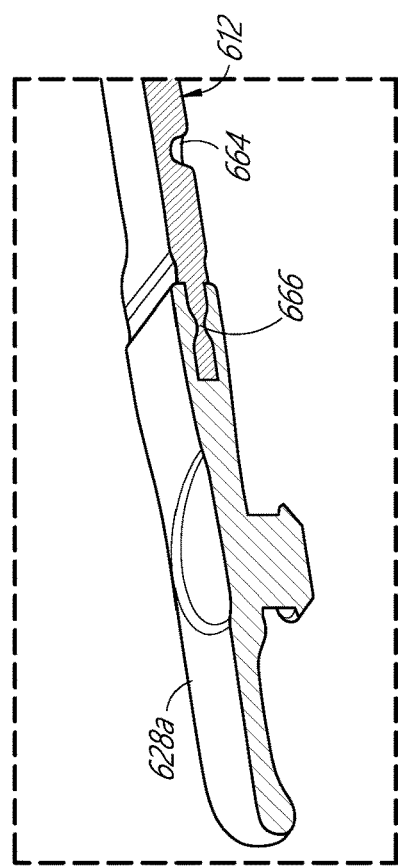
FIG. 58 is a section view of the male connector of FIG. 50A over-molded onto the top strap.

As shown in FIGS. 50C and 58, each of the first and second top strap portions have a textile encased portion and an exposed or plastic portion incorporating the inter-engaging portion. Each textile encased portion can be produced by intra-molding as described above. Each textile encased portion has a tab to which the respective exposed portion is over-molded.

As shown in FIGS. 47A-49B and 56A-56B, a buckle or rear strap connector 626 can be over-molded onto each end of the bottom strap 614. Each buckle 626 includes an aperture 627 configured to receive the rear strap 618. In the illustrated embodiment, the buckle 626 is not covered by the outer casing. The over-molded buckles 626 allow the rear strap 618 to be drawn through the buckles 626 more easily during assembly and/or adjustment due to the over-molded buckle 626 having a lower coefficient of friction than a textile covered buckle.

Figure 64:
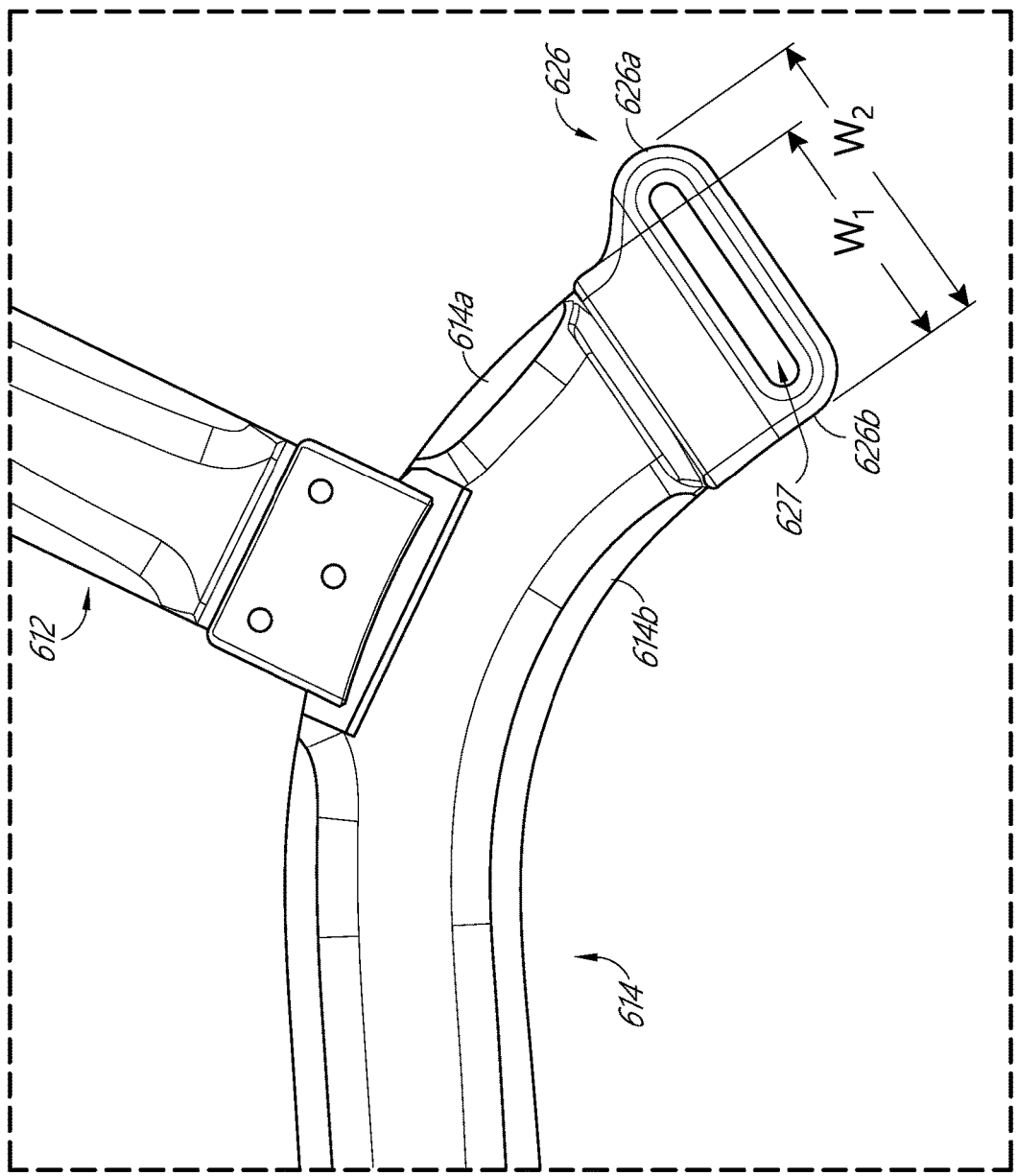
FIG. 64 shows relative dimensions of the buckle and bottom strap.

As shown in FIG. 64, each buckle 626 has a greater width $W_2$ than a width $W_1$ of the bottom strap 614, such that the rear strap 618, which has a width substantially the same as the bottom strap 614, can pass through the aperture 627 of the buckle 626. The upper edge 626*a* of each buckle 626 is offset from an upper edge 614*a* of the bottom strap 614. However, the lower edge 626*b* of the buckle 626 is in alignment with a lower edge 614*b* of the bottom strap 614. This provides a smooth and continuous lower edge of the headgear, which reduces the likelihood of the headgear digging into a user's ears when worn. The aperture 627 of the buckle 626 has a width that is substantially equal to a width of the rear strap 618. In some embodiments, the rear strap 618 is of substantially the same width as the bottom strap 614.

Similar to frame 410 and headgear 404, the frame 610 includes headgear retaining features 650 in the form of holes that are designed to receive projections 615 of the headgear 604. As shown in FIGS. 60A-62A, the projections 615, also referred to as frame retaining features or frame retention features herein, can be located on either side of the yoke 616. In the illustrated embodiment, the projections 615 have a horseshoe shape or "U" cross-section with an inlet 619 extending from the perimeter of the projection 615 toward, to, and/or through a center of the projection 615. The inlets 619 allow the projections 615 to flex to allow the projections 615 to snap into and/or out of the headgear retaining features 650.

Figure 63:
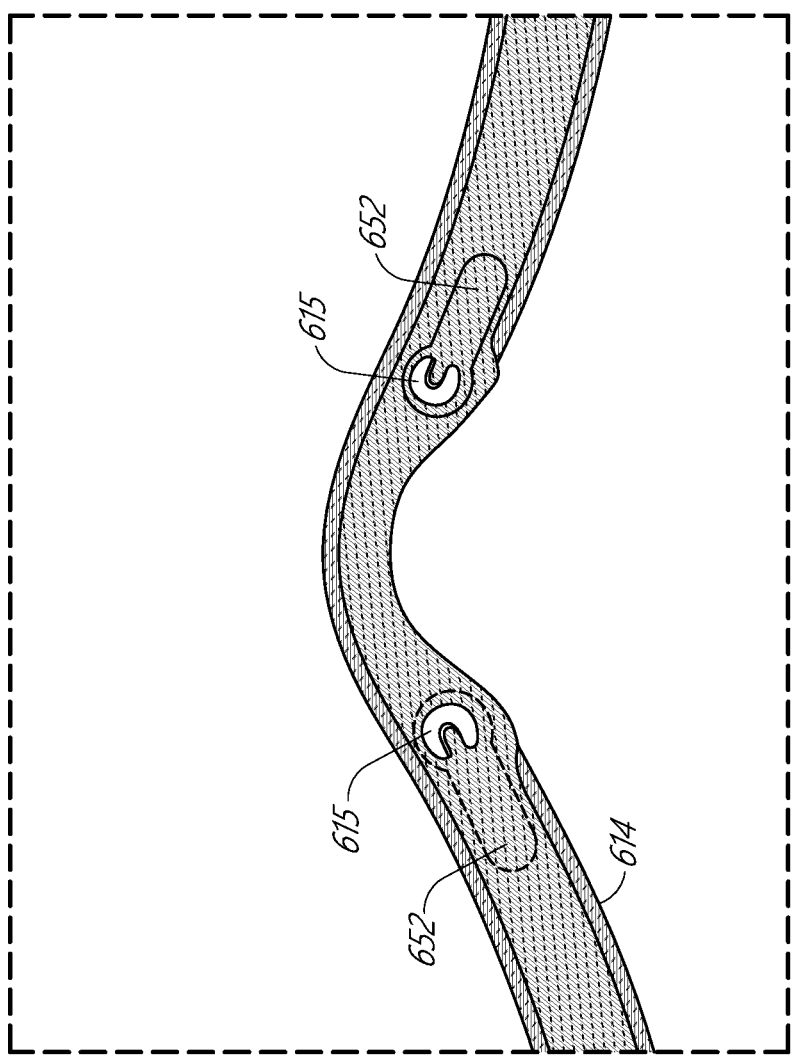
FIG. 63 is a rear view of an alternative embodiment of a bottom strap and yoke.

In some embodiments, for example as shown in FIG. 63, the bottom strap 614 includes a thumb pad 652 surrounding and/or extending laterally outwardly from each of frame retaining features 615 (toward the ends of the bottom strap 614 and the buckles 626). The thumb pads 652 are thicker than surrounding or remaining portions of the bottom strap 614. The thumb pads 652 advantageously provide increased strength and/or resilience to the yoke 616 such that the yoke 616 is less likely to permanently deform and/or become fatigued due to repeated removal from and/or attachment to the frame 610. The thumb pads 652 also or alternatively provide a visual indication to the user to grip the headgear 604 at this location (at the thumb pads 652) to disconnect the headgear 604 from and/or couple the headgear 604 to the frame 610. In the illustrated embodiment, the frame retention features 615 are oriented such that the inlets 619 (i.e., mouths of the inlets 619 in the perimeters of the frame retention features 615) face laterally outward (or toward the ends of the bottom strap 614 and the buckles 626). The inlets 619 are therefore aligned with the elongated portions of the thumb pads 652, which may be aesthetically pleasing. In some embodiments the thumb pads 652 provide an enhanced visual indicator in the form of a different coloured and/or textured region in the textile outer casing. The different coloured and/or textured region is integrally formed with the rest of the textile casing in some embodiments.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to." Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Language of degree used herein, such as the terms "approximately," "about," "generally," and "substantially," as used herein represent a value, amount or characteristic close to the stated value, amount or characteristic that still performs a desired function or achieves a desired result. The deviation from the stated value, amount or characteristic could, for example, reflect acceptable tolerances, conversion factors, rounding off, measurement error, or other factors known to those of skill in the art. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory mask system comprising:
a patient interface comprising:
a seal and a frame, and
a headgear comprising:
a front strap including a yoke configured to connect to the patient interface and a pair of side arms, each side arm configured to extend from a lateral side of the yoke and across a cheek and above an ear of a user;
a top strap configured in use to extend across the top of the user's head joining the pair of side arms; and
a rear strap configured to extend between the pair of side arms around the rear of the user's head;
the front strap including a region of increased thickness and at least one frame retaining feature, the at least one frame retaining feature being configured to engage a corresponding headgear retaining feature on the frame,
wherein the region of increased thickness comprises a pad surrounding and extending from the at least one frame retaining feature and laterally outward toward an end of the front strap, the pad having a greater thickness than a remainder of the front strap.

2. The respiratory mask system of claim 1, wherein the at least one frame retaining feature comprises a projection on the front strap.

3. The respiratory mask system of claim 2, wherein the projection is generally circular.

4. The respiratory mask system of claim 2, wherein the projection comprises a channel separating the projection into two portions.

5. The respiratory mask system of claim 2, wherein the projection has a horse-shoe or "U" shaped cross-section.

6. The respiratory mask system of claim 2, wherein the projection comprises an inlet configured to allow the projection to flex.

7. The respiratory mask system of claim 1, wherein the front strap and the top strap comprise a plastic core and a textile outer casing at least partially surrounding the plastic core.

8. The respiratory mask system of claim 7, wherein the at least one frame retaining feature extends through the textile outer casing from the plastic core.

9. The respiratory mask system of claim 1, wherein the at least one frame retaining feature is integrally formed with the front strap.

10. The respiratory mask system of claim 1, further comprising a buckle at a lateral end of each side arm, the buckles configured to receive the rear strap.

11. The respiratory mask system of claim 10, wherein the buckles are over-molded onto the lateral end of each side arm.

12. The respiratory mask system of claim 10, wherein a lower edge of each side arm and a lower edge of each buckle are aligned to form a continuous lower edge.

13. The respiratory mask system of claim 10, wherein the rear strap comprises a pair of lateral ends that are each adjustably connected to the buckles of the side arms.

14. The respiratory mask system of claim 1, wherein the frame comprises:
a body having an exterior surface and an interior surface extending from a first lateral edge to a second lateral edge,
an inlet collar extending from the exterior surface, the inlet collar defining an aperture and configured to be coupled to a gas conduit in use; and
an outlet collar extending from the interior surface;
wherein the body comprises a first headgear retaining feature positioned laterally at least partially between the inlet collar and the first lateral edge and a second headgear retaining feature positioned laterally at least partially between the inlet collar and the second lateral edge.

15. The respiratory mask system of claim 14, wherein the frame and the first and second headgear retaining features are configured such that the first headgear retaining feature can be engaged with a corresponding first frame retaining feature on the headgear and then the frame and the headgear can be rotated relative to each other about the first headgear retaining feature to align the second headgear retaining feature with a corresponding second frame retaining feature on the headgear.

16. The respiratory mask system of claim 14, wherein the inlet collar further comprises a conduit retaining projection extending radially inwards from a periphery of the inlet collar.

17. The respiratory mask system of claim 16, wherein the conduit retaining projection comprises a lip around a periphery of the inlet collar.

18. The respiratory mask system of claim 17, wherein the lip is continuous.

19. The respiratory mask system of claim 17, wherein the lip is intermittent.

20. The respiratory mask system of claim 1, wherein the front and top straps are made of a semi-rigid material.

21. The respiratory mask system of claim 1, wherein the front and top straps comprise a plastic material.

* * * * *